(12) United States Patent
Witschel et al.

(10) Patent No.: US 6,583,089 B1
(45) Date of Patent: Jun. 24, 2003

(54) TRICYCLIC BENZOYLCYCLOHEXANEDIONE DERIVATIVES

(75) Inventors: Matthias Witschel, Ludwigshafen (DE); Steffen Kudis, Mannheim (DE); Klaus Langemann, Worms (DE); Ernst Baumann, Dudenhofen (DE); Wolfgang von Deyn, Neustadt (DE); Guido Mayer, Neustadt (DE); Ulf Misslitz, Neustadt (DE); Ulf Neidlein, Mannheim (DE); Martina Otten, Ludwigshafen (DE); Karl-Otto Westphalen, Speyer (DE); Helmut Walter, Obrigheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/979,991

(22) PCT Filed: May 26, 2000

(86) PCT No.: PCT/EP00/04806

§ 371 (c)(1),
(2), (4) Date: Nov. 29, 2001

(87) PCT Pub. No.: WO00/73311

PCT Pub. Date: Dec. 7, 2000

(30) Foreign Application Priority Data

Jun. 1, 1999 (DE) .......................... 199 25 103

(51) Int. Cl.⁷ .................. A01N 43/90; C07D 498/04
(52) U.S. Cl. .................. 504/271; 548/242; 548/151; 548/218; 548/302.1; 548/359.5; 504/266; 504/270; 504/276; 504/281

(58) Field of Search ................. 504/271, 266, 504/270, 276, 281; 548/242, 151, 218, 302.1, 359.5

(56) References Cited

FOREIGN PATENT DOCUMENTS

| EP | 283 261 | 9/1988 |
| EP | 860 441 | 8/1998 |
| WO | 97/19087 | 5/1997 |

*Primary Examiner*—Charanjit S. Aulakh
(74) *Attorney, Agent, or Firm*—Keil & Weinkauf

(57) ABSTRACT

Tricyclic benzoylcyclohexanedione derivatives of the formula I

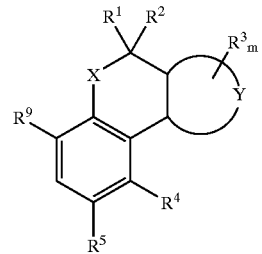

where X, Y, R¹, R², R³, R⁴, R⁵, R⁹, and m are defined herein, and their agriculturally useful salts. Process for preparing the tricyclic benzoylcyclohexanedione derivatives; compositions comprising them and the use of these derivatives or of the compositions comprising them for controlling undesirable plants are described.

9 Claims, No Drawings

TRICYCLIC BENZOYLCYCLOHEXANEDIONE DERIVATIVES

This application is a 371 of PCT/EP 00/04806 filed May 26, 2000, now WO 00/73311, Dec. 7, 2000.

The present invention relates to novel tricyclic benzoyl-cyclohexanedione derivatives of the formula I

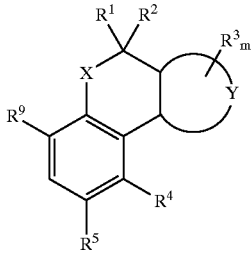

where:

X is oxygen, sulfur, S=O, S(=O)$_2$, CR$^6$R$^7$, NR$^8$ or a bond;

Y together with the two carbons to which it is attached forms a saturated, partially saturated or unsaturated 5- or 6-membered heterocycle which contains one to three identical or different heteroatoms selected from the following group: oxygen, sulfur or nitrogen;

R$^1$, R$^2$, R$^6$, R$^7$ are hydrogen, C$_1$–C$_6$-alkyl, C$_1$–C$_6$-haloalkyl, C$_1$–C$_6$-alkoxy or C$_1$–C$_6$-haloalkoxy;

R$^3$ is halogen, C$_1$–C$_6$-alkyl, C$_1$–C$_6$-haloalkyl, C$_1$–C$_6$-alkoxy or C$_1$–C$_6$-haloalkoxy;

R$^4$ is hydrogen, nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, N—(C$_1$–C$_6$-alkyl)aminosulfonyl, N,N-di-(C$_1$–C$_6$-alkyl)aminosulfonyl, N—(C$_1$–C$_6$-alkylsulfonyl)amino, N—(C$_1$–C$_6$-haloalkylsulfonyl)amino, N—(C$_1$–C$_6$-alkyl)-N—(C$_1$–C$_6$-alkylsulfonyl)amino or N—(C$_1$–C$_6$-alkyl)-N—(C$_1$–C$_6$-haloalkylsulfonyl)amino;

R$^5$ is hydrogen, C$_1$–C$_6$-alkyl or halogen;

R$^8$ is hydrogen, C$_1$–C$_6$-alkyl, C$_1$–C$_6$-haloalkyl, C$_1$–C$_6$-alkylcarbonyl, formyl, C$_1$–C$_6$-alkoxycarbonyl, C$_1$–C$_6$-haloalkoxycarbonyl, C$_1$–C$_6$-alkylsulfonyl or C$_1$–C$_6$-haloalkylsulfonyl;

m is 0, 1 or 2;

R$^9$ is a radical IIa or IIb

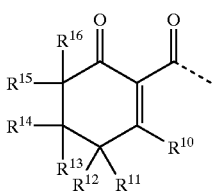

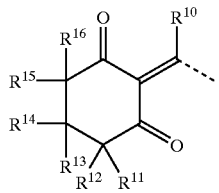

where:

R$^{10}$ is hydroxyl, mercapto, halogen, OR$^{17}$, SR$^{17}$, SOR$^{18}$, SO$_2$R$^{18}$, OSO$_2$R$^{18}$, NR$^{19}$R$^{20}$ or N-bonded heterocyclyl which may be partially or fully halogenated and/or may carry one to three of the following radicals: nitro, cyano, C$_1$–C$_4$-alkyl, C$_1$–C$_4$-haloalkyl, C$_1$–C$_4$-alkoxy or C$_1$–C$_4$-haloalkoxy;

R$^{11}$, R$^{15}$ are hydrogen, C$_1$–C$_4$-alkyl or C$_1$–C$_4$-alkoxycarbonyl;

R$^{12}$, R$^{14}$, R$^{16}$ are hydrogen or C$_1$–C$_4$-alkyl;

R$^{13}$ is hydrogen, halogen, hydroxyl, C$_1$–C$_6$-alkyl, C$_1$–C$_6$-haloalkyl, di-(C$_1$–C$_6$-alkoxy)methyl, (C$_1$–C$_6$-alkoxy)-(C$_1$–C$_6$-alkylthio)methyl, di-(C$_1$–C$_6$-alkylthio)methyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, C$_1$–C$_6$-alkoxycarbonyl, C$_1$–C$_6$-haloalkoxycarbonyl; is 1,3-dioxolan-2-yl, 1,3-dioxan-2-yl, 1,3-oxathiolan-2-yl, 1,3 oxathian-2-yl, 1,3-dithiolan-2-yl or 1,3-dithian-2-yl, where the six last-mentioned radicals may be substituted by one to three C$_1$–C$_4$-alkyl radicals; or R$^{12}$ and R$^{13}$ or R$^{13}$ and R$^{16}$ together form a π-bond or a C$_1$–C$_5$-alkyl chain which may carry one to three radicals from the following group: halogen, cyano, C$_1$–C$_4$-alkyl, C$_1$–C$_4$-haloalkyl or C$_1$–C$_4$-alkoxycarbonyl; or R$^{12}$ and R$^{16}$ together form a C$_1$–C$_4$-alkyl chain which may carry one to three radicals from the following group: halogen, cyano, C$_1$–C$_4$-alkyl, C$_1$–C$_4$-haloalkyl or C$_1$–C$_4$-alkoxycarbonyl; or R$^{13}$ and R$^{14}$ together form a —O—(CH$_2$)$_p$—O—, —O—(CH$_2$)$_p$—S—, —S—(CH$_2$)$_p$—S—, —O—(CH$_2$)$_q$— or —S—(CH$_2$)$_q$— chain which may be substituted by one to three radicals from the following group: halogen, cyano, C$_1$–C$_4$-alkyl, C$_1$–C$_4$-haloalkyl or C$_1$–C$_4$-alkoxycarbonyl; or R$^{13}$ and R$^{14}$ together with the carbon to which they are attached form a carbonyl group;

R$^{17}$ is C$_1$–C$_6$-alkyl, C$_3$–C$_6$-alkenyl, C$_3$–C$_6$-haloalkenyl, C$_3$–C$_6$-alkynyl, C$_3$–C$_6$-haloalkynyl, C$_3$–C$_6$-cycloalkyl, C$_1$–C$_{20}$-alkylcarbonyl, C$_2$–C$_6$-alkenylcarbonyl, C$_2$–C$_6$-alkynylcarbonyl, C$_3$–C$_6$-cycloalkylcarbonyl, C$_1$–C$_6$-alkoxycarbonyl, C$_3$–C$_6$-alkenyloxycarbonyl, C$_3$–C$_6$-alkynyloxycarbonyl, C$_1$–C$_6$-alkylthiocarbonyl, C$_1$–C$_6$-alkylaminocarbonyl, C$_3$–C$_6$-alkenylaminocarbonyl, C$_3$–C$_6$-alkynylaminocarbonyl, N,N-di(C$_1$–C$_6$-alkyl)aminocarbonyl, N—(C$_3$–C$_6$-alkenyl)-N—(C$_1$–C$_6$-alkyl)aminocarbonyl, N—(C$_3$–C$_6$-alkynyl)-N—(C$_1$–C$_6$-alkyl)aminocarbonyl, N—(C$_1$–C$_6$-alkoxy)-N—(C$_1$–C$_6$-alkyl)aminocarbonyl, N—(C$_3$–C$_6$-alkenyl)-N—(C$_1$–C$_6$-alkoxy)aminocarbonyl, N—(C$_3$–C$_6$-alkynyl)-N—(C$_1$–C$_6$-alkoxy)aminocarbonyl, di-(C$_1$–C$_6$-alkyl)aminothiocarbonyl, C$_1$–C$_6$-alkoxyimino-C$_1$–C$_6$-alkyl, where the alkyl, cycloalkyl or alkoxy radicals mentioned may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenylaminocarbonyl, N—($C_1$–$C_6$-alkyl)-N-phenylaminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylaminocarbonyl, N—($C_1$–$C_6$-alkyl)-N-heterocyclylaminocarbonyl or heterocyclyl-$C_1$–$C_6$-alkenylcarbonyl, where the phenyl or the heterocyclyl radical of the 18 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{17}$ [sic] is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one to three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_4$-alkyl, heterocyclyl or heterocyclyl-$C_1$–$C_4$-alkyl, where the phenyl or the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{19}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-($C_1$–$C_6$-alkyl)amino or $C_1$–$C_6$-alkylcarbonylamino, where the alkyl, cycloalkyl or alkoxy radicals mentioned may be partially or fully halogenated and/or may carry one to three of the following radicals: cyano, $C_1$–$C_4$-alkoxycarbonyl, $C_1$–$C_4$-alkylaminocarbonyl, di-($C_1$–$C_4$-alkyl)aminocarbonyl or $C_3$–$C_6$-cycloalkyl;

is phenyl, phenyl-$C_1$–$C_4$-alkyl, phenylcarbonyl, heterocyclyl, heterocycly-$C_1$–$C_4$-alkyl [sic] or heterocyclylcarbonyl, where the phenyl or heterocyclyl radical of the six last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is hydrogen, $C_1$–$C_6$-alkyl, $C_3$–$C_6$-alkenyl or $C_3$–$C_6$-alkynyl;

p is 2, 3 or 4;

q is 1, 2, 3, 4 or 5;

and their agriculturally useful salts.

Moreover, the invention relates to processes for preparing compounds of the formula I, to compositions comprising them and to the use of these derivatives or of the compositions comprising them for controlling harmful plants.

WO 97/19087 and EP-A 860 441 disclose tricyclic compounds which are characterized in that the benzoyl unit that they contain in each case is fused to a bicycle via positions 3 and 4. However, the herbicidal properties of the prior-art compounds and their compatibility with crop plants are not entirely satisfactory.

It is an object of the present invention to provide novel biological, in particular herbicidally active, compounds having improved properties.

We have found that this object is achieved by the tricyclic benzoylcyclohexanedione derivatives of the formula I and their herbicidal action.

Furthermore, we have found processes for synthesizing the compounds of the formula I. We have also found herbicidal compositions which comprise the compounds I and have very good herbicidal action. Moreover, we have found processes for preparing these compositions and methods for controlling undesirable vegetation using the compounds I.

Depending on the substitution pattern, the compounds of the formula I may contain one or more chiral centers, in which case they are present as enantiomers or diastereomer mixtures. The invention provides both the pure enantiomers or diestereomers and their mixtures.

The compounds of the formula I can also be present in the form of their agriculturally useful salts, the type of salt usually being immaterial. In general, the salts of those cations and the acid addition salts of those acids are suitable whose cations and anions, respectively, do not adversely affect the herbicidal action of the compounds I.

Suitable cations are, in particular, ions of the alkali metals, preferably lithium, sodium or potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl) sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

In the case of $R^{10}$=hydroxyl or mercapto, IIa also represents the tautomeric forms IIa', IIa" and IIa'"

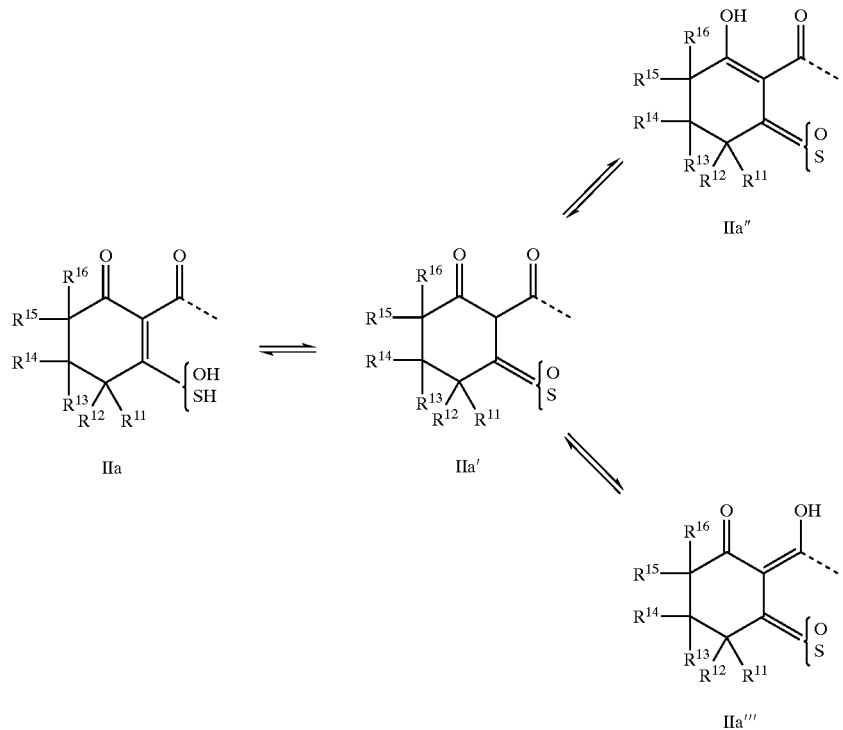
and IIb also represents the tautomeric forms IIb', IIb" and IIb'''.
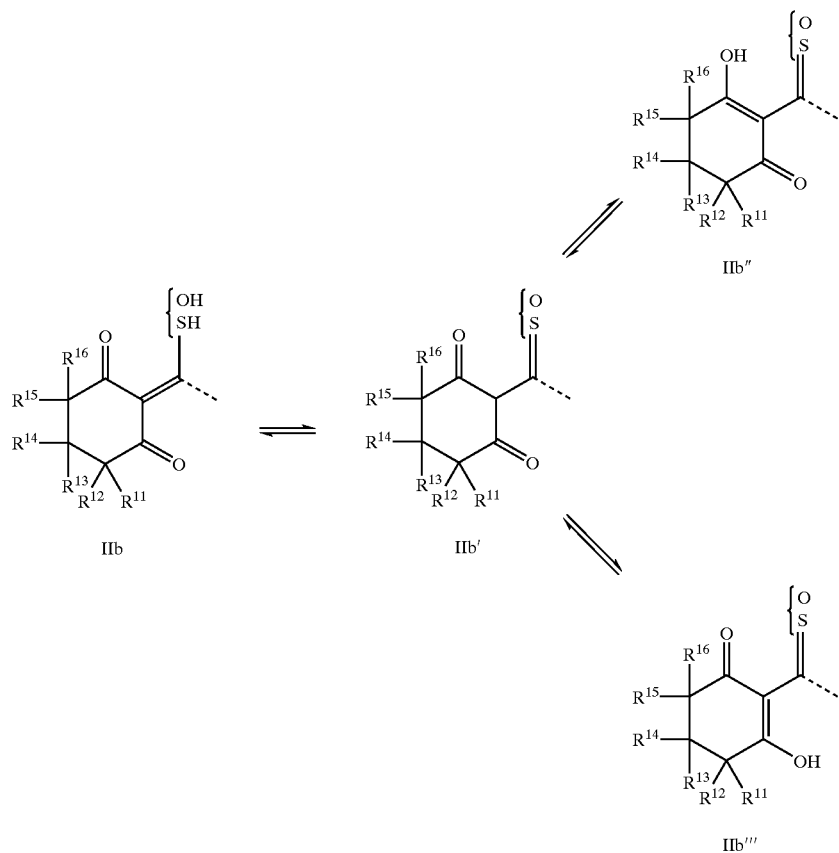

The organic molecular moieties mentioned for the substituents $R^1$–$R^{20}$ or as radicals on phenyl and heterocyclyl radicals, and all other radicals listed in this application, are collective terms for individual enumerations of the individual group members. All hydrocarbon chains, i.e. all alkyl, haloalkyl, hydroxyalkyl, di(alkoxy)methyl, (alkoxy)(alkylthio)methyl, di(alkylthio)methyl, alkoxy-, haloalkoxy-, alkylthio-, haloalkylthio-, alkylsulfinyl, haloalkylsulfinyl-, alkylsulfonyl-, haloalkylsulfonyl-, N-alkylaminosulfonyl, N,N-dialkylaminosulfonyl, trialkylsulfonium, trialkylsulfoxonium, N-alkylamino, N,N-dialkylamino, alkylcarbonylamino, N-alkylsulfonylamino, N-haloalkylsulfonylamino, N-alkyl-N-alkylsulfonylamino, N-alkyl-N-haloalkylsulfonylamino, alkylcarbonyl-, alkoxycarbonyl-, haloalkyoxycarbonyl [sic], alkylthiocarbonyl, alkylcarbonyloxy-, alkylaminocarbonyl-, dialkylaminocarbonyl-, dialkylaminothiocarbonyl, alkoxyalkyl-, hydroxyalkoxyalkyl, alkoxyiminoalkyl, phenylalkenylcarbonyl, heterocyclylalkenylcarbonyl, N-alkoxy-N-alkylaminocarbonyl-, N-alkyl-N-phenylaminocarbonyl-, N-alkyl-N-heterocyclylaminocarbonyl-, phenylalkyl-, heterocyclylalkyl-, phenylcarbonylalkyl-, heterocyclylcarbonylalkyl-, alkoxyalkoxycarbonyl-, alkenylcarbonyl-, alkenyloxycarbonyl-, alkenylaminocarbonyl-, N-alkenyl-N-alkylaminocarbonyl-, N-alkenyl-N-alkoxyaminocarbonyl-, alkynylcarbonyl-, alkynyloxycarbonyl-, alkynylaminocarbonyl-, N-alkynyl-N-alkylaminocarbonyl-, N-alkynyl-N-alkoxyaminocarbonyl-, alkenyl-, alkynyl-, haloalkenyl-, haloalkynyl-, alkenyloxy and alkynyloxy moieties may be straight-chain or branched. Unless indicated otherwise, halogenated substituents preferably carry one to five identical or different halogen atoms. The term halogen represents in each case fluorine, chlorine, bromine or iodine.

Examples of other meanings are:

$C_1$–$C_4$-alkyl and the alkyl moieties of hydroxy-$C_1$–$C_4$-alkyl, tri-($C_1$–$C_4$-alkyl)sulfonium and tri-($C_1$–$C_4$-alkyl)sulfoxonium: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkoxyimino-$C_1$–$C_6$-alkyl, N—($C_1$–$C_6$-alkoxy)-N—($C_1$–$C_6$-alkyl)aminocarbonyl, N—($C_3$–$C_6$-alkenyl)-N—($C_1$–$C_6$-alkyl)aminocarbonyl, N—($C_3$–$C_6$-alkynyl)-N—($C_1$–$C_6$-alkyl)aminocarbonyl, N—($C_1$–$C_6$-alkyl)-N-phenylaminocarbonyl, N—($C_1$–$C_6$-alkyl)-N-heterocyclylaminocarbonyl, phenyl-$C_1$–$C_6$-alkyl, N—($C_1$–$C_6$-alkyl)-N—($C_1$–$C_6$-alkylsulfonyl)-amino, N—($C_1$–$C_6$-alkyl)-N—($C_1$–$C_6$-haloalkylsulfonyl)amino, heterocyclyl-$C_1$–$C_6$-alkyl, phenylcarbonyl-$C_1$–$C_6$-alkyl, heterocyclylcarbonyl-$C_1$–$C_6$-alkyl: $C_1$–$C_4$-alkyl as mentioned above, and also, for example, phenyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of di-($C_1$–$C_6$-alkoxy)-methyl, ($C_1$–$C_6$-alkoxy)($C_1$–$C_6$-alkylthio)methyl, $C_1$–$C_6$-alkoxyimino-$C_1$–$C_6$-alkyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl and N—($C_3$–$C_6$-alkynyl)-N—($C_1$–$C_6$-alkoxy)aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-di-chloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio or 1,1-dimethylethylthio;

$C_1$–$C_6$-alkylthio, and the alkylthio moieties of ($C_1$–$C_6$-alkoxy)($C_1$–$C_6$-alkylthio)methyl, di($C_1$–$C_6$-alkylthio)methyl and $C_1$–$C_6$-alkylthiocarbonyl: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e. for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_6$-haloalkylthio: $C_1$–$C_4$-haloalkylthioo [sic] as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: $C_1$–$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_6$-alkylsulfonyl ($C_1$–$C_6$-alkyl-S(=O)$_2$—), and the alkylsulfonyl radicals of N—($C_1$–$C_6$-alkylsulfonyl)amino and N—($C_1$–$C_6$-alkyl)-N—($C_1$–$C_6$-alkylsulfonyl)amino: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl, and the haloalkylsulfonyl radicals of N—($C_1$–$C_6$-haloalkylsulfonyl)amino and N—($C_1$–$C_6$-alkyl)-N—($C_1$–$C_6$-haloalkylsulfonyl)amino: a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino: for example, methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

($C_1$–$C_6$-alkylamino)sulfonyl: for example methylaminosulfonyl, ethylaminosulfonyl, propylaminosulfonyl, 1-methylethylaminosulfonyl, butylaminosulfonyl, 1-methylpropylaminosulfonyl, 2-methylpropylaminosulfonyl, 1,1-dimethylethylaminosulfonyl, pentylaminosulfonyl, 1-methylbutylaminosulfonyl, 2-methylbutylaminosulfonyl, 3-methylbutylaminosulfonyl, 2,2-dimethylpropylaminosulfonyl, 1-ethylpropylaminosulfonyl, hexylaminosulfonyl, 1,1-dimethylpropylaminosulfonyl, 1,2-dimethylpropylaminosulfonyl, 1-methylpentylaminosulfonyl, 2-methylpentylaminosulfonyl, 3-methylpentylaminosulfonyl, 4-methylpentylaminosulfonyl, 1,1-dimethylbutylaminosulfonyl, 1,2-dimethylbutylaminosulfonyl, 1,3-dimethylbutylaminosulfonyl, 2,2-dimethylbutylaminosulfonyl, 2,3-dimethylbutylaminosulfonyl, 3,3-dimethylbutylaminosulfonyl, 1-ethylbutylaminosulfonyl, 2-ethylbutylaminosulfonyl, 1,1,2-trimethylpropylaminosulfonyl, 1,2,2-trimethylpropylaminosulfonyl, 1-ethyl-1-methylpropylaminosulfonyl or 1-ethyl-2-methylpropylaminosulfonyl;

di($C_1$–$C_6$-alkyl)aminosulfonyl: for example N,N-dimethylaminosulfonyl, N,N-diethylaminosulfonyl, N,N-di(1-methylethyl)aminosulfonyl, N,N-dipropylaminosulfonyl, N,N-dibutylaminosulfonyl, N,N-di(1-methylpropyl)aminosulfonyl, N,N-di(2-methylpropyl)aminosulfonyl, N,N-di(1,1-dimethylethyl)aminosulfonyl, N-ethyl-N-methylaminosulfonyl, N-methyl-N-propylaminosulfonyl, N-methyl-N-(1-methylethyl)aminosulfonyl, N-butyl-N-methylaminosulfonyl, N-methyl-N-(1-methylpropyl)aminosulfonyl, N-methyl-N-(2-methylpropyl)aminosulfonyl, N-(1,1-dimethylethyl)-N-methylaminosulfonyl, N-ethyl-N-propylaminosulfonyl, N-ethyl-N-(1-methylethyl)aminosulfonyl, N-butyl-N-ethylaminosulfonyl, N-ethyl-N-(1-methylpropyl)aminosulfonyl, N-ethyl-N-(2-methylpropyl)aminosulfonyl, N-ethyl-N-(1,1-dimethylethyl)aminosulfonyl, N-(1-methylethyl)-N-propylaminosulfonyl, N-butyl-N-propylaminosulfonyl, N-(1-methylpropyl)-N-propylaminosulfonyl, N-(2-methylpropyl)-N-propylaminosulfonyl, N-(1,1-dimethylethyl)-N-propylaminosulfonyl, N-butyl-N-(1-methylethyl)aminosulfonyl, N-(1-methylethyl)-N-(1-methylpropyl)aminosulfonyl, N-(1-methylethyl)-N-(2-methylpropyl)aminosulfonyl, N-(1,1-dimethylethyl)-N-(1-methylethyl)aminosulfonyl, N-butyl-N-(1-methylpropyl)aminosulfonyl, N-butyl-N-(2-methylpropyl)aminosulfonyl, N-butyl-N-(1,1-dimethylethyl)aminosulfonyl, N-(1-methylpropyl)-N-(2-methylpropyl)aminosulfonyl, N-(1,1-dimethylethyl)-N-(1-methylpropyl)aminosulfonyl, N-(1,1-dimethylethyl)-N-(2-methylpropyl)aminosulfonyl, N-methyl-N-pentylaminosulfonyl, N-methyl-N-(1-methylbutyl)aminosulfonyl, N-methyl-N-(2-methylbutyl)aminosulfonyl, N-methyl-N-(3-methylbutyl)aminosulfonyl, N-methyl-N-(2,2-dimethylpropyl)aminosulfonyl, N-methyl-N-(1-ethylpropyl)aminosulfonyl, N-methyl-N-hexylaminosulfonyl, N-methyl-N-(1,1-dimethylpropyl)aminosulfonyl, N-methyl-N-(1,2-dimethylpropyl)aminosulfonyl, N-methyl-N-(1-methylpentyl)aminosulfonyl, N-methyl-N-(2-methylpentyl)aminosulfonyl, N-methyl-N-(3-methylpentyl)aminosulfonyl, N-methyl-N-(4-methylpentyl)aminosulfonyl, N-methyl-N-(1,1-dimethylbutyl)aminosulfonyl, N-methyl-N-(1,2-dimethylbutyl)aminosulfonyl, N-methyl-N-(1,3-dimethylbutyl)aminosulfonyl, N-methyl-N-(2,2-dimethylbutyl)aminosulfonyl, N-methyl-N-(2,3-dimethylbutyl)aminosulfonyl, N-methyl-N-(3,3-dimethylbutyl)aminosulfonyl, N-methyl-N-(1-ethylbutyl)aminosulfonyl, N-methyl-N-(2-ethylbutyl)aminosulfonyl, N-methyl-N-(1,1,2-trimethylpropyl)aminosulfonyl, N-methyl-N-(1,2,2-trimethylpropyl)aminosulfonyl, N-methyl-N-(1-ethyl-1-methylpropyl)aminosulfonyl, N-Methyl-N-(1-ethyl-2-methylpropyl)aminosulfonyl, N-ethyl-N-pentylaminosulfonyl, N-ethyl-N-(1-methylbutyl)aminosulfonyl, N-ethyl-N-(2-methylbutyl)aminosulfonyl, N-ethyl-N-(3-methylbutyl)aminosulfonyl, N-ethyl-N-(2,2-dimethylpropyl)aminosulfonyl, N-ethyl-N-(1-ethylpropyl)aminosulfonyl, N-ethyl-N-hexylaminosulfonyl, N-ethyl-N-(1,1-dimethylpropyl)aminosulfonyl, N-ethyl-N-(1,2-dimethylpropyl)aminosulfonyl, N-ethyl-N-(1-methylpentyl)aminosulfonyl, N-ethyl-N-(2-methylpentyl)aminosulfonyl, N-ethyl-N-(3-methylpentyl)aminosulfonyl, N-ethyl-N-(4-methylpentyl)aminosulfonyl, N-ethyl-N-(1,1-dimethylbutyl)aminosulfonyl, N-ethyl-N-(1,2-dimethylbutyl)aminosulfonyl, N-ethyl-N-(1,3-dimethylbutyl)aminosulfonyl, N-ethyl-N-(2,2-dimethylbutyl)aminosulfonyl, N-ethyl-N-(2,3-dimethylbutyl)aminosulfonyl, N-ethyl-N-(3,3-dimethylbutyl)aminosulfonyl, N-ethyl-N-(1-ethylbutyl)aminosulfonyl, N-ethyl-N-(2-ethylbutyl)aminosulfonyl, N-ethyl-N-(1,1,2-trimethylpropyl)aminosulfonyl, N-ethyl-N-(1,2,2-trimethylpropyl)aminosulfonyl, N-ethyl-N-(1-ethyl-1-methylpropyl)aminosulfonyl, N-ethyl-N-(1-ethyl-2-methylpropyl)aminosulfonyl, N-propyl-N-pentylaminosulfonyl, N-butyl-N-pentylaminosulfonyl, N,N-dipentylaminosulfonyl, N-propyl-N-hexylaminosulfonyl, N-butyl-N-hexylaminosulfonyl, N-pentyl-N-hexylaminosulfonyl or N,N-dihexylaminosulfonyl;

di($C_1$–$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N- methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino: a di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonylamino: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2,-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_{20}$-alkylcarbonyl: $C_1$–$C_6$-alkylcarbonyl as mentioned above, and also heptylcarbonyl, octylcarbonyl, pentadecylcarbonyl or heptadecylcarbonyl;

$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$–$C_6$-alkoxy)carbonyl: ($C_1$–$C_4$-alkoxy)carbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_4$-haloalkoxycarbonyl: a $C_1$–$C_4$-alkoxycarbonyl radical as mentioned above which is partially or fully substituted by fluorine, chlorine, bromine and/or iodine, i.e., for example, fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl or nonafluorobutoxycarbonyl;

$C_1$–$C_6$-haloalkoxycarbonyl: $C_1$–$C_4$-haloalkoxycarbonyl as mentioned above, and also 5-fluoropentoxycarbonyl, 5-chloropentoxycarbonyl, 5-bromopentoxycarbonyl, 5-iodopentoxycarbonyl, 6-fluorohexoxycarbonyl, 6-bromohexoxycarbonyl, 6-iodohexoxycarbonyl or dodecafluorohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl) aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di($C_1$–$C_6$-alkyl)aminocarbonyl: di($C_1$–$C_4$-alkyl)aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N—(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl) aminocarbonyl, N-methyl-N-(1,1,2-trimethylpropyl)aminocarbonyl, N-methyl-N-(1,2,2-trimethylpropyl) aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl) aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl) aminocarbonyl, N-ethyl-N-(1-methylpentyl) aminocarbonyl, N-ethyl-N-(2-methylpentyl) aminocarbonyl, N-ethyl-N-(3-methylpentyl) aminocarbonyl, N-ethyl-N-(4-methylpentyl) aminocarbonyl, N-ethyl-N-(1,1-dimethylbutyl) aminocarbonyl, N-ethyl-N-(1,2-dimethylbutyl) aminocarbonyl, N-ethyl-N-(1,3-dimethylbutyl) aminocarbonyl, N-ethyl-N-(2,2-dimethylbutyl) aminocarbonyl, N-ethyl-N-(2,3-dimethylbutyl) aminocarbonyl, N-ethyl-N-(3,3-dimethylbutyl)-aminocarbonyl, N-ethyl-N-(1-ethylbutyl) aminocarbonyl, N-ethyl-N-(2-ethylbutyl) aminocarbonyl, N-ethyl-N-(1,1,2-trimethylpropyl) aminocarbonyl, N-ethyl-N-(1,2,2-trimethylpropyl) aminocarbonyl, N-ethyl-N-(1-ethyl-1-methylpropyl) aminocarbonyl, N-ethyl-N-(1-ethyl-2-methylpropyl) aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$–$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl) aminothiocarbonyl, N,N-di(2-methylpropyl) aminothiocarbonyl, N,N-di(1,1-dimethylethyl) aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl) aminothiocarbonyl, N-ethyl-N-(2-methylpropyl) aminothiocarbonyl, N-ethyl-N-(1,1-dimethylethyl) aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl) aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl) aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2- methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_4$-alkoxy-$C_1$–$C_4$-alkyl and the alkoxyalkyl moieties of hydroxy-$C_1$–$C_4$-alkoxy-$C_1$–$C_4$-alkyl: $C_1$–$C_4$-alkyl, which is substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy) butyl, 2-(butoxy)butyl, 2-(1-methylpropoxy)butyl, 2-(2-methylpropoxy)butyl, 2-(1,1-dimethylethoxy) butyl, 3-(methoxy)butyl, 3-(ethoxy)butyl, 3-(propoxy) butyl, 3-(1-methylethoxy)butyl, 3-(butoxy)butyl, 3-(1-methylpropoxy)butyl, 3-(2-methylpropoxy)butyl, 3-(1, 1-dimethylethoxy)butyl, 4-(methoxy)butyl, 4-(ethoxy) butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_4$-alkoxy-$C_1$–$C_4$-alkoxy as alkoxyalkoxy moieties of $C_1$–$C_4$-alkoxy-$C_1$–$C_4$-alkoxycarbonyl: $C_1$–$C_4$-alkoxy which is substituted by $C_1$–$C_4$-alkoxy as mentioned above, i.e., for example, methoxymethoxy, ethoxymethoxy, propoxymethoxy, (1-methylethoxy) methoxy, butoxymethoxy, (1-methylpropoxy)methoxy, (2-methylpropoxy)methoxy, (1,1-dimethylethoxy) methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy) propoxy, 2-(1-methylethoxy)propoxy, 2-(butoxy) propoxy, 2-(1-methylpropoxy)propoxy, 2-(2-methylpropoxy)propoxy, 2-(1,1-dimethylethoxy) propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy) propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy) butoxy, 3-(1-methylethoxy)butoxy, 3-(butoxy)butoxy, 3-(1-methylpropoxy)butoxy, 3-(2-methylpropoxy) butoxy, 3-(1,1-dimethylethoxy)butoxy, 4-(methoxy) butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N—($C_3$–$C_6$-alkenyl)-N—($C_1$–$C_6$)alkylaminocarbonyl [sic] and N—($C_3$–$C_6$-alkenyl)-N—($C_1$–$C_6$-alkoxy) aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moiety of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N—($C_3$–$C_6$-alkynyl)-N—($C_1$–$C_6$-alkyl)aminocarbonyl and N—($C_3$–$C_6$-alkynyl)-N—($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e. for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and the heterocyclyl moieties of heterocyclylcarbonyl, heterocyclyl-$C_1$–$C_6$-alkyl, heterocyclyloxycarbonyl, heterocyclyloxythiocarbonyl, heterocyclyl-$C_2$–$C_6$-alkenylcarbonyl, heterocyclylcarbonyl-$C_1$–$C_6$-alkyl, N—($C_1$–$C_6$-alkyl)-N-(heterocyclyl)aminocarbonyl, heterocyclylaminocarbonyl: a saturated, partially saturated or unsaturated 5- or 6-membered, C-bonded heterocyclic ring containing one to four identical or different heteroatoms selected from the following group: oxygen, sulfur or nitrogen, i.e., for example, 5-membered rings having, for example, one heteroatom, having two heteroatoms, having three heteroatoms or having four heteroatoms or, for example, 6-membered rings having, for example, one heteroatom, having two heteroatoms, having three heteroatoms or having four heteroatoms, i.e. 5-membered rings having one heteroatom such as:
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl or pyrrol-3-yl;

5-membered rings having two heteroatoms such as:
tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-Oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-Dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl or thiazol-5-yl;

5-membered rings having three heteroatoms such as:
1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,3-$\Delta^2$-thiadiazolin-4-yl, 1,2,3-$\Delta^2$-thiadiazolin-5-yl, 1,2,4-$\Delta^4$-thiadiazolin-3-yl, 1,2,4-Δ⁴-thiadiazolin-5-yl, 1,2,4-Δ³-thiadiazolin-3-yl, 1,2,4-Δ³-thiadiazolin-5-yl, 1,2,4-Δ²-thiadiazolin-3-yl, 1,2,4-Δ²-thiadiazolin-5-yl, 1,3,4-Δ²-thiadiazolin-2-yl, 1,3,4-Δ²-thiadiazolin-5-yl, 1,3,4-Δ³-thiadiazolin-2-yl, 1,3,4-thiadiazolin-2-yl, 1,3,2-dioxathiolan-4-yl, 1,2,3-Δ²-triazolin-4-yl, 1,2,3-Δ²-triazolin-5-yl, 1,2,4-Δ²-triazolin-3-yl, 1,2,4-Δ²-triazolin-5-yl, 1,2,4-Δ³-triazolin-3-yl, 1,2,4-Δ³-triazolin-5-yl, 1,2,4-Δ¹-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl or 1,2,4-triazol-3-yl;

5-membered rings having four heteroatoms such as: tetrazol-5-yl;

6-membered rings having one heteroatom such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl or pyridin-4-yl;

6-membered rings having two heteroatoms such as:
1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3- yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl, pyridazin-3-yl, pyridazin-4-yl, pyrimidin-2-yl, pyrimidin-4-yl, pyrimidin-5-yl or pyrazin-2-yl;

6-membered rings having three heteroatoms such as:
1,3,5-triazin-2-yl, 1,2,4-triazin-3-yl, 1,2,4-triazin-5-yl, 1,2,4-triazin-6-yl;

6-membered rings having four heteroatoms such as:
1,2,4,5-tetrazin-3-yl;
where, if appropriate, the sulfur of the heterocycles mentioned may be oxidized to S=O or S(=O)$_2$
and where a bicyclic ring system may be formed with a fused-on phenyl ring or with a $C_3$–$C_6$-carbocycle or with a further 5- to 6-membered heterocycle;

N-bonded heterocyclyl: a saturated, partially saturated or unsaturated 5- or 6-membered N-bonded heterocyclic ring which contains at least one nitrogen and optionally one to three identical or different heteroatoms selected from the following group: oxygen, sulfur or nitrogen, i.e., for example, N-bonded 5-membered rings such as:
tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

and N-bonded 6-membered rings such as:
piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and also N-bonded cyclic imides such as:
phthalimide, tetrahydrophthalimide, succinimide, maleinimide, glutarimide, 5-oxotriazolin-1-yl, 5-oxo-1,3,4-oxadiazolin-4-yl or 2,4-dioxo-(1H,3H)-pyrimidin-3-yl;

where a bicyclic ring system may be formed with a fused-on phenyl ring or with a $C_3$–$C_6$-carbocycle or a further 5- to 6-membered heterocycle.

All phenyl rings or heterocyclyl radicals and all phenyl components in phenyl-$C_1$–$C_6$-alkyl, phenylcarbonyl-$C_1$–$C_6$-alkyl, phenylcarbonyl, phenylalkenylcarbonyl, phenoxycarbonyl, phenyloxythiocarbonyl, phenylaminocarbonyl and N—($C_1$–$C_6$-alkyl)-N-phenylaminocarbonyl or heterocyclyl components in heterocyclyl-$C_1$–$C_6$-alkyl, heterocyclylcarbonyl-$C_1$–$C_6$-alkyl, heterocyclylcarbonyl, heterocyclyloxythiocarbonyl, heterocyclylalkenylcarbonyl, heterocyclyloxycarbonyl, heterocyclylaminocarbonyl and N—($C_1$–$C_6$-alkyl)-N-heterocyclylaminocarbonyl are, unless stated otherwise, preferably unsubstituted or carry one to three halogen atoms and/or one nitro group, one cyano radical and/or one or two methyl, trifluoromethyl, methoxy or trifluoromethoxy substituents.

Furthermore, the expression "Y together with the two carbons to which it is attached forms a saturated, partially saturated or unsaturated heterocycle which contains one to three identical or different heteroatoms selected from the following group: oxygen, sulfur or nitrogen" represents, for example, 5-membered rings having one heteroatom, such as:
tetrahydrofurandiyl, tetrahydrothienediyl, tetrahydropyrroldiyl, dihydrofurandiyl, dihydrothienediyl, dihydropyrroldiyl, furandiyl, thienediyl or pyrroldiyl;

or 5-membered rings having two heteroatoms, such as:
tetrahydropyrazoldiyl, tetrahydroisoxazoldiyl, 1,2-oxathiolanediyl, tetrahydroisothiazoldiyl, 1,2-dithiolanediyl, tetrahydroimidazoldiyl, tetrahydrooxazoldiyl, tetrahydrothiazoldiyl, 1,3-dioxolanediyl, 1,3-oxathiolanediyl, dihydropyrazoldiyl, dihydroisoxazoldiyl, dihydroisothiazoldiyl, 1,2-dithioldiyl, dihydroimidazoldiyl, dihydrooxazoldiyl, dihydrothiazoldiyl, dioxoldiyl, oxathioldiyl, pyrazoldiyl, isoxazoldiyl, isothiazoldiyl, imidazoldiyl, oxazoldiyl or thiazoldiyl;

or 5-membered rings having three heteroatoms, such as:
1,2,3-oxadiazolinediyl, 1,2,3-thiadiazolinediyl, 1,2,3-triazolinediyl, 1,2,3-oxadiazoldiyl, 1,2,3-thiadiazoldiyl or 1,2,3-triazoldiyl;

or 6-membered rings having one heteroatom, such as:
tetrahydropyrandiyl, piperidinediyl, tetrahydrothiopyrandiyl, dihydropyrandiyl, dihydrothiopyrandiyl, tetrahydropyrindinediyl [sic], pyrandiyl, thiopyrandiyl, dihydropyrinediyl [sic] or pyridinediyl;
or 6-membered rings having two heteroatoms, such as:
1,3-dioxanediyl, 1,4-dioxanediyl, 1,3-dithianediyl, 1,4-dithianediyl, 1,3-oxathianediyl, 1,4-oxathianediyl, 1,2-dithianediyl, hexahydropyrimidinediyl, hexahydropyrazinediyl, hexahydropyridazinediyl, tetrahydro-1,3-oxazinediyl, tetrahydro-1,3-thiazinediyl, tetrahydro-1,4-oxazinediyl, tetrahydro-1,2-oxazinediyl, dihydro-1,2-oxazinediyl, dihydro-1,2-thiazinediyl, tetrahydropyridazinediyl, dihydro-1,3-oxazinediyl, dihydro-1,3-oxazinediyl, dihydro-1,3-thiazinediyl, tetrahydropyrimidinediyl, tetrahydropyrazinediyl, dihydro-1,4-thiazinediyl, dihydro-1,4-oxazinediyl, dihydro-1,4-dioxinediyl, dihydro-1,4-dithiinediyl, 1,2-oxazinediyl, 1,2-thiazinediyl, 1,3-oxazinediyl, 1,3-thiazinediyl, 1,4-oxazinediyl, 1,4-thiazinediyl, dihydropyridazinediyl, dihydropyrazinediyl, dihydropyrimidinediyl, pyridazinediyl, pyrimidinediyl or pyrazinediyl;
or 6-membered rings having 3 heteroatoms, such as:
1,2,4-triazinediyl;
where, if appropriate, the sulfur of the heterocycles mentioned may be oxidized to S=O or S(=O)$_2$;
and where the radical is fused to the skeleton via two adjacent carbons.

The compounds of the formula I according to the invention where $R^9$=IIa are referred to as compounds of the formula Ia, and compounds of the formula I where $R^9$=IIb are referred to as Ib.

With respect to the use of the compounds of the formula I according to the invention as herbicides, the variables preferably have the following meanings, in each case on their own or in combination:

X is oxygen, sulfur, S=O, S(=O)$_2$, $CR^6R^7$, $NR^8$ or a bond;

Y together with the two carbons to which it is attached forms a saturated, partially saturated or unsaturated 5- or 6-membered heterocycle which contains one to two identical or different heteroatoms selected from the following group: oxygen, sulfur or nitrogen;

$R^1, R^2$ are hydrogen or $C_1$–$C_6$-alkyl;

$R^3$ is halogen, $C_1$–$C_6$-alkyl or $C_1$–$C_6$-alkoxy;

$R^4$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)aminosulfonyl, N,N-di-($C_1$–$C_6$-alkyl)aminosulfonyl, N—( ($C_1$–$C_6$-alkylsulfonyl)amino [sic], N—($C_1$–$C_6$-haloalkylsulfony)amino [sic], N—($C_1$–$C_6$-alkyl)-N—($C_1$–$C_6$-alkylsulfonyl)amino or N—($C_1$–$C_6$-alkyl)-N—($C_1$–$C_6$-haloalkylsulfonyl)amino; in particular nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl or $C_1$–$C_6$-haloalkylsulfonyl;

$R^5$ is hydrogen;

$R^6, R^7$ are hydrogen or $C_1$–$C_6$-alkyl;

$R^8$ is $C_1$–$C_6$-alkyl, $C_1$–$C_6$-alkylcarbonyl or $C_1$–$C_6$-alkylsulfonyl;

m is 0, 1 or 2;

$R^9$ is a radical IIa

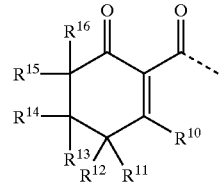

where
$R^{10}$ is hydroxyl, mercapto, halogen, $OR^{17}$, $SR^{17}$, $SO_2R^{18}$, $OSO_2R^{18}$, $NR^{19}R^{20}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{11}, R^{15}$ are hydrogen or $C_1$–$C_4$-alkyl, such as methyl, ethyl or propyl; preferably hydrogen or methyl;

$R^{12}, R^{14}, R^{16}$ are hydrogen or $C_1$–$C_4$-alkyl, such as methyl, ethyl or propyl; preferably hydrogen or methyl;

$R^{13}$ is hydrogen, hydroxyl, $C_1$–$C_6$-alkyl, di-($C_1$–$C_6$-alkoxy)methyl, ($C_1$–$C_6$-alkoxy)-($C_1$–$C_6$-alkylthio)methyl, di-($C_1$–$C_6$-alkylthio)methyl, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;
is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last-mentioned radicals may be substituted by one to three $C_1$–$C_4$-alkyl radicals;
is preferably hydrogen, hydroxyl or $C_1$–$C_4$-alkyl, such as methyl, ethyl or propyl; or $R^{12}$ and $R^{13}$ or $R^{13}$ and $R^{16}$ together form a πbond or a $C_3$–$C_5$-alkyl chain which may carry one to three radicals from the following group: halogen, cyano, $C_1$–$C_4$-alkyl, $C_1$–$C_4$-haloalkyl or $C_1$–$C_4$-alkoxycarbonyl; or $R^{11}$ and $R^{16}$ together form a $C_1$–$C_4$-alkyl chain which may carry one to three radicals from the following group: halogen, cyano, $C_1$–$C_4$-alkyl, $C_1$–$C_4$-haloalkyl or $C_1$–$C_4$-alkoxycarbonyl; or $R^{13}$ and $R^{14}$ together form a —O—$(CH_2)_p$—O—, —O—$(CH_2)_p$—S— or —S—$(CH_2)_p$—S— chain which may be substituted by one to three radicals from the following group: halogen, cyano, $C_1$–$C_4$-alkyl, $C_1$–$C_4$-haloalkyl or $C_1$–$C_4$-alkoxycarbonyl;

$R^{13}$ and $R^{14}$ together preferably form a —O—$(CH_2)_p$—O—, —O—$(CH_2)_p$—S— or —S—$(CH_2)_p$—S— chain which may be substituted by one to three radicals from the following groups: $C_1$–$C_4$-alkyl or $C_1$–$C_4$-alkoxycarbonyl; or $R^{13}$ and $R^{14}$ together with carbon to which they are attached form a carbonyl group;

$R^{17}$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N—($C_3$–$C_6$-alkenyl)-N—($C_1$–$C_6$-alkyl)aminocarbonyl, N—($C_3$–$C_6$-alkynyl)-N—($C_1$–$C_6$- alkyl)aminocarbonyl, N—($C_1$–$C_6$-alkoxy)-N—($C_1$–$C_6$-alkyl)aminocarbonyl, N—($C_{3-C6}$-alkenyl)-N—($C_1$–$C_6$-alkoxy)aminocarbonyl, N—($C_3$–$C_6$-alkynyl)-N—($C_1$–$C_6$-alkoxy)aminocarbonyl, di-($C_1$–$C_6$-alkyl)aminothiocarbonyl, $C_1$–$C_6$-alkoxyimino-$C_1$–$C_6$-alkyl, where the alkyl, cycloalkyl or alkoxy radicals mentioned may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, hydroxycarbonyl, $C_1$–$C_4$-alkylaminocarbonyl, di-($C_1$–$C_4$-alkyl)aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl or heterocyclyl-$C_1$–$C_6$-alkenylcarbonyl, where the phenyl or the heterocyclyl radical of the 14 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

is preferably $C_1$–$C_6$-alkyl, $C_3$–$C_6$-alkenyl, $C_3$–$C_6$-alkynyl, $C_1$–$C_6$-alkylcarbonyl, $C_1$–$C_6$-alkoxycarbonyl, $C_1$–$C_6$-alkylaminocarbonyl or N,N-di($C_1$–$C_6$-alkyl)aminocarbonyl, where the alkyl or alkoxy radicals mentioned may be partially or fully halogenated and/or may carry one to three of the following groups: cyano, $C_1$–$C_4$-alkoxy, $C_1$–$C_4$-alkylthio or $C_1$–$C_4$-alkoxycarbonyl;

is phenyl, phenyl-$C_1$–$C_6$-alkyl, phenylcarbonyl-$C_1$–$C_6$-alkyl, phenylcarbonyl, phenoxycarbonyl, heterocyclyl-[sic], heterocyclyl-$C_1$–$C_6$-alkyl, heterocyclylcarbonyl-$C_1$–$C_6$-alkyl, heterocyclylcarbonyl or heterocyclyloxycarbonyl, where the phenyl or the heterocyclyl radical of the 10 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$ is $C_1$–$C_6$-alkyl, $C_3$–$C_6$-alkenyl or $C_3$–$C_6$-cycloalkyl, where the three radicals mentioned may be partially or fully halogenated and/or may carry one to three of the following groups: cyano, $C_1$–$C_4$-alkoxy, $C_1$–$C_4$-alkylthio, $C_1$–$C_4$-alkylcarbonyl or $C_1$–$C_4$-alkoxycarbonyl;

is phenyl, phenyl-$C_1$–$C_4$-alkyl, heterocyclyl or heterocyclyl-$C_1$–$C_4$-alkyl, where the phenyl or the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{19}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the alkyl, cycloalkyl or alkoxy radicals mentioned may be partially or fully halogenated and/or may carry one to three of the following radicals: cyano, $C_1$–$C_4$-alkoxycarbonyl, $C_1$–$C_4$-alkylaminocarbonyl, di-($C_1$–$C_4$-alkyl)aminocarbonyl or $C_3$–$C_6$-cycloalkyl;

is phenyl, phenyl-$C_1$–$C_4$-alkyl, phenylcarbonyl, heterocyclyl, heterocycly-$C_1$–$C_4$-alkyl [sic] or heterocyclylcarbonyl, where the phenyl or heterocyclyl radical of the six last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is $C_1$–$C_6$-alkyl or $C_3$–$C_6$-alkenyl;

p is 2, 3 or 4.

Particular preference is given to the compounds of the formula I where the variables have the meanings below, in each case on their own or in combination:

X is oxygen, sulfur, S=O, S(=O)$_2$, $CR^6R^7$ or a bond;

Y together with the two carbons to which it is attached forms the following heterocycles:

(in the diagrams of the heterocycles below, the upper wavy line in each case represents the linkage to the carbon which carries the radicals $R^1$ and $R^2$, and the lower wavy lines represents the linkage to the metacarbon of the benzoyl moiety).

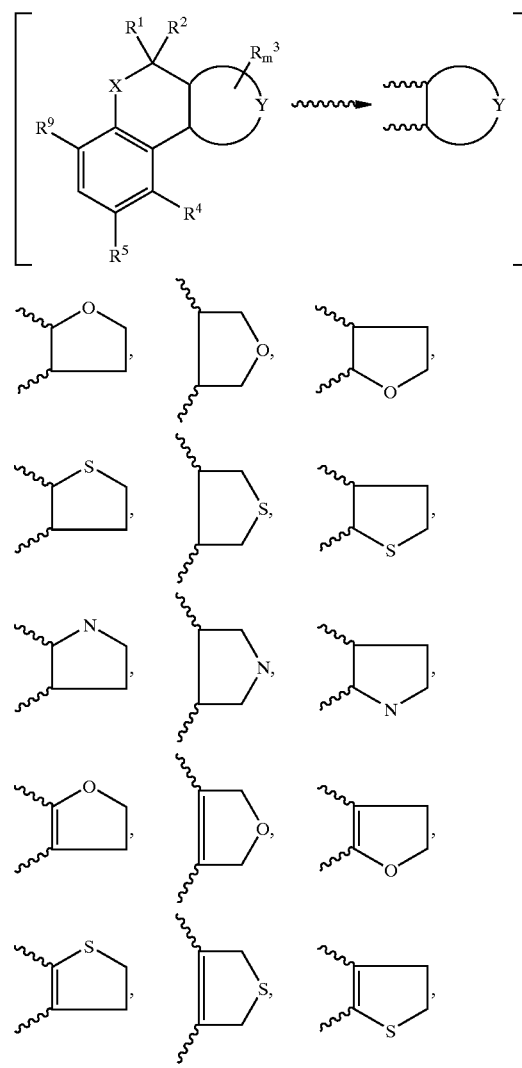

-continued
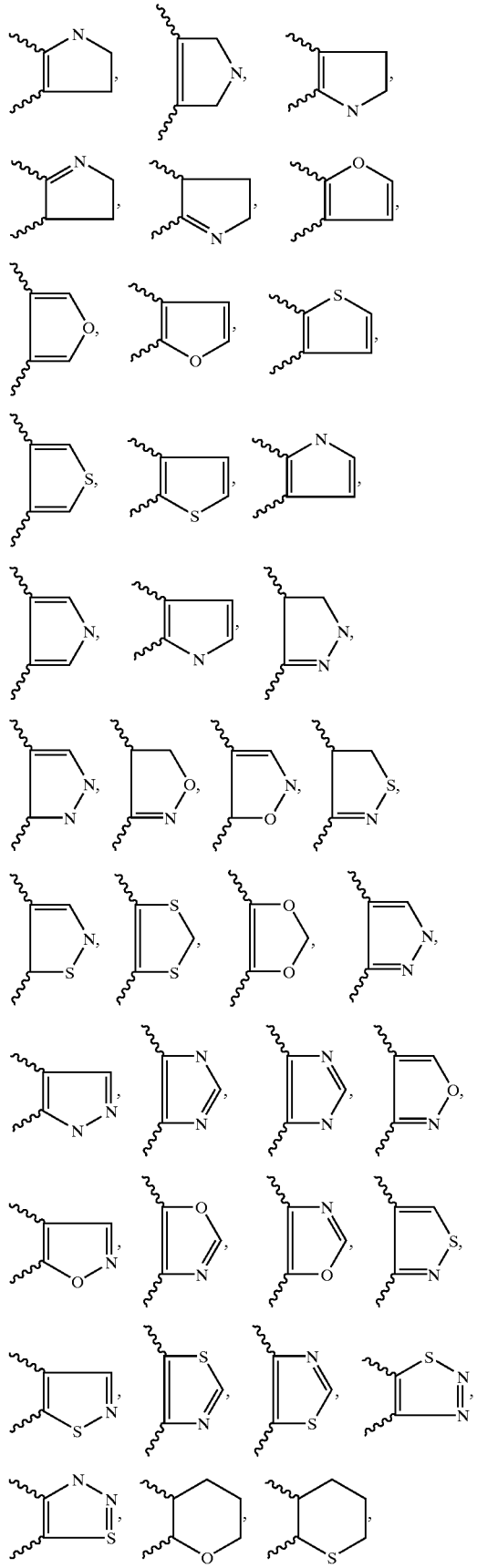
-continued
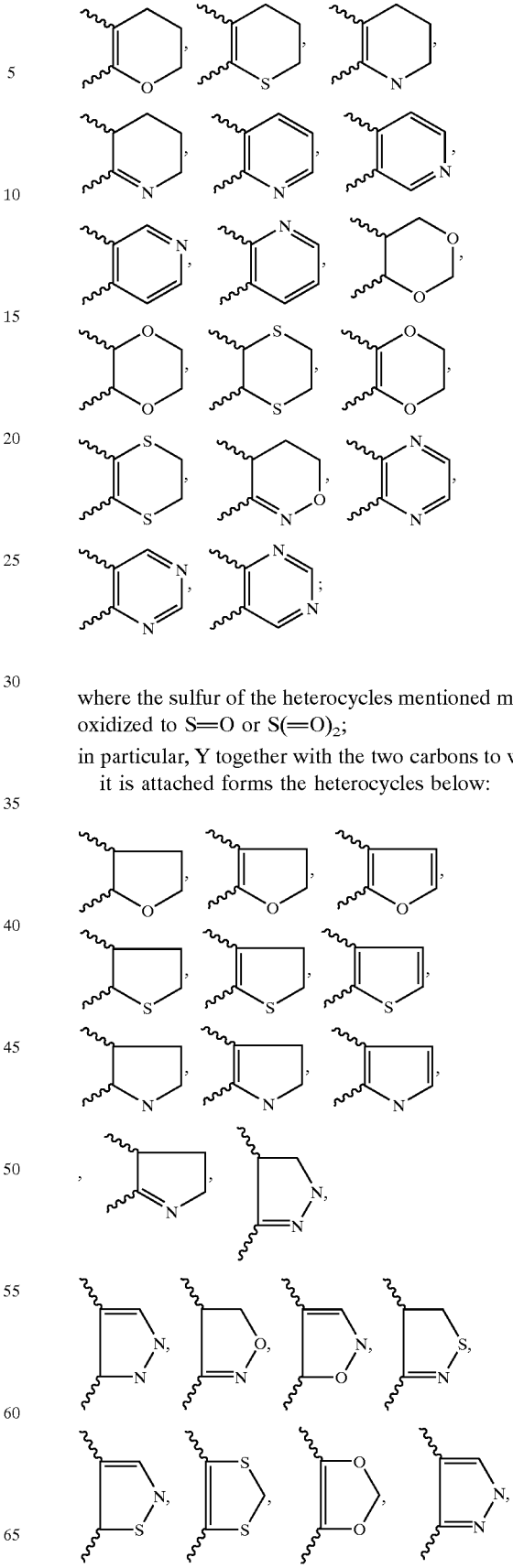
where the sulfur of the heterocycles mentioned may be oxidized to S=O or S(=O)$_2$;
in particular, Y together with the two carbons to which it is attached forms the heterocycles below:
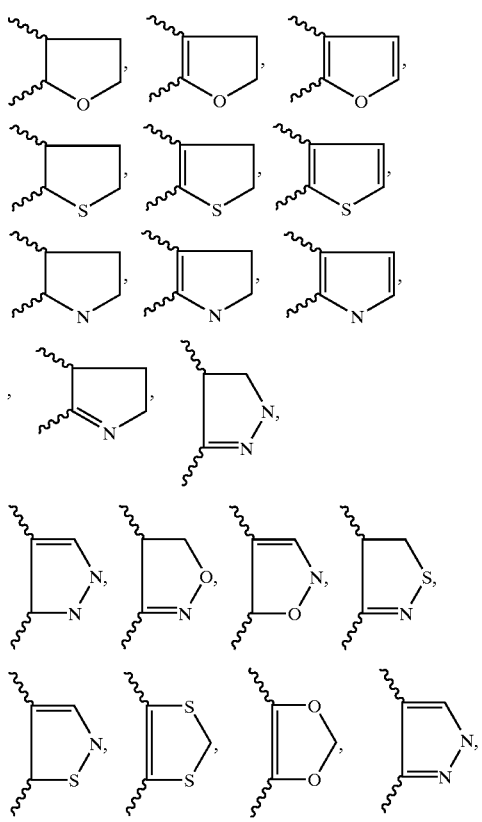

-continued

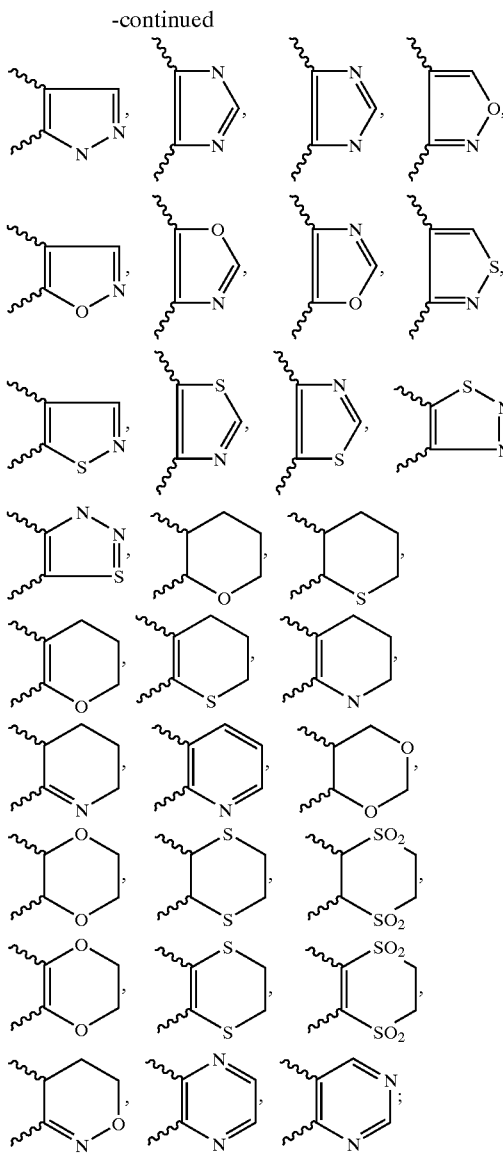

$R^1, R^2$ are hydrogen;
$R^3$ is $C_1-C_6$-alkyl, such as methyl, ethyl or n-propyl; in particular methyl;
$R^4$ is nitro, halogen, $C_1-C_6$-alkyl, $C_1-C_6$-haloalkyl, $C_1-C_6$-alkoxy, $C_1-C_6$-alkylthio or $C_1-C_6$-alkylsulfonyl; in particular nitro, halogen, such as fluorine, chlorine or bromine, $C_1-C_6$-haloalkyl such as trifluoromethyl, $C_1-C_6$-alkylthio such as methylthio or ethylthio or $C_1-C_6$-alkylsulfonyl, such as methylsulfonyl or ethylsulfonyl; particularly preferably nitro, chlorine, trifluoromethyl, methylthio or methylsulfonyl;
$R^5$ is hydrogen;
$R^6, R^7$ are hydrogen or $C_1-C_6$-alkyl, such as methyl or ethyl; in particular hydrogen or methyl;
m is 0, 1 or 2; in particular 0 or 1;
$R^9$ is a radical IIa
$R^{10}$ is hydroxyl, mercapto, $OR^{17}$, $SR^{17}$ or $NR^{19}R^{20}$
Particular preference is given to the compounds Ia where
X is oxygen, sulfur, $S(=O)_2$, $CH_2$ or a bond;
Y together with the two carbons to which it is attached forms the following heterocycles:

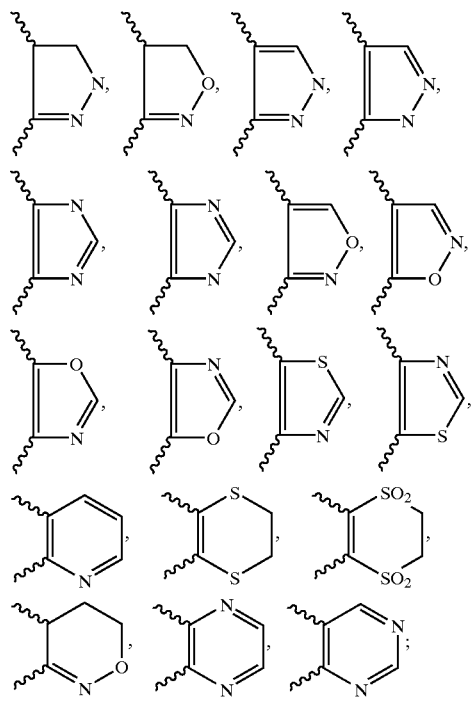

$R^1, R^2$ are hydrogen;
$R^3$ is $C_1-C_4$-alkyl;
$R^4$ is nitro, halogen, $C_1-C_6$-alkyl, $C_1-C_6$-haloalkyl, $C_1-C_6$-alkoxy, $C_1-C_6$-alkylthio or $C_1-C_6$-alkylsulfonyl;
$R^5$ is hydrogen or $C_1-C_6$-alkyl;
m is 0, 1 or 2.
Very particular preference is given to the compounds of the formula Ia, where
$R^{10}$ is hydroxyl.
Likewise, very particular preference is given to the compounds of the formula I where
$R^{10}$ is halogen, $OR^{17}$, $SR^{17}$, $SO_2R^{18}$, $OSO_2R^{18}$, $NR^{19}R^{20}$ or N-bonded heterocyclyl which may be partially or fully halogenated and/or may carry one to three of the following radicals: nitro, cyano, $C_1-C_4$-alkyl, $C_1-C_4$-haloalkyl, $C_1-C_4$-alkoxy or $C_1-C_4$-haloalkoxy.
Likewise, very particular preference is given to the compounds of the formula Ia where
$R^{11}$, $R^{15}$ are hydrogen or $C_1-C_4$-alkyl;
$R^{12}$, $R^{14}$, $R^{16}$ are hydrogen or $C_1-C_4$-alkyl;
$R^{13}$ is hydrogen, hydroxyl, $C_1-C_6$-alkyl, di-($C_1-C_6$-alkoxy)-methyl, ($C_1-C_6$-alkoxy)-($C_1-C_6$-alkylthio)methyl, di-($C_1-C_6$-alkylthio)methyl, $C_1-C_6$-alkylthio, $C_1-C_6$-haloalkylthio, $C_1-C_6$-alkylsulfonyl or $C_1-C_6$-haloalkylsulfonyl; in particular hydrogen, hydroxyl or $C_1-C_6$-alkyl; or
$R^{12}$ and $R^{16}$ together form a $C_1-C_4$-alkyl chain which may carry one to three radicals from the following group: halogen, $C_1-C_4$-alkyl or $C_1-C_4$-haloalkyl;
in particular, $R^{12}$ and $R^{16}$ together form a methylene bridge which may carry one or two radicals from the following group: halogen, $C_1-C_2$-alkyl or $C_1-C_2$-haloalkyl; or
$R^{13}$ and $R^{14}$ together with the carbons to which they are attached form a carbonyl group.

Likewise, very particular preference is given to the compounds of the formula I where

- $R^{11}$, $R^{15}$ are hydrogen or $C_1-C_4$-alkyl;
- $R^{12}$, $R^{14}$, $R^{16}$ are hydrogen or $C_1-C_4$-alkyl;
- $R^{13}$ is hydrogen, hydroxyl, $C_1-C_6$-alkyl, di-($C_1-C_6$-alkoxy)-methyl, ($C_1-C_6$-alkoxy)($C_1-C_6$-alkylthio)methyl, di-($C_1-C_6$-alkylthio)methyl, $C_1-C_6$-alkylthio, $C_1-C_6$-haloalkylthio, $C_1-C_6$-alkylsulfonyl or $C_1-C_6$-haloalkylsulfonyl; in particular hydrogen, hydroxyl or $C_1-C_6$-alkyl; or
- $R^{13}$ and $R^{14}$ together with the carbon to which they are attached form a carbonyl group.

Likewise, particular preference is given to the compounds of the formula I where $R^9$ has the following meaning:

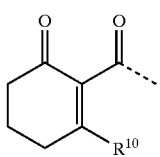
IIa1

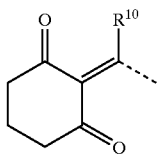
IIb1

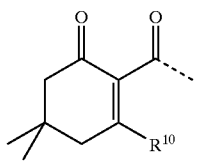
IIa2

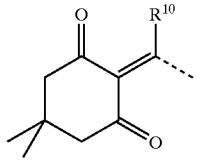
IIb2

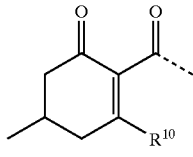
IIa3

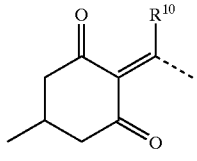
IIb3

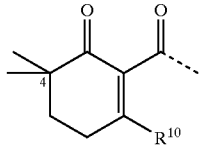
IIa4

-continued

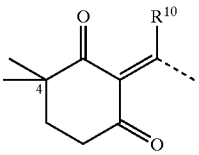
IIb4

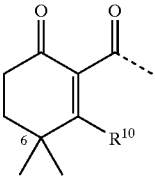
IIa5

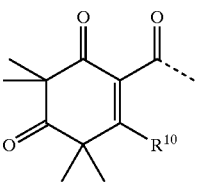
IIb5

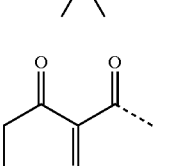
IIa6

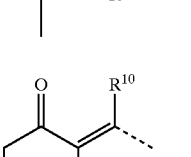
IIb6

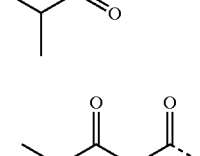
IIa7

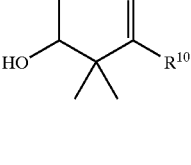
IIb7

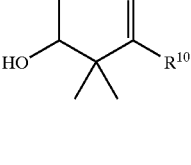
IIa8

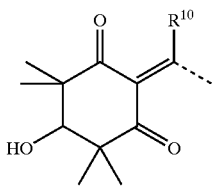

IIb8

Likewise, particular preference is given to the compounds of the formula Ia1 (=where $R^1$, $R^2$, $R^5$ and $R^{11}$ to $R^{16}$=H, m=O [sic], the heterocycle is as defined in the structural formula), in particular to the compounds Ia1.n where the variables X, $R^4$ and $R^{10}$ are as defined in Table 1.

The given radical definitions $R^1$ to $R^{16}$, X, Y and m and the meaning of the fused heterocycle are of particular importance for the compounds according to the invention not only in combination with one another, but also on their own.

(For reasons of a clearer presentation, the meaning of the fused heterocycles in each of the formulae Ia1, Ia2 . . . is in each case as stated in the corresponding structural formula.)

TABLE 1

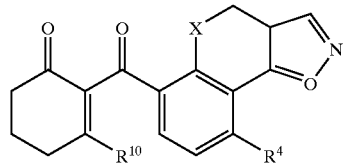

Ia1

| n | X | $R^4$ | $R^{10}$ |
|---|---|---|---|
| 1. | Bond | F | OH |
| 2. | Bond | Cl | OH |
| 3. | Bond | Br | OH |
| 4. | Bond | $NO_2$ | OH |
| 5. | Bond | $SCH_3$ | OH |
| 6. | Bond | $SO_2CH_3$ | OH |
| 7. | Bond | $SO_2CH_2CH_3$ | OH |
| 8. | Bond | $CH_3$ | OH |
| 9. | Bond | $CF_3$ | OH |
| 10. | Bond | $OCHF_2$ | OH |
| 11. | $CH_2$ | F | OH |
| 12. | $CH_2$ | Cl | OH |
| 13. | $CH_2$ | Br | OH |
| 14. | $CH_2$ | $NO_2$ | OH |
| 15. | $CH_2$ | $SCH_3$ | OH |
| 16. | $CH_2$ | $SO_2CH_3$ | OH |
| 17. | $CH_2$ | $SO_2CH_2CH_3$ | OH |
| 18. | $CH_2$ | $CH_3$ | OH |
| 19. | $CH_2$ | $CF_3$ | OH |
| 20. | $CH_2$ | $OCHF_2$ | OH |
| 21. | O | F | OH |
| 22. | O | Cl | OH |
| 23. | O | Br | OH |
| 24. | O | $NO_2$ | OH |
| 25. | O | $SCH_3$ | OH |
| 26. | O | $SO_2CH_3$ | OH |
| 27. | O | $SO_2CH_2CH_3$ | OH |
| 28. | O | $CH_3$ | OH |
| 29. | O | $CF_3$ | OH |
| 30. | O | $OCHF_2$ | OH |
| 31. | S | F | OH |
| 32. | S | Cl | OH |
| 33. | S | Br | OH |
| 34. | S | $NO_2$ | OH |
| 35. | S | $SCH_3$ | OH |
| 36. | S | $SO_2CH_3$ | OH |
| 37. | S | $SO_2CH_2CH_3$ | OH |
| 38. | S | $CH_3$ | OH |
| 39. | S | $CF_3$ | OH |
| 40. | S | $OCHF_2$ | OH |
| 41. | $SO_2$ | F | OH |
| 42. | $SO_2$ | Cl | OH |
| 43. | $SO_2$ | Br | OH |
| 44. | $SO_2$ | $NO_2$ | OH |
| 45. | $SO_2$ | $SCH_3$ | OH |
| 46. | $SO_2$ | $SO_2CH_3$ | OH |
| 47. | $SO_2$ | $SO_2CH_2CH_3$ | OH |
| 48. | $SO_2$ | $CH_3$ | OH |
| 49. | $SO_2$ | $CF_3$ | OH |
| 50. | $SO_2$ | $OCHF_2$ | OH |
| 51. | Bond | F | $OCOC_6H_5$ |
| 52. | Bond | Cl | $OCOC_6H_5$ |
| 53. | Bond | Br | $OCOC_6H_5$ |
| 54. | Bond | $NO_2$ | $OCOC_6H_5$ |
| 55. | Bond | $SCH_3$ | $OCOC_6H_5$ |
| 56. | Bond | $SO_2CH_3$ | $OCOC_6H_5$ |
| 57. | Bond | $SO_2CH_2CH_3$ | $OCOC_6H_5$ |
| 58. | Bond | $CH_3$ | $OCOC_6H_5$ |
| 59. | Bond | $CF_3$ | $OCOC_6H_5$ |
| 60. | Bond | $OCHF_2$ | $OCOC_6H_5$ |
| 61. | $CH_2$ | F | $OCOC_6H_5$ |
| 62. | $CH_2$ | Cl | $OCOC_6H_5$ |
| 63. | $CH_2$ | Br | $OCOC_6H_5$ |
| 64. | $CH_2$ | $NO_2$ | $OCOC_6H_5$ |
| 65. | $CH_2$ | $SCH_3$ | $OCOC_6H_5$ |
| 66. | $CH_2$ | $SO_2CH_3$ | $OCOC_6H_5$ |
| 67. | $CH_2$ | $SO_2CH_2CH_3$ | $OCOC_6H_5$ |
| 68. | $CH_2$ | $CH_3$ | $OCOC_6H_5$ |
| 69. | $CH_2$ | $CF_3$ | $OCOC_6H_5$ |
| 70. | $CH_2$ | $OCHF_2$ | $OCOC_6H_5$ |
| 71. | O | F | $OCOC_6H_5$ |
| 72. | O | Cl | $OCOC_6H_5$ |
| 73. | O | Br | $OCOC_6H_5$ |
| 74. | O | $NO_2$ | $OCOC_6H_5$ |
| 75. | O | $SCH_3$ | $OCOC_6H_5$ |
| 76. | O | $SO_2CH_3$ | $OCOC_6H_5$ |
| 77. | O | $SO_2CH_2CH_3$ | $OCOC_6H_5$ |
| 78. | O | $CH_3$ | $OCOC_6H_5$ |
| 79. | O | $CF_3$ | $OCOC_6H_5$ |
| 80. | O | $OCHF_2$ | $OCOC_6H_5$ |
| 81. | S | F | $OCOC_6H_5$ |
| 82. | S | Cl | $OCOC_6H_5$ |
| 83. | S | Br | $OCOC_6H_5$ |
| 84. | S | $NO_2$ | $OCOC_6H_5$ |
| 85. | S | $SCH_3$ | $OCOC_6H_5$ |
| 86. | S | $SO_2CH_3$ | $OCOC_6H_5$ |
| 87. | S | $SO_2CH_2CH_3$ | $OCOC_6H_5$ |
| 88. | S | $CH_3$ | $OCOC_6H_5$ |
| 89. | S | $CF_3$ | $OCOC_6H_5$ |
| 90. | S | $OCHF_2$ | $OCOC_6H_5$ |
| 91. | $SO_2$ | F | $OCOC_6H_5$ |
| 92. | $SO_2$ | Cl | $OCOC_6H_5$ |
| 93. | $SO_2$ | Br | $OCOC_6H_5$ |
| 94. | $SO_2$ | $NO_2$ | $OCOC_6H_5$ |
| 95. | $SO_2$ | $SCH_3$ | $OCOC_6H_5$ |
| 96. | $SO_2$ | $SO_2CH_3$ | $OCOC_6H_5$ |
| 97. | $SO_2$ | $SO_2CH_2CH_3$ | $OCOC_6H_5$ |
| 98. | $SO_2$ | $CH_3$ | $OCOC_6H_5$ |
| 99. | $SO_2$ | $CF_3$ | $OCOC_6H_5$ |
| 100. | $SO_2$ | $OCHF_2$ | $OCOC_6H_5$ |
| 101. | Bond | F | $OCOC(CH_3)_3$ |
| 102. | Bond | Cl | $OCOC(CH_3)_3$ |
| 103. | Bond | Br | $OCOC(CH_3)_3$ |
| 104. | Bond | $NO_2$ | $OCOC(CH_3)_3$ |
| 105. | Bond | $SCH_3$ | $OCOC(CH_3)_3$ |

TABLE 1-continued

Ia1

| n | X | R$^4$ | R$^{10}$ |
|---|---|---|---|
| 106. | Bond | SO$_2$CH$_3$ | OCOC(CH$_3$)$_3$ |
| 107. | Bond | SO$_2$CH$_2$CH$_3$ | OCOC(CH$_3$)$_3$ |
| 108. | Bond | CH$_3$ | OCOC(CH$_3$)$_3$ |
| 109. | Bond | CF$_3$ | OCOC(CH$_3$)$_3$ |
| 110. | Bond | OCHF$_2$ | OCOC(CH$_3$)$_3$ |
| 111. | CH$_2$ | F | OCOC(CH$_3$)$_3$ |
| 112. | CH$_2$ | Cl | OCOC(CH$_3$)$_3$ |
| 113. | CH$_2$ | Br | OCOC(CH$_3$)$_3$ |
| 114. | CH$_2$ | NO$_2$ | OCOC(CH$_3$)$_3$ |
| 115. | CH$_2$ | SCH$_3$ | OCOC(CH$_3$)$_3$ |
| 116. | CH$_2$ | SO$_2$CH$_3$ | OCOC(CH$_3$)$_3$ |
| 117. | CH$_2$ | SO$_2$CH$_2$CH$_3$ | OCOC(CH$_3$)$_3$ |
| 118. | CH$_2$ | CH$_3$ | OCOC(CH$_3$)$_3$ |
| 119. | CH$_2$ | CF$_3$ | OCOC(CH$_3$)$_3$ |
| 120. | CH$_2$ | OCHF$_2$ | OCOC(CH$_3$)$_3$ |
| 121. | O | F | OCOC(CH$_3$)$_3$ |
| 122. | O | Cl | OCOC(CH$_3$)$_3$ |
| 123. | O | Br | OCOC(CH$_3$)$_3$ |
| 124. | O | NO$_2$ | OCOC(CH$_3$)$_3$ |
| 125. | O | SCH$_3$ | OCOC(CH$_3$)$_3$ |
| 126. | O | SO$_2$CH$_3$ | OCOC(CH$_3$)$_3$ |
| 127. | O | SO$_2$CH$_2$CH$_3$ | OCOC(CH$_3$)$_3$ |
| 128. | O | CH$_3$ | OCOC(CH$_3$)$_3$ |
| 129. | O | CF$_3$ | OCOC(CH$_3$)$_3$ |
| 130. | O | OCHF$_2$ | OCOC(CH$_3$)$_3$ |
| 131. | S | F | OCOC(CH$_3$)$_3$ |
| 132. | S | Cl | OCOC(CH$_3$)$_3$ |
| 133. | S | Br | OCOC(CH$_3$)$_3$ |
| 134. | S | NO$_2$ | OCOC(CH$_3$)$_3$ |
| 135. | S | SCH$_3$ | OCOC(CH$_3$)$_3$ |
| 136. | S | SO$_2$CH$_3$ | OCOC(CH$_3$)$_3$ |
| 137. | S | SO$_2$CH$_2$CH$_3$ | OCOC(CH$_3$)$_3$ |
| 138. | S | CH$_3$ | OCOC(CH$_3$)$_3$ |
| 139. | S | CF$_3$ | OCOC(CH$_3$)$_3$ |
| 140. | S | OCHF$_2$ | OCOC(CH$_3$)$_3$ |
| 141. | SO$_2$ | F | OCOC(CH$_3$)$_3$ |
| 142. | SO$_2$ | Cl | OCOC(CH$_3$)$_3$ |
| 143. | SO$_2$ | Br | OCOC(CH$_3$)$_3$ |
| 144. | SO$_2$ | NO$_2$ | OCOC(CH$_3$)$_3$ |
| 145. | SO$_2$ | SCH$_3$ | OCOC(CH$_3$)$_3$ |
| 146. | SO$_2$ | SO$_2$CH$_3$ | OCOC(CH$_3$)$_3$ |
| 147. | SO$_2$ | SO$_2$CH$_2$CH$_3$ | OCOC(CH$_3$)$_3$ |
| 148. | SO$_2$ | CH$_3$ | OCOC(CH$_3$)$_3$ |
| 149. | SO$_2$ | CF$_3$ | OCOC(CH$_3$)$_3$ |
| 150. | SO$_2$ | OCHF$_2$ | OCOC(CH$_3$)$_3$ |
| 151. | Bond | F | OCOSCH$_3$ |
| 152. | Bond | Cl | OCOSCH$_3$ |
| 153. | Bond | Br | OCOSCH$_3$ |
| 154. | Bond | NO$_2$ | OCOSCH$_3$ |
| 155. | Bond | SCH$_3$ | OCOSCH$_3$ |
| 156. | Bond | SO$_2$CH$_3$ | OCOSCH$_3$ |
| 157. | Bond | SO$_2$CH$_2$CH$_3$ | OCOSCH$_3$ |
| 158. | Bond | CH$_3$ | OCOSCH$_3$ |
| 159. | Bond | CF$_3$ | OCOSCH$_3$ |
| 160. | Bond | OCHF$_2$ | OCOSCH$_3$ |
| 161. | CH$_2$ | F | OCOSCH$_3$ |
| 162. | CH$_2$ | Cl | OCOSCH$_3$ |
| 163. | CH$_2$ | Br | OCOSCH$_3$ |
| 164. | CH$_2$ | NO$_2$ | OCOSCH$_3$ |
| 165. | CH$_2$ | SCH$_3$ | OCOSCH$_3$ |
| 166. | CH$_2$ | SO$_2$CH$_3$ | OCOSCH$_3$ |
| 167. | CH$_2$ | SO$_2$CH$_2$CH$_3$ | OCOSCH$_3$ |
| 168. | CH$_2$ | CH$_3$ | OCOSCH$_3$ |
| 169. | CH$_2$ | CF$_3$ | OCOSCH$_3$ |
| 170. | CH$_2$ | OCHF$_2$ | OCOSCH$_3$ |
| 171. | O | F | OCOSCH$_3$ |
| 172. | O | Cl | OCOSCH$_3$ |
| 173. | O | Br | OCOSCH$_3$ |
| 174. | O | NO$_2$ | OCOSCH$_3$ |
| 175. | O | SCH$_3$ | OCOSCH$_3$ |
| 176. | O | SO$_2$CH$_3$ | OCOSCH$_3$ |
| 177. | O | SO$_2$CH$_2$CH$_3$ | OCOSCH$_3$ |
| 178. | O | CH$_3$ | OCOSCH$_3$ |
| 179. | O | CF$_3$ | OCOSCH$_3$ |
| 180. | O | OCHF$_2$ | OCOSCH$_3$ |
| 181. | S | F | OCOSCH$_3$ |
| 182. | S | Cl | OCOSCH$_3$ |
| 183. | S | Br | OCOSCH$_3$ |
| 184. | S | NO$_2$ | OCOSCH$_3$ |
| 185. | S | SCH$_3$ | OCOSCH$_3$ |
| 186. | S | SO$_2$CH$_3$ | OCOSCH$_3$ |
| 187. | S | SO$_2$CH$_2$CH$_3$ | OCOSCH$_3$ |
| 188. | S | CH$_3$ | OCOSCH$_3$ |
| 189. | S | CF$_3$ | OCOSCH$_3$ |
| 190. | S | OCHF$_2$ | OCOSCH$_3$ |
| 191. | SO$_2$ | F | OCOSCH$_3$ |
| 192. | SO$_2$ | Cl | OCOSCH$_3$ |
| 193. | SO$_2$ | Br | OCOSCH$_3$ |
| 194. | SO$_2$ | NO$_2$ | OCOSCH$_3$ |
| 195. | SO$_2$ | SCH$_3$ | OCOSCH$_3$ |
| 196. | SO$_2$ | SO$_2$CH$_3$ | OCOSCH$_3$ |
| 197. | SO$_2$ | SO$_2$CH$_2$CH$_3$ | OCOSCH$_3$ |
| 198. | SO$_2$ | CH$_3$ | OCOSCH$_3$ |
| 199. | SO$_2$ | CF$_3$ | OCOSCH$_3$ |
| 200. | SO$_2$ | OCHF$_2$ | OCOSCH$_3$ |
| 201. | Bond | F | OCH$_3$ |
| 202. | Bond | Cl | OCH$_3$ |
| 203. | Bond | Br | OCH$_3$ |
| 204. | Bond | NO$_2$ | OCH$_3$ |
| 205. | Bond | SCH$_3$ | OCH$_3$ |
| 206. | Bond | SO$_2$CH$_3$ | OCH$_3$ |
| 207. | Bond | SO$_2$CH$_2$CH$_3$ | OCH$_3$ |
| 208. | Bond | CH$_3$ | OCH$_3$ |
| 209. | Bond | CF$_3$ | OCH$_3$ |
| 210. | Bond | OCHF$_2$ | OCH$_3$ |
| 211. | CH$_2$ | F | OCH$_3$ |
| 212. | CH$_2$ | Cl | OCH$_3$ |
| 213. | CH$_2$ | Br | OCH$_3$ |
| 214. | CH$_2$ | NO$_2$ | OCH$_3$ |
| 215. | CH$_2$ | SCH$_3$ | OCH$_3$ |
| 216. | CH$_2$ | SO$_2$CH$_3$ | OCH$_3$ |
| 217. | CH$_2$ | SO$_2$CH$_2$CH$_3$ | OCH$_3$ |
| 218. | CH$_2$ | CH$_3$ | OCH$_3$ |
| 219. | CH$_2$ | CF$_3$ | OCH$_3$ |
| 220. | CH$_2$ | OCHF$_2$ | OCH$_3$ |
| 221. | O | F | OCH$_3$ |
| 222. | O | Cl | OCH$_3$ |
| 223. | O | Br | OCH$_3$ |
| 224. | O | NO$_2$ | OCH$_3$ |
| 225. | O | SCH$_3$ | OCH$_3$ |
| 226. | O | SO$_2$CH$_3$ | OCH$_3$ |
| 227. | O | SO$_2$CH$_2$CH$_3$ | OCH$_3$ |
| 228. | O | CH$_3$ | OCH$_3$ |
| 229. | O | CF$_3$ | OCH$_3$ |
| 230. | O | OCHF$_2$ | OCH$_3$ |
| 231. | S | F | OCH$_3$ |
| 232. | S | Cl | OCH$_3$ |
| 233. | S | Br | OCH$_3$ |
| 234. | S | NO$_2$ | OCH$_3$ |
| 235. | S | SCH$_3$ | OCH$_3$ |
| 236. | S | SO$_2$CH$_3$ | OCH$_3$ |
| 237. | S | SO$_2$CH$_2$CH$_3$ | OCH$_3$ |
| 238. | S | CH$_3$ | OCH$_3$ |
| 239. | S | CF$_3$ | OCH$_3$ |

TABLE 1-continued

Ia1

| n | X | R⁴ | R¹⁰ |
|---|---|---|---|
| 240. | S | OCHF₂ | OCH₃ |
| 241. | SO₂ | F | OCH₃ |
| 242. | SO₂ | Cl | OCH₃ |
| 243. | SO₂ | Br | OCH₃ |
| 244. | SO₂ | NO₂ | OCH₃ |
| 245. | SO₂ | SCH₃ | OCH₃ |
| 246. | SO₂ | SO₂CH₃ | OCH₃ |
| 247. | SO₂ | SO₂CH₂CH₃ | OCH₃ |
| 248. | SO₂ | CH₃ | OCH₃ |
| 249. | SO₂ | CF₃ | OCH₃ |
| 250. | SO₂ | OCHF₂ | OCH₃ |
| 251. | Bond | F | OCH(CH₃)₂ |
| 252. | Bond | Cl | OCH(CH₃)₂ |
| 253. | Bond | Br | OCH(CH₃)₂ |
| 254. | Bond | NO₂ | OCH(CH₃)₂ |
| 255. | Bond | SCH₃ | OCH(CH₃)₂ |
| 256. | Bond | SO₂CH₃ | OCH(CH₃)₂ |
| 257. | Bond | SO₂CH₂CH₃ | OCH(CH₃)₂ |
| 258. | Bond | CH₃ | OCH(CH₃)₂ |
| 259. | Bond | CF₃ | OCH(CH₃)₂ |
| 260. | Bond | OCHF₂ | OCH(CH₃)₂ |
| 261. | CH₂ | F | OCH(CH₃)₂ |
| 262. | CH₂ | Cl | OCH(CH₃)₂ |
| 263. | CH₂ | Br | OCH(CH₃)₂ |
| 264. | CH₂ | NO₂ | OCH(CH₃)₂ |
| 265. | CH₂ | SCH₃ | OCH(CH₃)₂ |
| 266. | CH₂ | SO₂CH₃ | OCH(CH₃)₂ |
| 267. | CH₂ | SO₂CH₂CH₃ | OCH(CH₃)₂ |
| 268. | CH₂ | CH₃ | OCH(CH₃)₂ |
| 269. | CH₂ | CF₃ | OCH(CH₃)₂ |
| 270. | CH₂ | OCHF₂ | OCH(CH₃)₂ |
| 271. | O | F | OCH(CH₃)₂ |
| 272. | O | Cl | OCH(CH₃)₂ |
| 273. | O | Br | OCH(CH₃)₂ |
| 274. | O | NO₂ | OCH(CH₃)₂ |
| 275. | O | SCH₃ | OCH(CH₃)₂ |
| 276. | O | SO₂CH₃ | OCH(CH₃)₂ |
| 277. | O | SO₂CH₂CH₃ | OCH(CH₃)₂ |
| 278. | O | CH₃ | OCH(CH₃)₂ |
| 279. | O | CF₃ | OCH(CH₃)₂ |
| 280. | O | OCHF₂ | OCH(CH₃)₂ |
| 281. | S | F | OCH(CH₃)₂ |
| 282. | S | Cl | OCH(CH₃)₂ |
| 283. | S | Br | OCH(CH₃)₂ |
| 284. | S | NO₂ | OCH(CH₃)₂ |
| 285. | S | SCH₃ | OCH(CH₃)₂ |
| 286. | S | SO₂CH₃ | OCH(CH₃)₂ |
| 287. | S | SO₂CH₂CH₃ | OCH(CH₃)₂ |
| 288. | S | CH₃ | OCH(CH₃)₂ |
| 289. | S | CF₃ | OCH(CH₃)₂ |
| 290. | S | OCHF₂ | OCH(CH₃)₂ |
| 291. | SO₂ | F | OCH(CH₃)₂ |
| 292. | SO₂ | Cl | OCH(CH₃)₂ |
| 293. | SO₂ | Br | OCH(CH₃)₂ |
| 294. | SO₂ | NO₂ | OCH(CH₃)₂ |
| 295. | SO₂ | SCH₃ | OCH(CH₃)₂ |
| 296. | SO₂ | SO₂CH₃ | OCH(CH₃)₂ |
| 297. | SO₂ | SO₂CH₂CH₃ | OCH(CH₃)₂ |
| 298. | SO₂ | CH₃ | OCH(CH₃)₂ |
| 299. | SO₂ | CF₃ | OCH(CH₃)₂ |
| 300. | SO₂ | OCHF₂ | OCH(CH₃)₂ |
| 301. | Bond | F | OCH₂C₆H₅ |
| 302. | Bond | Cl | OCH₂C₆H₅ |
| 303. | Bond | Br | OCH₂C₆H₅ |
| 304. | Bond | NO₂ | OCH₂C₆H₅ |
| 305. | Bond | SCH₃ | OCH₂C₆H₅ |
| 306. | Bond | SO₂CH₃ | OCH₂C₆H₅ |
| 307. | Bond | SO₂CH₂CH₃ | OCH₂C₆H₅ |
| 308. | Bond | CH₃ | OCH₂C₆H₅ |
| 309. | Bond | CF₃ | OCH₂C₆H₅ |
| 310. | Bond | OCHF₂ | OCH₂C₆H₅ |
| 311. | CH₂ | F | OCH₂C₆H₅ |
| 312. | CH₂ | Cl | OCH₂C₆H₅ |
| 313. | CH₂ | Br | OCH₂C₆H₅ |
| 314. | CH₂ | NO₂ | OCH₂C₆H₅ |
| 315. | CH₂ | SCH₃ | OCH₂C₆H₅ |
| 316. | CH₂ | SO₂CH₃ | OCH₂C₆H₅ |
| 317. | CH₂ | SO₂CH₂CH₃ | OCH₂C₆H₅ |
| 318. | CH₂ | CH₃ | OCH₂C₆H₅ |
| 319. | CH₂ | CF₃ | OCH₂C₆H₅ |
| 320. | CH₂ | OCHF₂ | OCH₂C₆H₅ |
| 321. | O | F | OCH₂C₆H₅ |
| 322. | O | Cl | OCH₂C₆H₅ |
| 323. | O | Br | OCH₂C₆H₅ |
| 324. | O | NO₂ | OCH₂C₆H₅ |
| 325. | O | SCH₃ | OCH₂C₆H₅ |
| 326. | O | SO₂CH₃ | OCH₂C₆H₅ |
| 327. | O | SO₂CH₂CH₃ | OCH₂C₆H₅ |
| 328. | O | CH₃ | OCH₂C₆H₅ |
| 329. | O | CF₃ | OCH₂C₆H₅ |
| 330. | O | OCHF₂ | OCH₂C₆H₅ |
| 331. | S | F | OCH₂C₆H₅ |
| 332. | S | Cl | OCH₂C₆H₅ |
| 333. | S | Br | OCH₂C₆H₅ |
| 334. | S | NO₂ | OCH₂C₆H₅ |
| 335. | S | SCH₃ | OCH₂C₆H₅ |
| 336. | S | SO₂CH₃ | OCH₂C₆H₅ |
| 337. | S | SO₂CH₂CH₃ | OCH₂C₆H₅ |
| 338. | S | CH₃ | OCH₂C₆H₅ |
| 339. | S | CF₃ | OCH₂C₆H₅ |
| 340. | S | OCHF₂ | OCH₂C₆H₅ |
| 341. | SO₂ | F | OCH₂C₆H₅ |
| 342. | SO₂ | Cl | OCH₂C₆H₅ |
| 343. | SO₂ | Br | OCH₂C₆H₅ |
| 344. | SO₂ | NO₂ | OCH₂C₆H₅ |
| 345. | SO₂ | SCH₃ | OCH₂C₆H₅ |
| 346. | SO₂ | SO₂CH₃ | OCH₂C₆H₅ |
| 347. | SO₂ | SO₂CH₂CH₃ | OCH₂C₆H₅ |
| 348. | SO₂ | CH₃ | OCH₂C₆H₅ |
| 349. | SO₂ | CF₃ | OCH₂C₆H₅ |
| 350. | SO₂ | OCHF₂ | OCH₂C₆H₅ |
| 351. | Bond | F | OSO₂(4-CH₃—C₆H₄) |
| 352. | Bond | Cl | OSO₂(4-CH₃—C₆H₄) |
| 353. | Bond | Br | OSO₂(4-CH₃—C₆H₄) |
| 354. | Bond | NO₂ | OSO₂(4-CH₃—C₆H₄) |
| 355. | Bond | SCH₃ | OSO₂(4-CH₃—C₆H₄) |
| 356. | Bond | SO₂CH₃ | OSO₂(4-CH₃—C₆H₄) |
| 357. | Bond | SO₂CH₂CH₃ | OSO₂(4-CH₃—C₆H₄) |
| 358. | Bond | CH₃ | OSO₂(4-CH₃—C₆H₄) |
| 359. | Bond | CF₃ | OSO₂(4-CH₃—C₆H₄) |
| 360. | Bond | OCHF₂ | OSO₂(4-CH₃—C₆H₄) |
| 361. | CH₂ | F | OSO₂(4-CH₃—C₆H₄) |
| 362. | CH₂ | Cl | OSO₂(4-CH₃—C₆H₄) |
| 363. | CH₂ | Br | OSO₂(4-CH₃—C₆H₄) |
| 364. | CH₂ | NO₂ | OSO₂(4-CH₃—C₆H₄) |
| 365. | CH₂ | SCH₃ | OSO₂(4-CH₃—C₆H₄) |
| 366. | CH₂ | SO₂CH₃ | OSO₂(4-CH₃—C₆H₄) |
| 367. | CH₂ | SO₂CH₂CH₃ | OSO₂(4-CH₃—C₆H₄) |
| 368. | CH₂ | CH₃ | OSO₂(4-CH₃—C₆H₄) |
| 369. | CH₂ | CF₃ | OSO₂(4-CH₃—C₆H₄) |
| 370. | CH₂ | OCHF₂ | OSO₂(4-CH₃—C₆H₄) |
| 371. | O | F | OSO₂(4-CH₃—C₆H₄) |
| 372. | O | Cl | OSO₂(4-CH₃—C₆H₄) |
| 373. | O | Br | OSO₂(4-CH₃—C₆H₄) |

TABLE 1-continued

Ia1

| n | X | R⁴ | R¹⁰ |
|---|---|---|---|
| 374. | O | NO₂ | OSO₂(4-CH₃—C₆H₄) |
| 375. | O | SCH₃ | OSO₂(4-CH₃—C₆H₄) |
| 376. | O | SO₂CH₃ | OSO₂(4-CH₃—C₆H₄) |
| 377. | O | SO₂CH₂CH₃ | OSO₂(4-CH₃—C₆H₄) |
| 378. | O | CH₃ | OSO₂(4-CH₃—C₆H₄) |
| 379. | O | CF₃ | OSO₂(4-CH₃—C₆H₄) |
| 380. | O | OCHF₂ | OSO₂(4-CH₃—C₆H₄) |
| 381. | S | F | OSO₂(4-CH₃—C₆H₄) |
| 382. | S | Cl | OSO₂(4-CH₃—C₆H₄) |
| 383. | S | Br | OSO₂(4-CH₃—C₆H₄) |
| 384. | S | NO₂ | OSO₂(4-CH₃—C₆H₄) |
| 385. | S | SCH₃ | OSO₂(4-CH₃—C₆H₄) |
| 386. | S | SO₂CH₃ | OSO₂(4-CH₃—C₆H₄) |
| 387. | S | SO₂CH₂CH₃ | OSO₂(4-CH₃—C₆H₄) |
| 388. | S | CH₃ | OSO₂(4-CH₃—C₆H₄) |
| 389. | S | CF₃ | OSO₂(4-CH₃—C₆H₄) |
| 390. | S | OCHF₂ | OSO₂(4-CH₃—C₆H₄) |
| 391. | SO₂ | F | OSO₂(4-CH₃—C₆H₄) |
| 392. | SO₂ | Cl | OSO₂(4-CH₃—C₆H₄) |
| 393. | SO₂ | Br | OSO₂(4-CH₃—C₆H₄) |
| 394. | SO₂ | NO₂ | OSO₂(4-CH₃—C₆H₄) |
| 395. | SO₂ | SCH₃ | OSO₂(4-CH₃—C₆H₄) |
| 396. | SO₂ | SO₂CH₃ | OSO₂(4-CH₃—C₆H₄) |
| 397. | SO₂ | SO₂CH₂CH₃ | OSO₂(4-CH₃—C₆H₄) |
| 398. | SO₂ | CH₃ | OSO₂(4-CH₃—C₆H₄) |
| 399. | SO₂ | CF₃ | OSO₂(4-CH₃—C₆H₄) |
| 400. | SO₂ | OCHF₂ | OSO₂(4-CH₃—C₆H₄) |
| 401. | Bond | F | SCH₃ |
| 402. | Bond | Cl | SCH₃ |
| 403. | Bond | Br | SCH₃ |
| 404. | Bond | NO₂ | SCH₃ |
| 405. | Bond | SCH₃ | SCH₃ |
| 406. | Bond | SO₂CH₃ | SCH₃ |
| 407. | Bond | SO₂CH₂CH₃ | SCH₃ |
| 408. | Bond | CH₃ | SCH₃ |
| 409. | Bond | CF₃ | SCH₃ |
| 410. | Bond | OCHF₂ | SCH₃ |
| 411. | CH₂ | F | SCH₃ |
| 412. | CH₂ | Cl | SCH₃ |
| 413. | CH₂ | Br | SCH₃ |
| 414. | CH₂ | NO₂ | SCH₃ |
| 415. | CH₂ | SCH₃ | SCH₃ |
| 416. | CH₂ | SO₂CH₃ | SCH₃ |
| 417. | CH₂ | SO₂CH₂CH₃ | SCH₃ |
| 418. | CH₂ | CH₃ | SCH₃ |
| 419. | CH₂ | CF₃ | SCH₃ |
| 420. | CH₂ | OCHF₂ | SCH₃ |
| 421. | O | F | SCH₃ |
| 422. | O | Cl | SCH₃ |
| 423. | O | Br | SCH₃ |
| 424. | O | NO₂ | SCH₃ |
| 425. | O | SCH₃ | SCH₃ |
| 426. | O | SO₂CH₃ | SCH₃ |
| 427. | O | SO₂CH₂CH₃ | SCH₃ |
| 428. | O | CH₃ | SCH₃ |
| 429. | O | CF₃ | SCH₃ |
| 430. | O | OCHF₂ | SCH₃ |
| 431. | S | F | SCH₃ |
| 432. | S | Cl | SCH₃ |
| 433. | S | Br | SCH₃ |
| 434. | S | NO₂ | SCH₃ |
| 435. | S | SCH₃ | SCH₃ |
| 436. | S | SO₂CH₃ | SCH₃ |
| 437. | S | SO₂CH₂CH₃ | SCH₃ |
| 438. | S | CH₃ | SCH₃ |
| 439. | S | CF₃ | SCH₃ |
| 440. | S | OCHF₂ | SCH₃ |
| 441. | SO₂ | F | SCH₃ |
| 442. | SO₂ | Cl | SCH₃ |
| 443. | SO₂ | Br | SCH₃ |
| 444. | SO₂ | NO₂ | SCH₃ |
| 445. | SO₂ | SCH₃ | SCH₃ |
| 446. | SO₂ | SO₂CH₃ | SCH₃ |
| 447. | SO₂ | SO₂CH₂CH₃ | SCH₃ |
| 448. | SO₂ | CH₃ | SCH₃ |
| 449. | SO₂ | CF₃ | SCH₃ |
| 450. | SO₂ | OCHF₂ | SCH₃ |
| 451. | Bond | F | Cl |
| 452. | Bond | Cl | Cl |
| 453. | Bond | Br | Cl |
| 454. | Bond | NO₂ | Cl |
| 455. | Bond | SCH₃ | Cl |
| 456. | Bond | SO₂CH₃ | Cl |
| 457. | Bond | SO₂CH₂CH₃ | Cl |
| 458. | Bond | CH₃ | Cl |
| 459. | Bond | CF₃ | Cl |
| 460. | Bond | OCHF₂ | Cl |
| 461. | CH₂ | F | Cl |
| 462. | CH₂ | Cl | Cl |
| 463. | CH₂ | Br | Cl |
| 464. | CH₂ | NO₂ | Cl |
| 465. | CH₂ | SCH₃ | Cl |
| 466. | CH₂ | SO₂CH₃ | Cl |
| 467. | CH₂ | SO₂CH₂CH₃ | Cl |
| 468. | CH₂ | CH₃ | Cl |
| 469. | CH₂ | CF₃ | Cl |
| 470. | CH₂ | OCHF₂ | Cl |
| 471. | O | F | Cl |
| 472. | O | Cl | Cl |
| 473. | O | Br | Cl |
| 474. | O | NO₂ | Cl |
| 475. | O | SCH₃ | Cl |
| 476. | O | SO₂CH₃ | Cl |
| 477. | O | SO₂CH₂CH₃ | Cl |
| 478. | O | CH₃ | Cl |
| 479. | O | CF₃ | Cl |
| 480. | O | OCHF₂ | Cl |
| 481. | S | F | Cl |
| 482. | S | Cl | Cl |
| 483. | S | Br | Cl |
| 484. | S | NO₂ | Cl |
| 485. | S | SCH₃ | Cl |
| 486. | S | SO₂CH₃ | Cl |
| 487. | S | SO₂CH₂CH₃ | Cl |
| 488. | S | CH₃ | Cl |
| 489. | S | CF₃ | Cl |
| 490. | S | OCHF₂ | Cl |
| 491. | SO₂ | F | Cl |
| 492. | SO₂ | Cl | Cl |
| 493. | SO₂ | Br | Cl |
| 494. | SO₂ | NO₂ | Cl |
| 495. | SO₂ | SCH₃ | Cl |
| 496. | SO₂ | SO₂CH₃ | Cl |
| 497. | SO₂ | SO₂CH₂CH₃ | Cl |
| 498. | SO₂ | CH₃ | Cl |
| 499. | SO₂ | CF₃ | Cl |
| 500. | SO₂ | OCHF₂ | Cl |

Likewise, particular preference is given to the compounds of the formula Ia2 (=Ia where $R^1$, $R^2$, $R^5$ and $R^{11}$ to $R^{16}$=H, $R^3$=CH₃, m=1), in particular to the compounds Ia2.n, where the variables X, $R^4$ and $R^{10}$ are as defined in Table 1.

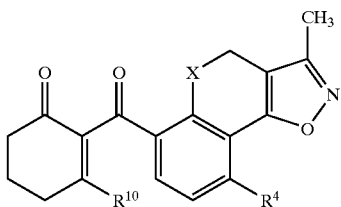
Ia2

Likewise, particular preference is given to the compounds of the formula Ia3 (=Ia where $R^1$, $R^2$, $R^5$ and $R^{11}$ to $R^{16}$=H, $R^3$=CH$_3$, m=1), in particular to the compounds Ia3.n, where the variables X, $R^4$ and $R^{10}$ are as defined in Table 1.

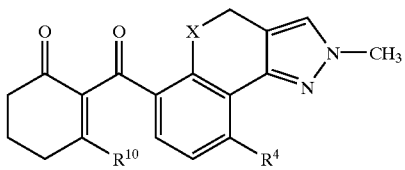
Ia3

Likewise, particular preference is given to the compounds of the formula Ia4 (=Ia where $R^1$, $R^2$, $R^5$ and $R^{11}$ to $R^{16}$=H, $R^3$=CH$_3$, m=2), in particular to the compounds Ia4.n, where the variables X, $R^4$ and $R^{10}$ are as defined in Table 1.

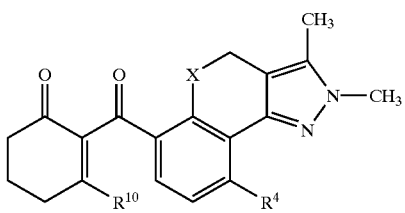
Ia4

Likewise, particular preference is given to the compounds of the formula Ia5 (=Ia where $R^1$, $R^2$, $R^5$ and $R^{11}$ to $R^{16}$=H, $R^3$=CH$_3$, m=1), in particular to the compounds Ia5.n, where the variables X, $R^4$ and $R^{10}$ are as defined in Table 1.

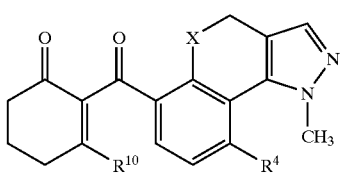
Ia5

Likewise, particular preference is given to the compounds of the formula Ia6 (=Ia where $R^1$, $R^2$, $R^5$ and $R^{11}$ to $R^{16}$=H, $R^3$=CH$_3$, m=2), in particular to the compounds Ia6.n, where the variables X, $R^4$ and $R^{10}$ are as defined in Table 1.

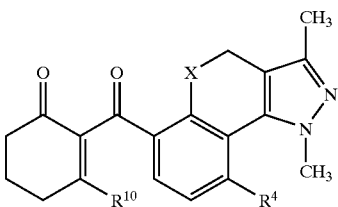
Ia6

Likewise, particular preference is given to the compounds of the formula Ia7 (=Ia where $R^1$, $R^2$, $R^5$ and $R^{11}$ to $R^{16}$=H, m=0), in particular to the compounds Ia7.n, where the variables X, $R^4$ and $R^{10}$ are as defined in Table 1.

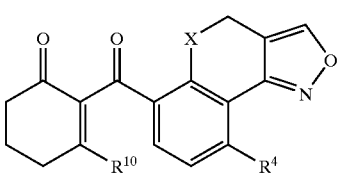
Ia7

Likewise, particular preference is given to the compounds of the formula Ia8 (=Ia where $R^1$, $R^2$, $R^5$ and $R^{11}$ to $R^{16}$=H, $R^3$=CH$_3$, m=1), in particular to the compounds Ia8.n, where the variables X, $R^4$ and $R^{10}$ are as defined in Table 1.

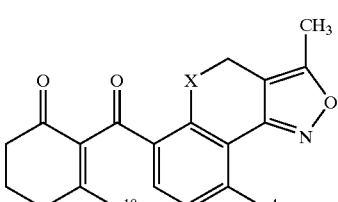
Ia8

Likewise, particular preference is given to the compounds of the formula Ia9 (=Ia where $R^1$, $R^2$, $R^5$ and $R^{11}$ to $R^{16}$=H, m=0), in particular to the compounds Ia9.n, where the variables X, $R^4$ and $R^{10}$ are as defined in Table 1.

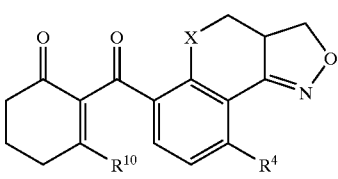
Ia9

Likewise, particular preference is given to the compounds of the formula Ia10 (=Ia where $R^1$, $R^2$, $R^5$ and $R^{11}$ to $R^{16}$=H, m=0), in particular to the compounds Ia10.n, where the variables X, $R^4$ and $R^{10}$ are as defined in Table 1.

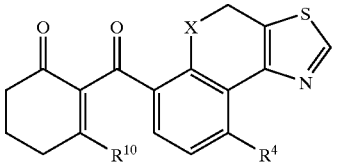
Ia10

Likewise, particular preference is given to the compounds of the formula Ia11 (≡Ia where $R^1$, $R^2$, $R^5$ and $R^{11}$ to $R^{16}$=H, m=0), in particular to the compounds Ia11.n, where the variables X, $R^4$ and $R^{10}$ are as defined in Table 1.

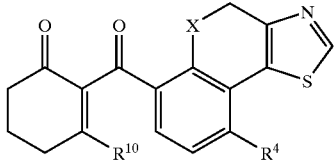

Ia11

Likewise, particular preference is given to the compounds of the formula Ia12 (≡Ia where $R^1$, $R^2$, $R^5$ and $R^{11}$ to $R^{16}$=H, m=0) in particular to the compounds Ia12.n, where the variables X, $R^4$ and $R^{10}$ are as defined in Table 1.

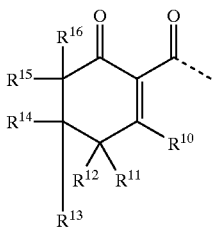

IIa

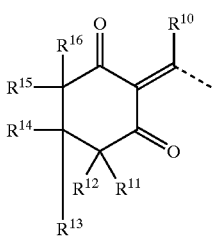

IIb

Likewise, particular preference is given to the compounds of the formula Ia13 (≡Ia where $R^1$, $R^2$, $R^5$ and $R^{11}$ to $R^{16}$=H, m=0), in particular to the compounds Ia13.n, where the variables X, $R^4$ and $R^{10}$ are as defined in Table 1.

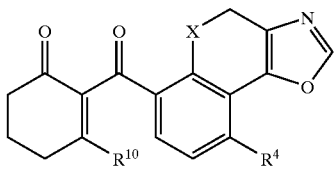

Ia13

Likewise, particular preference is given to the compounds of the formula Ia14 (≡Ia where $R^1$, $R^2$, $R^5$ and $R^{11}$ to $R^{16}$=H, $R^3$=CH$_3$, m=1), in particular to the compounds Ia14.n, where the variables X, $R^4$ and $R^{10}$ are as defined in Table 1.

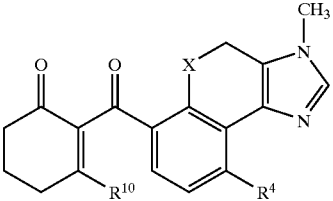

Ia14

Likewise, particular preference is given to the compounds of the formula Ia15 (≡Ia where $R^1$, $R^2$, $R^5$ and $R^{11}$ to $R^{16}$=H, $R^3$=CH$_3$, m=1), in particular to the compounds Ia15.n, where the variables X, $R^4$ and $R^{10}$ are as defined in Table 1.

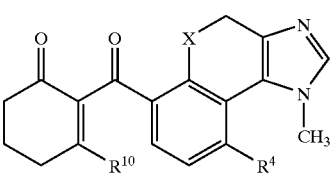

Ia15

Likewise, particular preference is given to the compounds of the formula Ia16 (≡Ia where $R^1$, $R^2$, $R^5$ and $R^{11}$ to $R^{16}$=H, m=0), in particular to the compounds Ia16.n, where the variables X, $R^4$ and $R^{10}$ are as defined in Table 1.

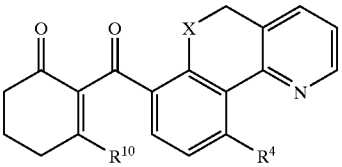

Ia16

Likewise particular preference is given to the compounds of the formula Ia17 (≡Ia where $R^1$, $R^2$, $R^5$ and $R^{11}$ to $R^{16}$=H, m=0), in particular to the compounds Ia17.n, where the variables X, $R^4$ and $R^{10}$ are as defined in Table 1.

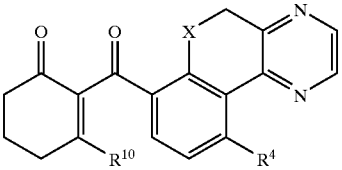

Ia17

Likewise particular preference is given to the compounds of the formula Ia18 (≡Ia where $R^1$, $R^2$, $R^5$ and $R^{11}$ to $R^{16}$=H, $R^{13}$=CH$_3$, m=1), in particular to the compounds Ia18.n, where the variables X, $R^4$ and $R^{10}$ are as defined in Table 1.

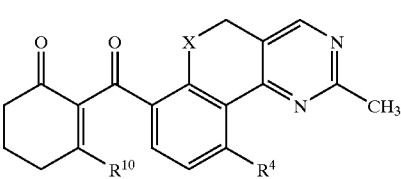

Ia18

Likewise particular preference is given to the compounds of the formula Ia19 (=Ia where $R^1$, $R^2$, $R^5$ and $R^{11}$ to $R^{16}$=H, m=0), in particular to the compounds Ia19.n, where the variables X, $R^4$ and $R^{10}$ are as defined in Table 1.

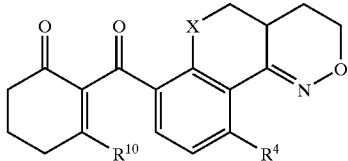

Ia19

Likewise particular preference is given to compounds of the formula Ia20 (=Ia where $R^1$, $R^2$, $R^5$ and $R^{11}$ to $R^{16}$=H, m=0), in particular to the compound Ia20.n, where the variable X, $R^4$ and $R^{10}$ are as defined in table 1.

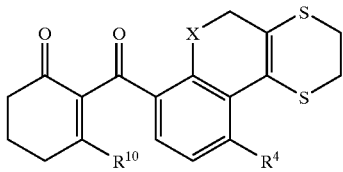

Ia20

Likewise particular preference is given to the compounds of the formula Ia21 (=Ia where $R^1$, $R^2$, $R^5$ and $R^{11}$ to $R^{16}$=H, m=0), in particular to the compounds Ia21.n, where the variables X, $R^4$ and $R^{10}$ are as defined in Table 1.

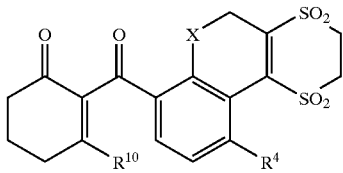

Ia21

Likewise particular preference is given to the compounds of the formula Ia22 (=Ia where $R^1$, $R^2$, $R^5$ and $R^{11}$ to $R^{16}$=H, $R^3$=CH$_3$, m=1), in particular to the compounds Ia22.n, where the variables X, $R^4$ and $R^{10}$ are as defined in Table 1.

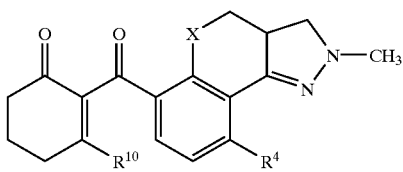

Ia22

Likewise particular preference is given to the compounds of the formula Ia23 (=Ia where $R^1$, $R^2$, $R^5$ and $R^{11}$, $R^{12}$, $R^{14}$ to $R^{16}$=H, $R^{13}$=H, m=0), in particular to the compounds Ia23.n, where the variables X, $R^4$ and $R^{10}$ are as defined in Table 1.

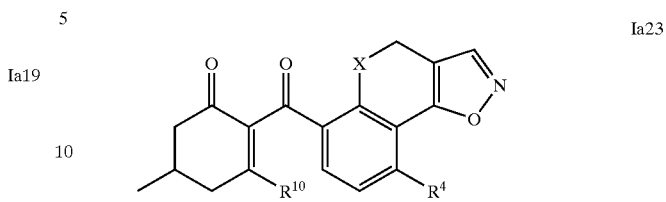

Ia23

Likewise particular preference is given to the compounds of the formula Ia24 (=Ia where $R^1$, $R^2$, $R^5$ and $R^{11}$, $R^{12}$, $R^{14}$ to $R^{16}$=H, $R^3$ and $R^{13}$=CH$_3$, m=1), in particular to the compounds Ia24.n, where the variables X, $R^4$ and $R^{10}$ are as defined in Table 1.

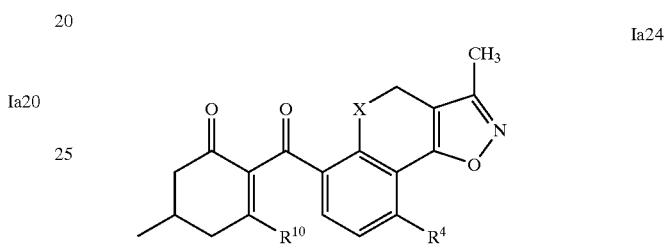

Ia24

Likewise particular preference is given to the compounds of the formula Ia25 (=Ia where $R^1$, $R^2$, $R^5$ and $R^{11}$, $R^{12}$, $R^{14}$ to $R^{16}$=H, $R^3$ and $R^{13}$=CH$_3$, m=1), in particular to the compounds Ia25.n, where the variables X, $R^4$ and $R^{10}$ are as defined in Table 1.

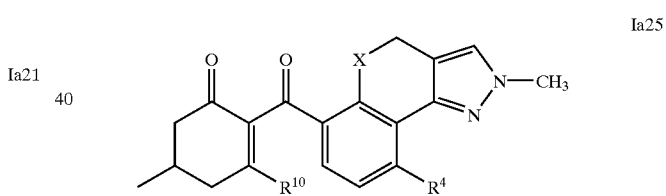

Ia25

Likewise particular preference is given to the compounds of the formula Ia26 (=Ia where $R^1$, $R^2$, $R^5$ and $R^{11}$, $R^{12}$, $R^{14}$ to $R^{16}$=H, $R^3$ and $R^{13}$=CH$_3$, m=2), in particular to the compounds Ia26.n, where the variables X, $R^4$ and $R^{10}$ are as defined in Table 1.

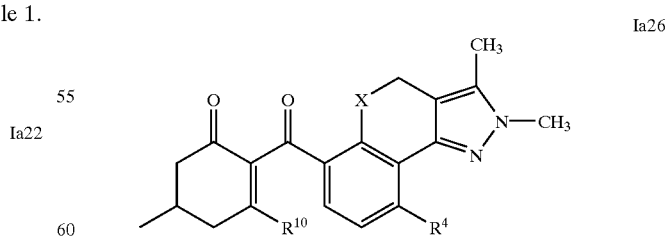

Ia26

Likewise particular preference is given to the compounds of the formula Ia27 (=Ia where $R^1$, $R^2$, $R^5$ and $R^{11}$, $R^{12}$, $R^{14}$ to $R^{16}$=H, $R^3$ and $R^{13}$=CH$_3$, m=1), in particular to the compounds Ia27.n, where the variables X, $R^4$ and $R^{10}$ are as defined in Table 1.

Ia27

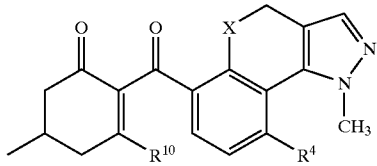

Likewise particular preference is given to the compounds of the formula Ia28 (=Ia where $R^1$, $R^2$, $R^5$ and $R^{11}$, $R^{12}$, $R^{14}$ to $R^{16}$=H, $R^3$ and $R^{13}$=CH$_3$, m=2), in particular to the compounds Ia28.n, where the variables X, $R^4$ and $R^{10}$ are as defined in Table 1.

Ia28

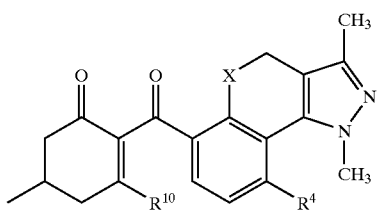

Likewise particular preference is given to the compounds of the formula Ia29 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia29.n, where the variables X, $R^4$ and $R^{10}$ are as defined in Table 1.

Ia29

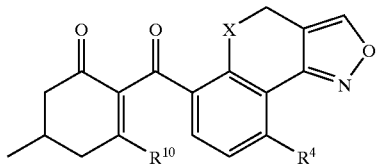

Likewise particular preference is given to the compounds of the formula Ia30 (=Ia where $R^1$, $R^2$, $R^5$ and $R^{11}$, $R^{12}$, $R^{14}$ to $R^{16}$=H, $R^3$ and $R^{13}$=CH$^3$, m=1), in particular to the compounds Ia30.n, where the variables X, $R^4$ and $R^{10}$ are as defined in Table 1.

Ia30

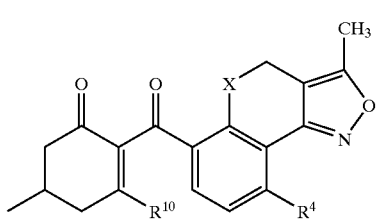

Likewise particular preference is given to the compounds of the formula Ia31 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia31.n, where the variables X, $R^4$ and $R^{10}$ are as defined in Table 1.

Ia31

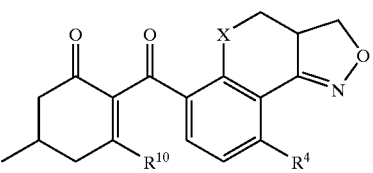

Likewise particular preference is given to the compounds of the formula Ia32 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia32.n, where the variables X, $R^4$ and $R^{10}$ are as defined in Table 1.

Ia32

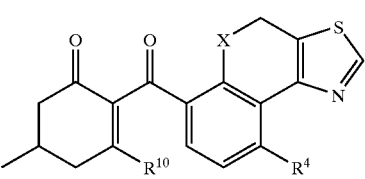

Likewise particular preference is given to the compounds of the formula Ia33 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia33.n, where the variables X, $R^4$ and $R^{10}$ are as defined in Table 1.

Ia33

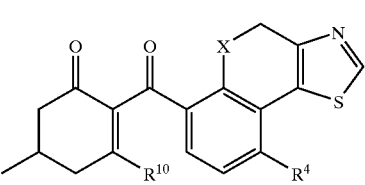

Likewise particular preference is given to the compounds of the formula Ia34 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia34.n, where the variables X, $R^4$ and $R^{10}$ are as defined in Table 1.

Ia34

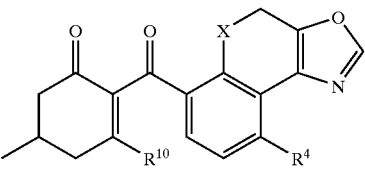

Likewise particular preference is given to the compounds of the formula Ia35 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia35.n, where the variables X, $R^4$ and $R^{10}$ are as defined in Table 1.

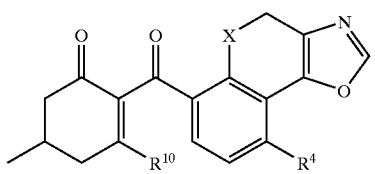

Ia35

Likewise particular preference is given to the compounds of the formula Ia36 (=Ia where $R^1$, $R^2$, $R^5$ and $R^{11}$, $R^{12}$, $R^{14}$ to $R^{16}$=H, $R^3$ and $R^{13}$=CH$_3$, m=1), in particular to the compounds Ia36.n, where the variables X, $R^4$ and $R^{10}$ are as defined in Table 1.

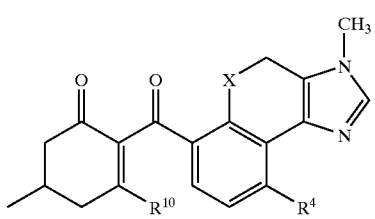

Ia36

Likewise particular preference is given to the compounds of the formula Ia37 (=Ia where $R^1$, $R^2$, $R^5$ and $R^{11}$, $R^{12}$, $R^{14}$ to $R^{16}$=H, $R^3$ and $R^{13}$=CH$_3$, m=1), in particular to the compounds Ia37.n, where the variables X, $R^4$ and $R^{10}$ are as defined in Table 1.

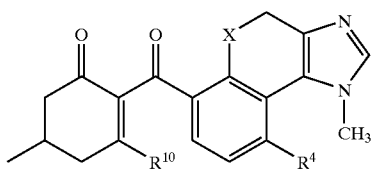

Ia37

Likewise particular preference is given to the compounds of the formula Ia38 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia38.n, where the variables X, $R^4$ and $R^{10}$ are as defined in Table 1.

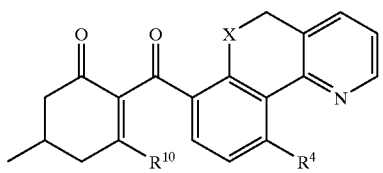

Ia38

Likewise particular preference is given to the compounds of the formula Ia39 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia39.n, where the variables X, $R^4$ and $R^{10}$ are as defined in Table 1.

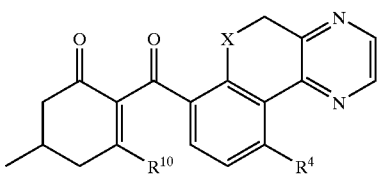

Ia39

Likewise particular preference is given to the compounds of the formula Ia40 (=Ia where $R^1$, $R^2$, $R^5$ and $R^{11}$, $R^{12}$, $R^{14}$ to $R^{16}$=H, $R^3$ and $R^{13}$=CH$_3$, m=1), in particular to the compounds Ia40.n, where the variables X, $R^4$ and $R^{10}$ are as defined in Table 1.

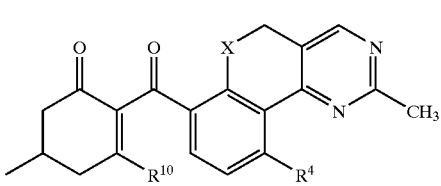

Ia40

Likewise particular preference is given to the compounds of the formula Ia41 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia41.n, where the variables X, $R^4$ and $R^{10}$ are as defined in Table 1.

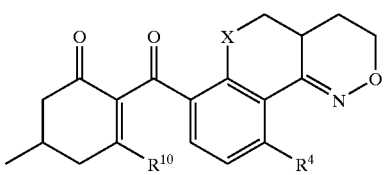

Ia41

Likewise particular preference is given to the compounds of the formula Ia42 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia42.n, where the variables X, $R^4$ and $R^{10}$ are as defined in Table 1.

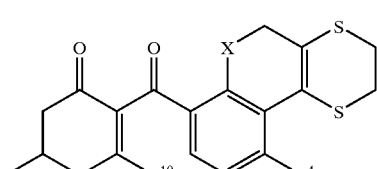

Ia42

Likewise particular preference is given to the compounds of the formula Ia43 (=Ia where $R^1$, $R^2$, $R^5$ and $R^{11}$, $R^{12}$, $R^{14}$ to $R^{16}$=H, $R^{13}$=CH$_3$, m=0), in particular to the compounds Ia43.n, where the variables X, $R^4$ and $R^{10}$ are as defined in Table 1.

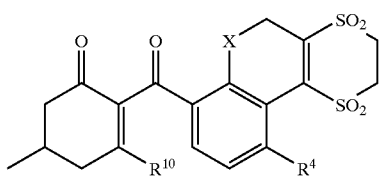

Ia43

Likewise particular preference is given to the compounds of the formula Ia44 (=Ia where $R^1$, $R^2$, $R^5$ and $R^{11}$, $R^{12}$, $R^{14}$ to $R^{16}$=H, $R^3$ and $R^{13}$=CH$_3$, m=1), in particular to the compounds Ia44.n, where the variables X, $R^4$ and $R^{10}$ are as defined in Table 1.

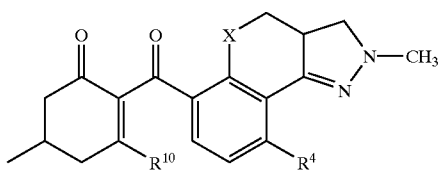

Ia44

Likewise particular preference is given to the compounds of the formula Ia45 (=Ia where $R^1$, $R^2$, $R^5$ and $R^{11}$, $R^{12}$, $R^{15}$ and $R^{16}$=H, $R^{13}$ and $R^{14}$=CH$_3$, m=0), in particular to the compounds Ia45.n, where the variables X, $R^4$ and $R^{10}$ are as defined in Table 1.

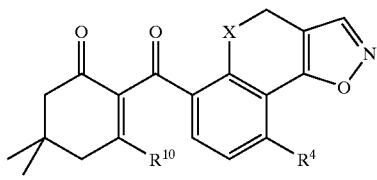

Ia45

Likewise particular preference is given to the compounds of the formula Ia46 (=Ia where $R^1$, $R^2$, $R^5$ and $R^{11}$, $R^{12}$ $R^{15}$, $R^{16}$=H, $R^3$, $R^{13}$ and $R^{14}$=CH$_3$, m=1), in particular to the compounds Ia46.n, where the variables X, $R^4$ and $R^{10}$ are as defined in Table 1.

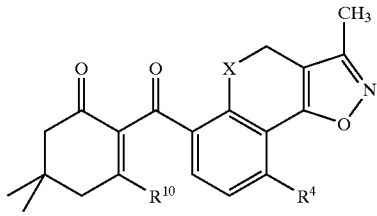

Ia46

Likewise particular preference is given to the compounds of the formula Ia47 (=Ia where $R^1$, $R^2$, $R^5$ and $R^{11}$, $R^{12}$, $R^{15}$, $R^{16}$=H, $R^3$, $R^{13}$ and $R^{14}$=CH$_3$, m=1), in particular to the compounds Ia47.n, where the variables X, $R^4$ and $R^{10}$ are as defined in Table 1.

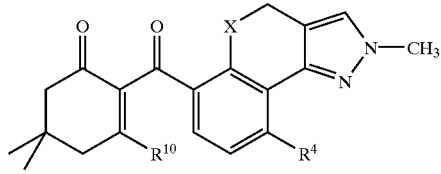

Ia47

Likewise particular preference is given to the compounds of the formula Ia48 (=Ia where $R^1$, $R^2$, $R^5$ and $R^{11}$, $R^{12}$, $R^{15}$, $R^{16}$=H, $R^3$, $R^{13}$ and $R^{14}$=CH$_3$, m=2), in particular to the compounds Ia48.n, where the variables X, $R^4$ and $R^{10}$ are as defined in Table 1.

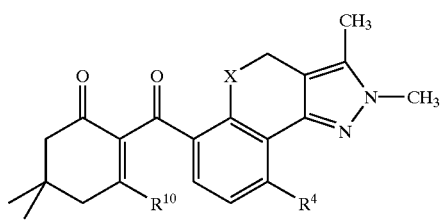

Ia48

Likewise particular preference is given to the compounds of the formula Ia49 (=Ia where $R^1$, $R^2$, $R^5$ and $R^1l$, $R^{12}$, $R^{15}$, $R^{16}$=H, $R^3$, $R^{13}$ and $R^{14}$=CH$_3$, m=1), in particular to the compounds Ia49.n, where the variables X, $R^4$ and $R^{10}$ are as defined in Table 1.

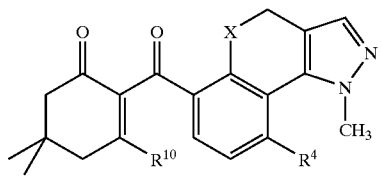

Ia49

Likewise particular preference is given to the compounds of the formula Ia50 (=Ia where $R^1$, $R^2$, $R^5$ and $R^{11}$, $R^{12}$, $R^{15}$, $R^{16}$=H, $R^3$, $R^{13}$ and $R^{14}$=CH$_3$, m=2), in particular to the compounds Ia50.n, where the variables X, $R^4$ and $R^{10}$ are as defined in Table 1.

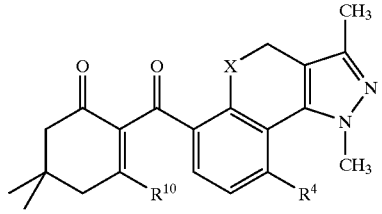

Ia50

Likewise particular preference is given to the compounds of the formula Ia51 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia51.n, where the variables X, $R^4$ and $R^{10}$ are as defined in Table 1.

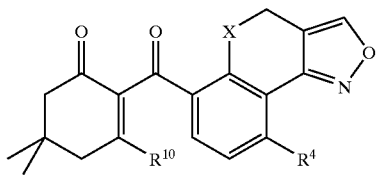

Ia51

Likewise particular preference is given to the compounds of the formula Ia52 (=Ia where $R^1$, $R^2$, $R^5$ and $R^{11}$, $R^{12}$, $R^{15}$, $R^{16}$=H, $R^3$, $R^{13}$ and $R^{14}$=CH$^3$, m=1), in particular to the compounds Ia52.n, where the variables X, $R^4$ and $R^{10}$ are as defined in Table 1.

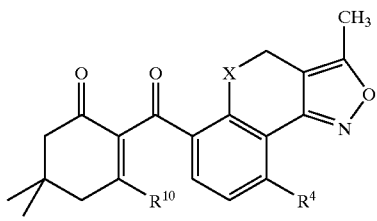

Ia52

Likewise particular preference is given to the compounds of the formula Ia53 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia53.n, where the variables X, $R^4$ and $R^{10}$ are as defined in Table 1.

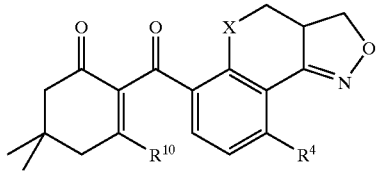

Ia53

Likewise particular preference is given to the compounds of the formula Ia54 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia54.n, where the variables X, $R^4$ and $R^{10}$ are as defined in Table 1.

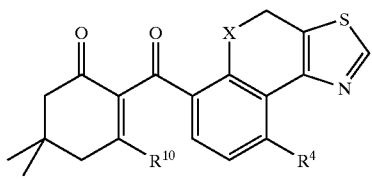

Ia54

Likewise particular preference is given to the compounds of the formula Ia55 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia55.n, where the variables X, $R^4$ and $R^{10}$ are as defined in Table 1.

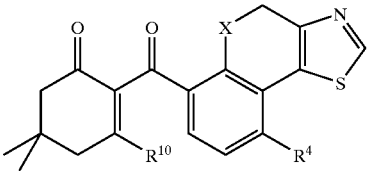

Ia55

Likewise particular preference is given to the compounds of the formula Ia56 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia56.n, where the variables X, $R^4$ and $R^{10}$ are as defined in Table 1.

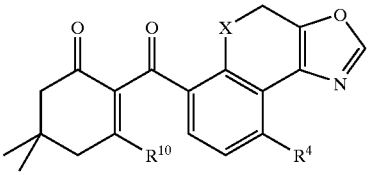

Ia56

Likewise particular preference is given to the compounds of the formula Ia57 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia57.n, where the variables X, $R^4$ and $R^{10}$ are as defined in Table 1.

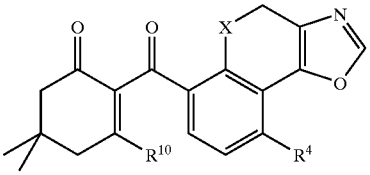

Ia57

Likewise particular preference is given to the compounds of the formula Ia58 (=Ia where $R^1$, $R^2$, $R^5$ and $R^{11}$, $R^{12}$, $R^{15}$, $R^{16}$=H, $R^3$, $R^{13}$ and $R^{14}$=CH$_3$, m=1), in particular to the compounds Ia58.n, where the variables X, $R^4$ and $R^{10}$ are as defined in Table 1.

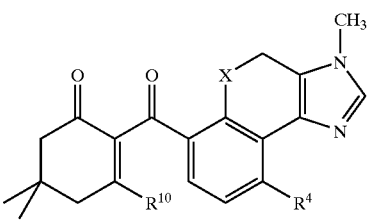

Ia58

Likewise particular preference is given to the compounds of the formula Ia59 (=Ia where $R^1$, $R^2$, $R^5$ and $R^{11}$, $R^{12}$, $R^{15}$, $R^{16}$=H, $R^3$, $R^{13}$ and $R^{14}$=CH$_3$, m=1), in particular to the compounds Ia59.n, where the variables X, $R^4$ and $R^{10}$ are as defined in Table 1.

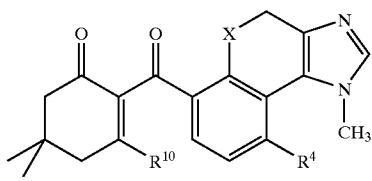

Ia59

Likewise particular preference is given to the compounds of the formula Ia60 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia60.n, where the variables X, $R^4$ and $R^{10}$ are as defined in Table 1.

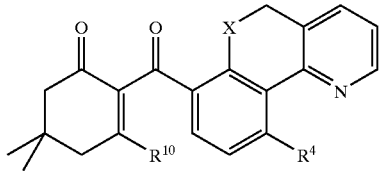

Ia60

Likewise particular preference is given to the compounds of the formula Ia61 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia61.n, where the variables X, $R^4$ and $R^{10}$ are as defined in Table 1.

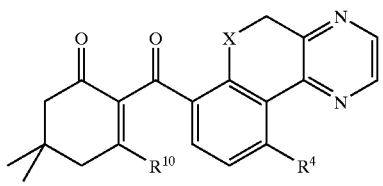

Ia61

Likewise particular preference is given to the compounds of the formula Ia62 (=Ia where $R^1$, $R^2$, $R^5$ and $R^{11}$, $R^{12}$, $R^{15}$, $R^{16}$=H, $R^3$, $R^{13}$ and $R^{14}$=CH$_3$, m=1), in particular to the compounds Ia62.n, where the variables X, $R^4$ and $R^{10}$ are as defined in Table 1.

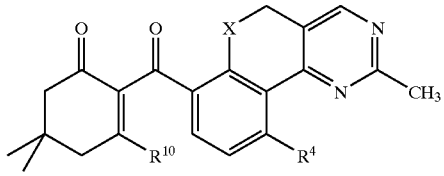

Ia62

Likewise particular preference is given to the compounds of the formula Ia63 (=Ia where $R^1$, $R^2$, $R^5$ and $R^{11}$, $R^{12}$, $R^{15}$, $R^{16}$=H, $R^{13}$ and $R^{14}$ CH$_3$, m=0), in particular to the compounds Ia63.n, where the variables X, $R^4$ and $R^{10}$ are as defined in Table 1.

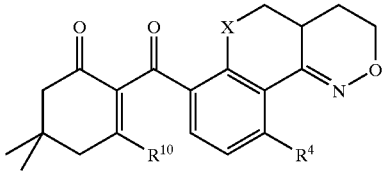

Ia63

Likewise particular preference is given to the compounds of the formula Ia64 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia64.n, where the variables X, $R^4$ and $R^{10}$ are as defined in Table 1.

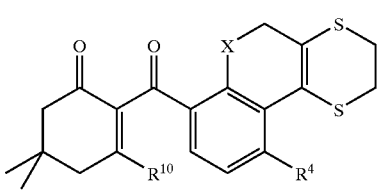

Ia64

Likewise particular preference is given to the compounds of the formula Ia65 (=Ia where $R^1$, $R^2$, $R^5$ and $R^{11}$, $R^{12}$, $R^{15}$, $R^{16}$=H, $R^{13}$ and $R^{14}$=CH$_3$, m=0), in particular to the compounds Ia65.n, where the variables X, $R^4$ and $R^{10}$ are as defined in Table 1.

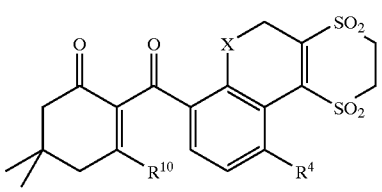

Ia65

Likewise particular preference is given to the compounds of the formula Ia66 (=Ia where $R^1$, $R^2$, $R^5$ and $R^{11}$, $R^{12}$, $R^{15}$, $R^{16}$=R, $R^3$, $R^{13}$ and $R^{14}$=CH$_3$, m=1), in particular to the compounds Ia66.n, where the variables X, $R^4$ and $R^{10}$ are as defined in Table 1.

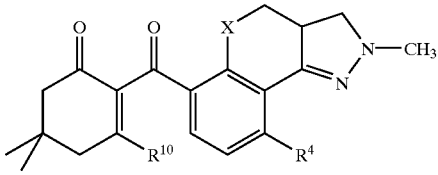

Ia66

Likewise particular preference is given to the compounds of the formula Ia67 (=Ia where $R^1$, $R^2$, $R^5$ and $R^{12}$ to $R^{16}$=H, $R^{11}$=CH$_3$, m=1), in particular to the compounds Ia67.n, where the variables X, $R^4$ and $R^{10}$ are as defined in Table 1.

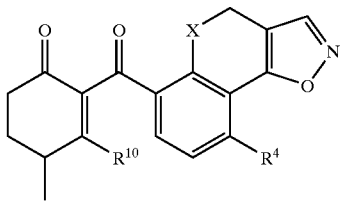
Ia67

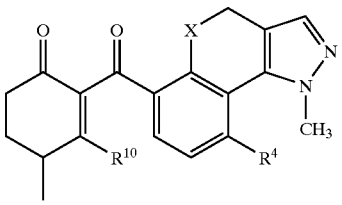
Ia71

Likewise particular preference is given to the compounds of the formula Ia68 (=Ia where $R^1$, $R^2$, $R^5$ and $R^{12}$ to $R^{16}$=H, $R^3$ and $R^{11}$=CH$_3$, m=1), in particular to the compounds Ia68.n, where the variables X, $R^4$ and $R^{10}$ are as defined in Table 1.

Likewise particular preference is given to the compounds of the formula Ia72 (=Ia where $R^1$, $R^2$, $R^5$ and $R^{12}$ to $R^{16}$=H, $R^3$ and $R^{11}$=CH$_3$, m=2), in particular to the compounds Ia72.n, where the variables X, $R^4$ and $R^{10}$ are as defined in Table 1.

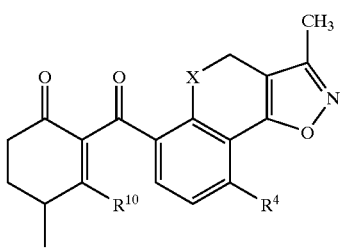
Ia68

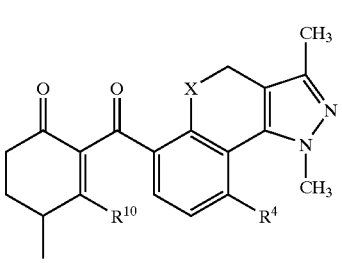
Ia72

Likewise particular preference is given to the compounds of the formula Ia69 (=Ia where $R^1$, $R^2$, $R^5$ and $R^{12}$ to $R^{16}$=H, $R^3$ and $R^{11}$=CH$_3$, m=1), in particular to the compounds Ia69.n, where the variables X, $R^4$ and $R^{10}$ are as defined in Table 1.

Likewise particular preference is given to the compounds of the formula Ia73 (=Ia where $R^1$, $R^2$, $R^5$ and $R^{12}$ to $R^{16}$=H, $R^{11}$=CH$_3$, m=0), in particular to the compounds Ia73.n, where the variables X, $R^4$ and $R^{10}$ are as defined in Table 1.

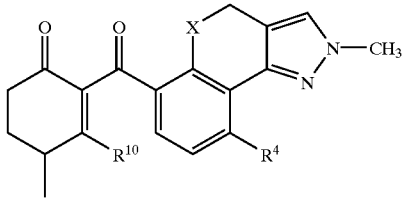
Ia69

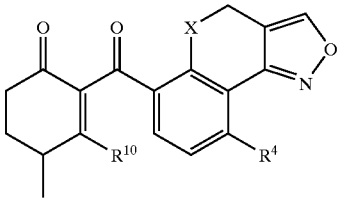
Ia73

Likewise particular preference is given to the compounds of the formula Ia70 (=Ia where $R^1$, $R^2$, $R^5$ and $R^{12}$ to $R^{16}$=H, $R^3$ and $R^{11}$=CH$_3$, m=2), in particular to the compounds Ia70.n, where the variables X, $R^4$ and $R^{10}$ are as defined in Table 1.

Likewise particular preference is given to the compounds of the formula Ia74 (=Ia where $R^1$, $R^2$, $R^5$ and $R^{12}$ to $R^{16}$=H, $R^3$ and $R^{11}$=CH$_3$, m=1), in particular to the compounds Ia74.n, where the variables X, $R^4$ and $R^{10}$ are as defined in Table 1.

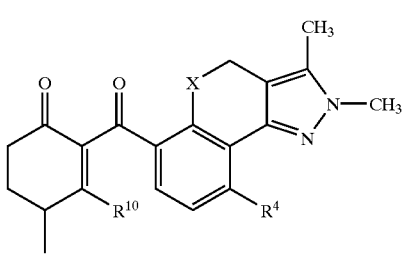
Ia70

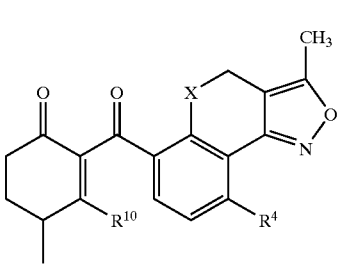
Ia74

Likewise particular preference is given to the compounds of the formula Ia71 (=Ia where $R^1$, $R^2$, $R^5$ and $R^{12}$ to $R^{16}$=H, $R^3$ and $R^{11}$=CH$_3$, m=1), in particular to the compounds Ia71.n, where the variables X, $R^4$ and $R^{10}$ are as defined in Table 1.

Likewise particular preference is given to the compounds of the formula Ia75 (=Ia where $R^1$, $R^2$, $R^5$ and $R^{12}$ to $R^{16}$=H, $R^{11}$=CH$_3$, m=0), in particular to the compounds Ia75.n, where the variables X, $R^4$ and $R^{10}$ are as defined in Table 1.

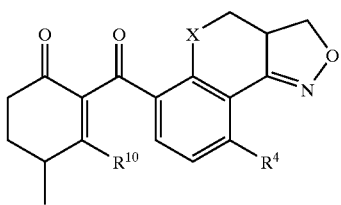

Ia75

Likewise particular preference is given to the compounds of the formula Ia76 (=Ia where $R^1$, $R^2$, $R^5$ and $R^{12}$ to $R^{16}$=H, $R^{11}$=CH$_3$, m=0), in particular to the compounds Ia76.n, where the variables X, $R^4$ and $R^{10}$ are as defined in Table 1.

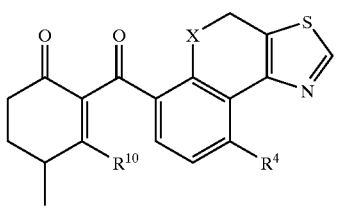

Ia76

Likewise particular preference is given to the compounds of the formula Ia77 (=Ia where $R^1$, $R^2$, $R^5$ and $R^{12}$ to $R^{16}$=H, $R^{11}$=CH$_3$, m=0), in particular to the compounds Ia77.n, where the variables X, $R^4$ and $R^{10}$ are as defined in Table 1.

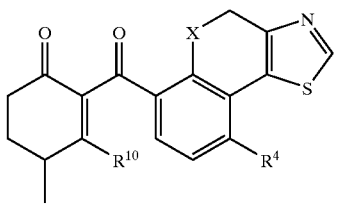

Ia77

Likewise particular preference is given to the compounds of the formula Ia78 (=Ia where $R^1$, $R^2$, $R^5$ and $R^{12}$ to $R^{16}$=H, $R^{11}$=CH$_3$, m=0), in particular to the compounds Ia78.n, where the variables X, $R^4$ and $R^{10}$ are as defined in Table 1.

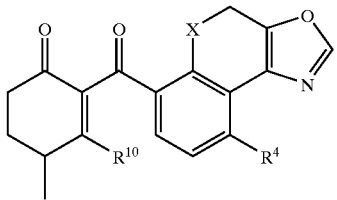

Ia78

Likewise particular preference is given to the compounds of the formula Ia79 (=Ia where $R^1$, $R^2$, $R^5$ and $R^{12}$ to $R^{16}$=H, $R^{11}$=CH$_3$, m=0), in particular to the compounds Ia79.n, where the variables X, $R^4$ and $R^{10}$ are as defined in Table 1.

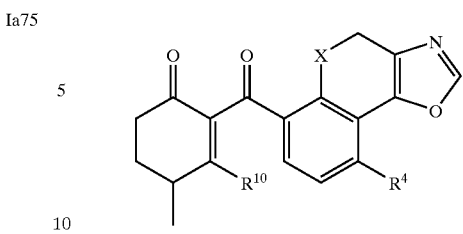

Ia79

Likewise particular preference is given to the compounds of the formula Ia80 (=Ia where $R^1$, $R^2$, $R^5$ and $R^{12}$ to $R^{16}$=H, $R^3$ and $R^{11}$=CH$_3$, m=1), in particular to the compounds Ia80.n, where the variables X, $R^4$ and $R^{10}$ are as defined in Table 1.

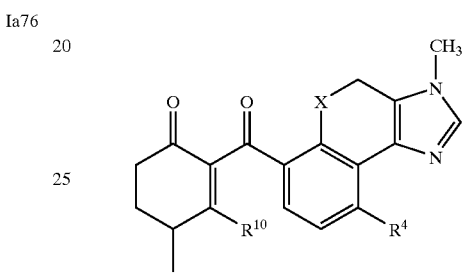

Ia80

Likewise particular preference is given to the compounds of the formula Ia81 (=Ia where $R^1$, $R^2$, $R^5$ and $R^{12}$ to $R^{16}$=H, $R^3$ and $R^{11}$=CH$_3$, m=1), in particular to the compounds Ia81.n, where the variables X, $R^4$ and $R^{10}$ are as defined in Table 1.

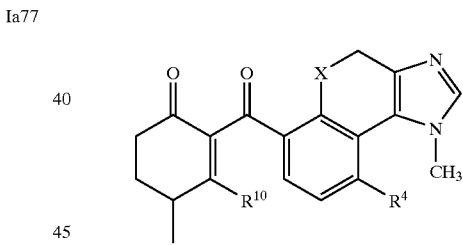

Ia81

Likewise particular preference is given to the compounds of the formula Ia82 (=Ia where $R^1$, $R^2$, $R^5$ and $R^{12}$ to $R^{16}$=H, $R^{11}$=CH$_3$, m=0), in particular to the compounds Ia82.n, where the variables X, $R^4$ and $R^{10}$ are as defined in Table 1.

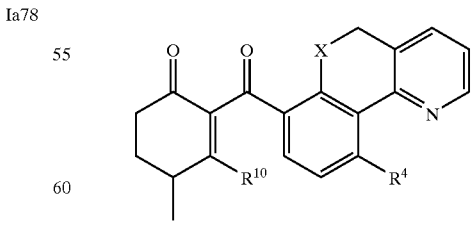

Ia82

Likewise particular preference is given to the compounds of the formula Ia83 (=Ia where $R^1$, $R^2$, $R^5$ and $R^{12}$ to $R^{16}$=H, $R^{11}$=CH$_3$, m=0), in particular to the compounds Ia83.n, where the variables X, $R^4$ and $R^{10}$ are as defined in Table 1.

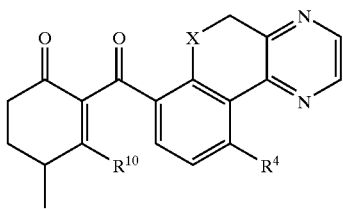
Ia83

Likewise particular preference is given to the compounds of the formula Ia84 (=Ia where $R^1$, $R^2$, $R^5$ and $R^{12}$ to $R^{16}$=H, $R^3$ and $R^{11}$=CH$_3$, m=1), in particular to the compounds Ia62.n, where the variables X, $R^4$ and $R^{10}$ are as defined in Table 1.

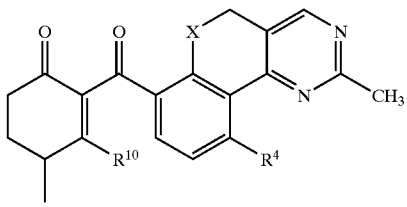
Ia84

Likewise particular preference is given to the compounds of the formula Ia85 (=Ia where $R^1$, $R^2$, $R^5$ and $R^{12}$ to $R^{16}$=H, $R^{11}$=CH$_3$, m=0), in particular to the compounds Ia85.n, where the variables X, $R^4$ and $R^{10}$ are as defined in Table 1.

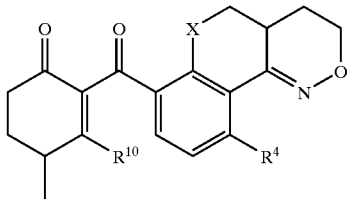
Ia85

Likewise particular preference is given to the compounds of the formula Ia86 (=Ia where $R^1$, $R^2$, $R^5$ and $R^{12}$ to $R^{16}$=H, $R^{11}$=CH$_3$, m=0), in particular to the compounds Ia86.n, where the variables X, $R^4$ and $R^{10}$ are as defined in Table 1.

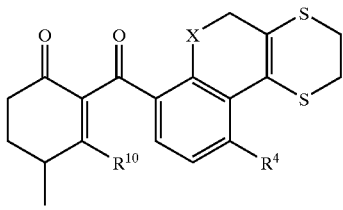
Ia86

Likewise particular preference is given to the compounds of the formula Ia87 (=Ia where $R^1$, $R^2$, $R^5$ and $R^{12}$ to $R^{16}$=H, $R^{11}$=CH$_3$, m=0), in particular to the compounds Ia87.n, where the variables X, $R^4$ and $R^{10}$ are as defined in Table 1.

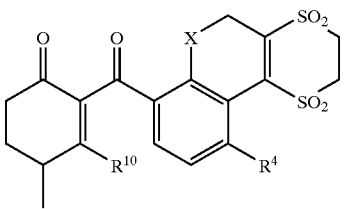
Ia87

Likewise particular preference is given to the compounds of the formula Ia88 (=Ia where $R^1$, $R^2$, $R^5$ and $R^{12}$ to $R^{16}$=H, $R^3$ and $R^{11}$=CH$_3$, m=1), in particular to the compounds Ia88.n, where the variables X, $R^4$ and $R^{10}$ are as defined in Table 1.

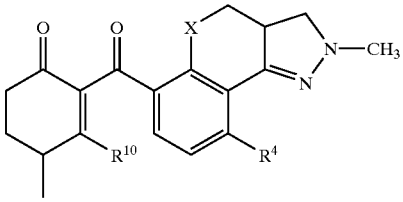
Ia88

Likewise particular preference is given to the compounds of the formula Ia89 (=Ia where $R^1$, $R^2$, $R^5$ and $R^{13}$ to $R^{16}$=H, $R^{11}$ and $R^{12}$=CH$_3$, m=0), in particular to the compounds Ia89.n, where the variables X, $R^4$ and $R^{10}$ are as defined in Table 1.

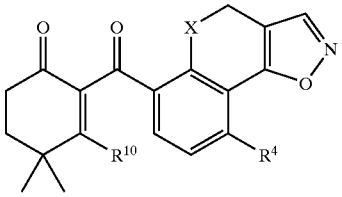
Ia89

Likewise particular preference is given to the compounds of the formula Ia90 (=Ia where $R^1$, $R^2$, $R^5$ and $R^{13}$ to $R^{16}$=H, $R^3$, $R^{11}$ and $R^{12}$=CH$_3$, m=1), in particular to the compounds Ia90.n, where the variables X, $R^4$ and $R^{10}$ are as defined in Table 1.

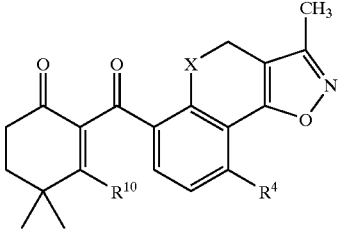
Ia90

Likewise particular preference is given to the compounds of the formula Ia91 (=Ia where $R^1$, $R^2$, $R^5$, $R^{13}$ to $R^{16}$=H, $R^3$, $R^{11}$ and $R^{12}$=CH$_3$, m=1), in particular to the compounds Ia91.n, where the variables X, $R^4$ and $R^{10}$ are as defined in Table 1.

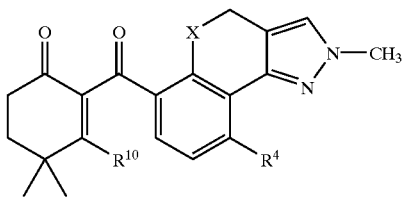
Ia91

Likewise particular preference is given to the compounds of the formula Ia92 (=Ia where $R^1$, $R^2$, $R^5$, $R^{13}$ to $R^{16}$=H, $R^3$, $R^{11}$ and $R^{12}$=CH$_3$, m=2), in particular to the compounds Ia92.n, where the variables X, $R^4$ and $R^{10}$ are as defined in Table 1.

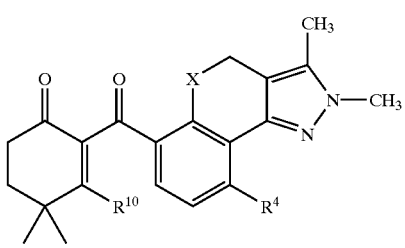
Ia92

Likewise particular preference is given to the compounds of the formula Ia93 (=Ia where $R^1$, $R^2$, $R^5$ and $R^{13}$ to $R^{16}$=H, $R^3$, $R^{11}$ and $R^{12}$=CH$_3$, m=1), in particular to the compounds Ia93.n, where the variables X, $R^4$ and $R^{10}$ are as defined in Table 1.

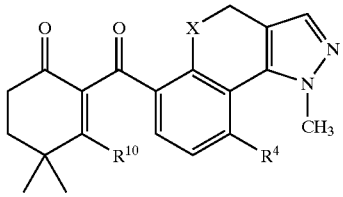
Ia93

Likewise particular preference is given to the compounds of the formula Ia94 (=Ia where $R^1$, $R^2$, $R^5$ and $R^{13}$ to $R^{16}$=H, $R^3$, $R^{11}$ and $R^{12}$=CH$_3$, m=2), in particular to the compounds Ia94.n, where the variables X, $R^4$ and $R^{10}$ are as defined in Table 1.

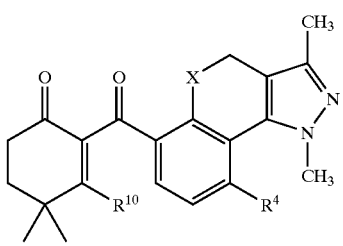
Ia94

Likewise particular preference is given to the compounds of the formula Ia95 (=Ia where $R^1$, $R^2$, $R^5$ and $R^{12}$ to $R^{16}$=H, $R^{11}$ and $R^{12}$=CH$_3$, m=0), in particular to the compounds Ia95.n, where the variables X, $R^4$ and $R^{10}$ are as defined in Table 1.

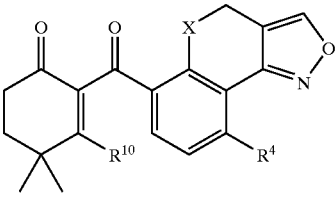
Ia95

Likewise particular preference is given to the compounds of the formula Ia96 (=Ia where $R^1$, $R^2$, $R^5$ and $R^{13}$ to $R^{16}$=H, $R^3$, $R^{11}$ and $R^{12}$=CH$_3$, m=1), in particular to the compounds Ia96.n, where the variables X, $R^4$ and $R^{10}$ are as defined in Table 1.

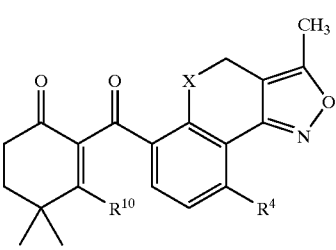
Ia96

Likewise particular preference is given to the compounds of the formula Ia97 (=Ia where $R^1$, $R^2$, $R^5$ and $R^{13}$ to $R^{16}$=H, $R^{11}$ and $R^{12}$=CH$_3$, m=0), in particular to the compounds Ia97.n, where the variables X, $R^4$ and $R^{10}$ are as defined in Table 1.

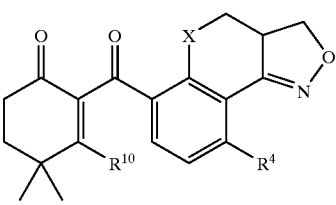
Ia97

Likewise particular preference is given to the compounds of the formula Ia98 (=Ia where $R^1$, $R^2$, $R^5$ and $R^{13}$ to $R^{16}$=H, $R^{11}$ and $R^{12}$=CH$_3$, m=0), in particular to the compounds Ia98.n, where the variables X, $R^4$ and $R^{10}$ are as defined in Table 1.

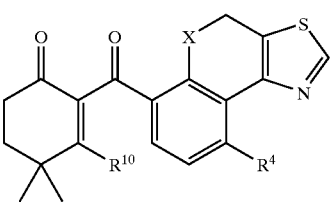
Ia98

Likewise particular preference is given to the compounds of the formula Ia99 (=Ia where $R^1$, $R^2$, $R^5$ and $R^{13}$ to $R^{16}$=H, $R^{11}$ and $R^{12}$=CH$_3$, m=0), in particular to the compounds Ia99.n, where the variables X, $R^4$ to $R^{10}$ are as defined in Table 1.

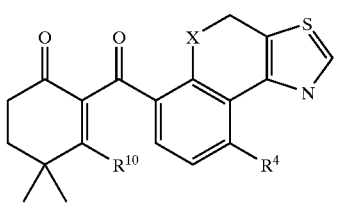

Ia99

Likewise particular preference is given to the compounds of the formula Ia100 (=Ia where $R^1$, $R^2$, $R^5$ and $R^{13}$ to $R^{16}$=H, $R^{11}$ and $R^{12}$=$CH_3$, m=0), in particular to the compounds Ia100.n, where the variables X, $R^4$ and $R^{10}$ are as defined in Table 1.

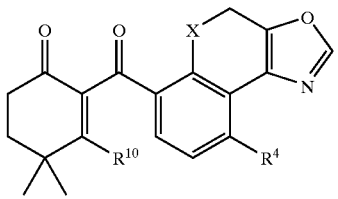

Ia100

Likewise particular preference is given to the compounds of the formula Ia101 (=Ia where $R^1$, $R^2$, $R^5$ and $R^{13}$ to $R^{16}$=H, $R^{11}$ and $R^{12}$=$CH_3$, m=0), in particular to the compounds Ia101.n, where the variables X, $R^4$ and $R^{10}$ are as defined in Table 1.

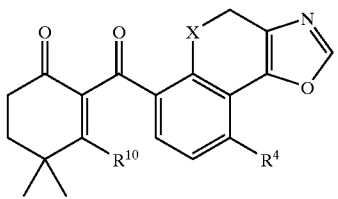

Ia101

Likewise particular preference is given to the compounds of the formula Ia102 (=Ia where $R^1$, $R^2$, $R^5$ and $R^{13}$ to $R^{16}$=H, $R^3$, $R^{11}$ and $R^{12}$=$CH_3$, m=1), in particular to the compounds Ia102.n, where the variables X, $R^4$ and $R^{10}$ are as defined in Table 1.

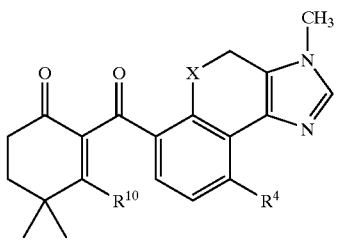

Ia102

Likewise particular preference is given to the compounds of the formula Ia103 (=Ia where $R^1$, $R^2$, $R^5$ and $R^{13}$ to $R^{16}$=H, $R^3$, $R^{11}$ and $R^{12}$=$CH_3$, m=1), in particular to the compounds Ia103.n, where the variables X, $R^4$ and $R^{10}$ are as defined in Table 1.

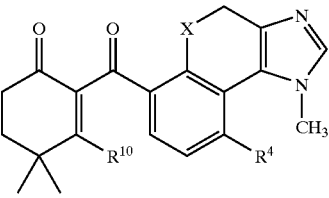

Ia103

Likewise particular preference is given to the compounds of the formula Ia104 (=Ia where $R^1$, $R^2$, $R^5$ and $R^{13}$ to $R^{16}$=H, $R^{11}$ and $R^{12}$=$CH_3$, m=0), in particular to the compounds Ia104.n, where the variables X, $R^4$ and $R^{10}$ are as defined in Table 1.

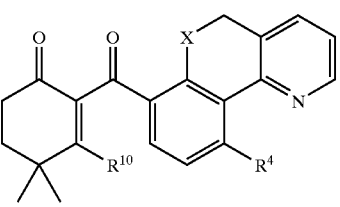

Ia104

Likewise particular preference is given to the compounds of the formula Ia105 (=Ia where $R^1$, $R^2$, $R^5$ and $R^{13}$ to $R^{16}$=H, $R^{11}$ and $R^{12}$=$CH_3$, m=0), in particular to the compounds Ia105.n, where the variables X, $R^4$ and $R^{10}$ are as defined in Table 1.

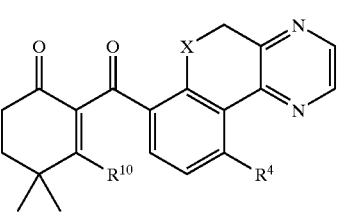

Ia105

Likewise particular preference is given to the compounds of the formula Ia106 (=Ia where $R^1$, $R^2$, $R^5$ and $R^{13}$ to $R^{16}$=H, $R^3$, $R^{11}$ and $R^{12}$=$CH_3$, m=1), in particular to the compounds Ia106.n, where the variables X, $R^4$ and $R^{10}$ are as defined in Table 1.

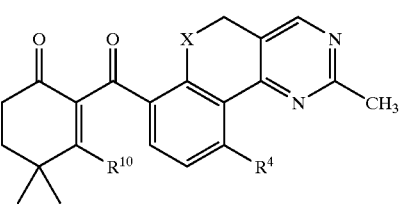

Ia106

Likewise particular preference is given to the compounds of the formula Ia107 (=Ia where $R^1$, $R^2$, $R^5$ and $R^{13}$ to $R^{16}$=H, $R^{11}$ and $R^{12}$=$CH_3$, m=0), in particular to the compounds Ia107.n, where the variables X, $R^4$ and $R^{10}$ are as defined in Table 1.

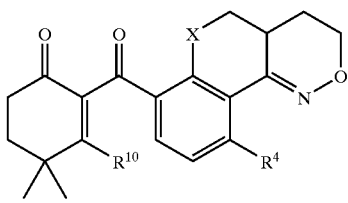

Ia107

Likewise particular preference is given to the compounds of the formula Ia108 (=Ia where $R^1$, $R^2$, $R^5$ and $R^{13}$ to $R^{16}$=H, $R^{11}$ and $R^{12}$=CH$_3$, m=0), in particular to the compounds Ia108.n, where the variables X, $R^4$ and $R^{10}$ are as defined in Table 1.

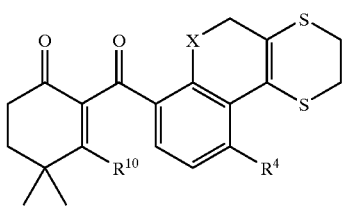

Ia108

Likewise particular preference is given to the compounds of the formula Ia109 (=Ia where $R^1$, $R^2$, $R^5$ and $R^{13}$ to $R^{16}$=H, $R^{11}$ and $R^{12}$=CH$_3$, m=0), in particular to the compounds Ia109.n, where the variables X, $R^4$ and $R^{10}$ are as defined in Table 1.

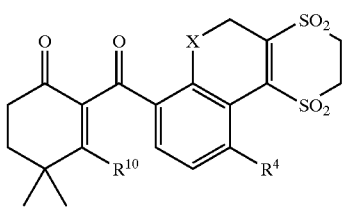

Ia109

Likewise particular preference is given to the compounds of the formula Ia110 (=Ia where $R^1$, $R^2$, $R^5$ and $R^{13}$ to $R^{16}$=H, $R^3$, $R^{11}$ and $R^{12}$=CH$_3$, m=1), in particular to the compounds Ia110.n, where the variables X, $R^4$ and $R^{10}$ are as defined in Table 1.

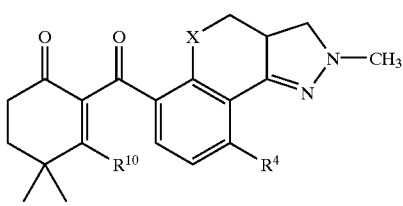

Ia110

Likewise particular preference is given to the compounds of the formula Ia111 (=Ia where $R^1$, $R^2$, $R^5$ and $R^{11}$ to $R^{14}$=H, $R^{15}$ and $R^{16}$=CH$_3$, m=0), in particular to the compounds Ia111.n, where the variables X, $R^4$ and $R^{10}$ are as defined in Table 1.

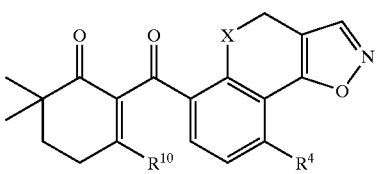

Ia111

Likewise particular preference is given to the compounds of the formula Ia112 (=Ia where $R^1$, $R^2$, $R^5$ and $R^{11}$ to $R^{14}$=H, $R^3$, $R^{15}$ and $R^{16}$=CH$_3$, m=1), in particular to the compounds Ia111.n, where the variables X, $R^4$ and $R^{10}$ are as defined in Table 1.

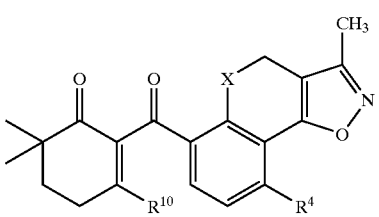

Ia112

Likewise particular preference is given to the compounds of the formula Ia113 (=Ia where $R^1$, $R^2$, $R^5$ and $R^{11}$ to $R^{14}$=H, $R^3$, $R^{15}$ and $R^{16}$=CH$_3$, m=1), in particular to the compounds Ia113.n, where the variables X, $R^4$ and $R^{10}$ are as defined in Table 1.

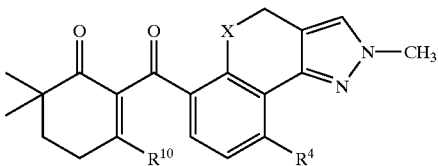

Ia113

Likewise particular preference is given to the compounds of the formula Ia114 (=Ia where $R^1$, $R^2$, $R^5$ and $R^{11}$ to $R^{14}$=H, $R^3$, $R^{15}$ and $R^{16}$=CH$_3$, m=2), in particular to the compounds Ia114.n, where the variables X, $R^4$ and $R^{10}$ are as defined in Table 1.

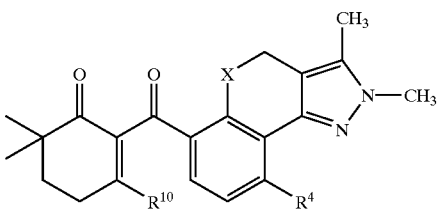

Ia114

Likewise particular preference is given to the compounds of the formula Ia115 (=Ia where $R^1$, $R^2$, $R^5$ and $R^{11}$ to $R^{14}$=H, $R^3$, $R^{15}$ and $R^{16}$=CH$_3$, m=1), in particular to the compounds Ia115.n, where the variables X, $R^4$ and $R^{10}$ are as defined in Table 1.

Likewise particular preference is given to the compounds of the formula Ia116 (=Ia where $R^1$, $R^2$, $R^5$ and $R^{11}$ to $R^{14}$=H, $R^3$, $R^{15}$ and $R^{16}$=CH$_3$, m=2), in particular to the compounds Ia116.n, where the variables X, $R^4$ and $R^{10}$ are as defined in Table 1.

Ia115

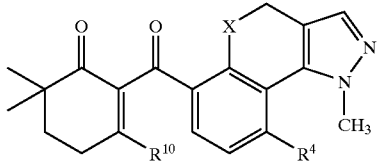

Ia116

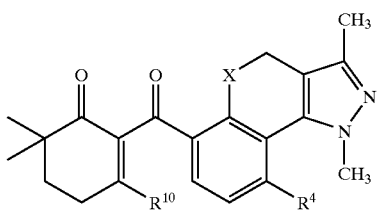

Likewise particular preference is given to the compounds of the formula Ia117 (=Ia where $R^1$, $R^2$, $R^5$ and $R^{11}$ to $R^{14}$=H, $R^{15}$ and $R^{16}$=CH$_3$, m=0), in particular to the compounds Ia117.n, where the variables X, $R^4$ and $R^{10}$ are as defined in Table 1.

Ia117

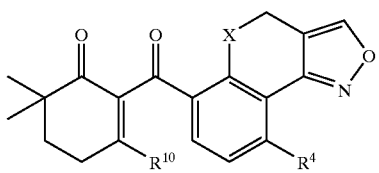

Likewise particular preference is given to the compounds of the formula Ia118 (=Ia where $R^1$, $R^2$, $R^5$ and $R^{11}$ to $R^{14}$=H, $R^3$, $R^{15}$ and $R^{16}$=CH$_3$, m=1), in particular to the compounds Ia118.n, where the variables X, $R^4$ and $R^{10}$ are as defined in Table 1.

Ia118

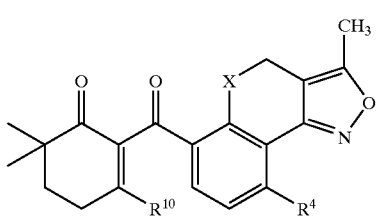

Likewise particular preference is given to the compounds of the formula Ia119 (=Ia where $R^1$, $R^2$, $R^5$ and $R^{11}$ to $R^{14}$=H, $R^{15}$ and $R^{16}$=CH$_3$, m=0), in particular to the compounds Ia119.n, where the variables X, $R^4$ and $R^{10}$ are as defined in Table 1.

Ia119

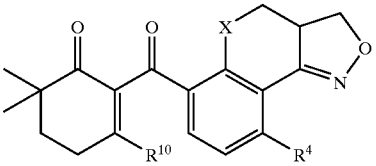

Likewise particular preference is given to the compounds of the formula Ia120 (=Ia where $R^1$, $R^2$, $R^5$ and $R^{11}$ to $R^{14}$=H, $R^{15}$ and $R^{16}$=CH$_3$, m=0), in particular to the compounds Ia120.n, where the variables X, $R^4$ and $R^{10}$ are as defined in Table 1.

Ia120

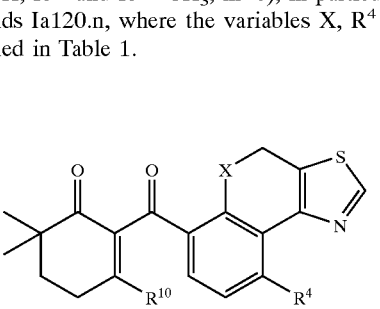

Likewise particular preference is given to the compounds of the formula Ia121 (=Ia where $R^1$, $R^2$, $R^5$ and $R^{11}$ to $R^{14}$=H, $R^{15}$ and $R^{16}$=CH$_3$, m=0), in particular to the compounds Ia121.n, where the variables X, $R^4$ to $R^{10}$ are as defined in Table 1.

Ia121

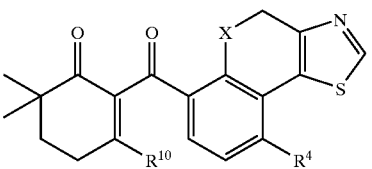

Likewise particular preference is given to the compounds of the formula Ia122 (=Ia where $R^1$, $R^2$, $R^5$ and $R^{11}$ to $R^{14}$=H, $R^{15}$ and $R^{16}$=CH$_3$, m=0), in particular to the compounds Ia122.n, where the variables X, $R^4$ and $R^{10}$ are as defined in Table 1.

Ia122

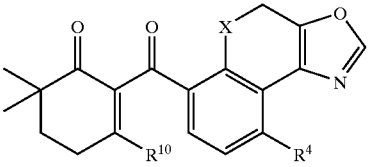

Likewise particular preference is given to the compounds of the formula Ia123 (=Ia where $R^1$, $R^2$, $R^5$ and $R^{11}$ to $R^{14}$=H, $R^{15}$ and $R^{16}$=CH$_3$, m=0), in particular to the compounds Ia123.n, where the variables X, $R^4$ and $R^{10}$ are as defined in Table 1.

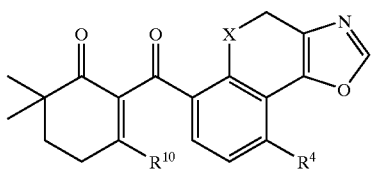

Ia123

Likewise particular preference is given to the compounds of the formula Ia124 (=Ia where $R^1$, $R^2$, $R^5$ and $R^{11}$ to $R^{14}$=H, $R^3$, $R^{15}$ and $R^{16}$=$CH_3$, m=1), in particular to the compounds Ia124.n, where the variables X, $R^4$ and $R^{10}$ are as defined in Table 1.

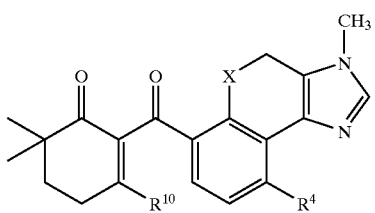

Ia124

Likewise particular preference is given to the compounds of the formula Ia125 (=Ia where $R^1$, $R^2$, $R^5$ and $R^{11}$ to $R^{14}$=H, $R^3$, $R^{15}$ and $R^{16}$=$CH_3$, m=1), in particular to the compounds Ia125.n, where the variables X, $R^4$ and $R^{10}$ are as defined in Table 1.

Ia125

Likewise particular preference is given to the compounds of the formula Ia126 (=Ia where $R^1$, $R^2$, $R^5$ and $R^{11}$ to $R^{14}$=H, $R^{15}$ and $R^{16}$=$CH_3$, m=0), in particular to the compounds Ia126.n, where the variables X, $R^4$ and $R^{10}$ are as defined in Table 1.

Ia126

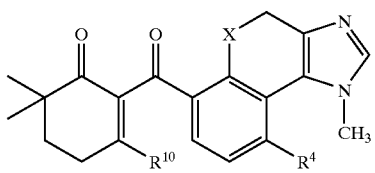

Likewise particular preference is given to the compounds of the formula Ia127 (=Ia where $R^1$, $R^2$, $R^5$ and $R^{11}$ to $R^{14}$=H, $R^{15}$ and $R^{16}$=$CH_3$, m=0), in particular to the compounds Ia127.n, where the variables X, $R^4$ and $R^{10}$ are as defined in Table 1.

Ia127

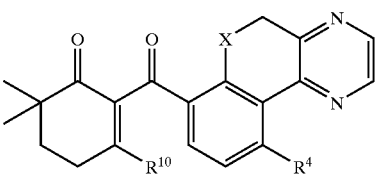

Likewise particular preference is given to the compounds of the formula Ia128 (=Ia where $R^1$, $R^2$, $R^5$ and $R^{11}$ to $R^{14}$=H, $R^3$, $R^{15}$ and $R^{16}$=$CH_3$, m=1), in particular to the compounds Ia128.n, where the variables X, $R^4$ and $R^{10}$ are as defined in Table 1.

Ia128

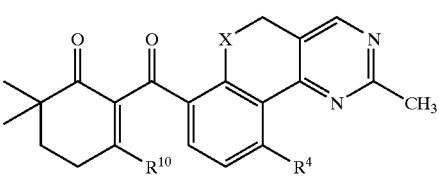

Likewise particular preference is given to the compounds of the formula Ia129 (=Ia where $R^1$, $R^2$, $R^5$ and $R^{11}$ to $R^{14}$=H, $R^{15}$ and $R^{16}$=$CH_3$, m=0), in particular to the compounds Ia129.n, where the variables X, $R^4$ and $R^{10}$ are as defined in Table 1.

Ia129

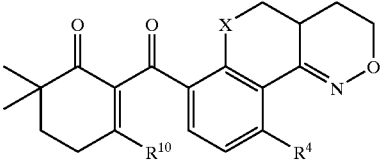

Likewise particular preference is given to the compounds of the formula Ia130 (=Ia where $R^1$, $R^2$, $R^5$ and $R^{11}$ to $R^{14}$=H, $R^{15}$ and $R^{16}$=$CH_3$, m=0), in particular to the compounds Ia130.n, where the variables X, $R^4$ and $R^{10}$ are as defined in Table 1.

Ia130

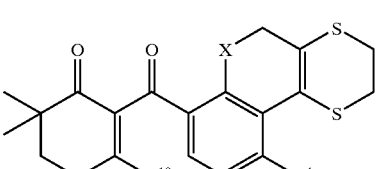

Likewise particular preference is given to the compounds of the formula Ia131 (=Ia where $R^1$, $R^2$, $R^5$ and $R^{11}$ to $R^{14}$=H, $R^{15}$ and $R^{16}$=$CH_3$, m=0), in particular to the compounds Ia131.n, where the variables X, $R^4$ and $R^{10}$ are as defined in Table 1.

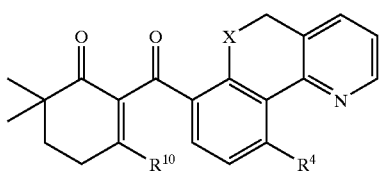

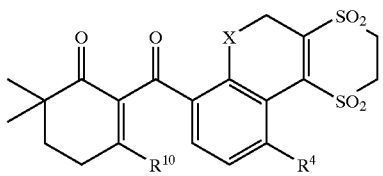
Ia131

Likewise particular preference is given to the compounds of the formula Ia132 (=Ia where $R^1$, $R^2$, $R^5$ and $R^{11}$ to $R^{14}$=H, $R^3$, $R^{15}$ and $R^{16}$=CH$_3$, m=1), in particular to the compounds Ia132.n, where the variables X, $R^4$ and $R^{10}$ are as defined in Table 1.

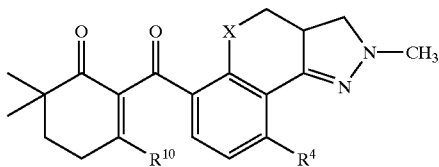
Ia132

Likewise particular preference is given to the compounds of the formula Ia133 (=Ia where $R^1$, $R^2$ and $R^5$=H, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia133.n, where the variables X, $R^4$ and $R^{10}$ are as defined in Table I [sic].

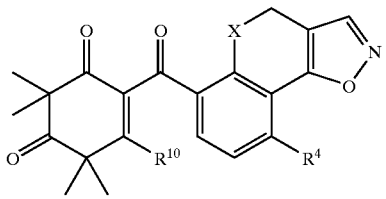
Ia133

Likewise particular preference is given to the compounds of the formula Ia134 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia134.n, where the variables X, $R^4$ and $R^{10}$ are as defined in Table 1.

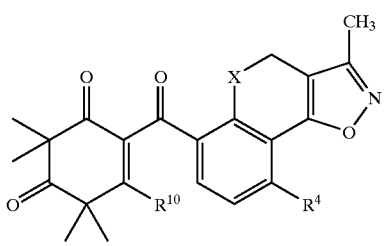
Ia134

Likewise particular preference is given to the compounds of the formula Ia135 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia135.n, where the variables X, $R^4$ and $R^{10}$ are as defined in Table 1.

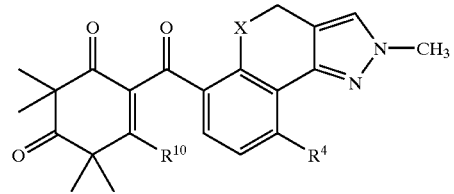
Ia135

Likewise particular preference is given to the compounds of the formula Ia136 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=2), in particular to the compounds Ia136.n, where the variables X, $R^4$ and $R^{10}$ are as defined in Table 1.

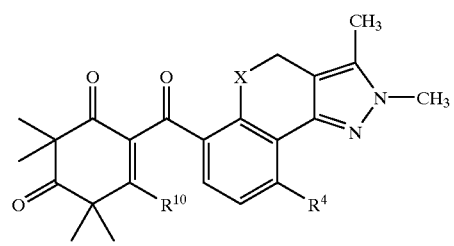
Ia136

Likewise particular preference is given to the compounds of the formula Ia37 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia137.n, where the variables X, $R^4$ and $R^{10}$ are as defined in Table 1.

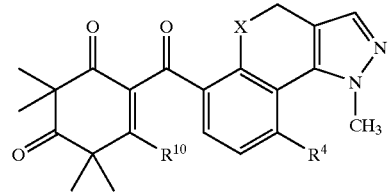
Ia137

Likewise particular preference is given to the compounds of the formula Ia138 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=2), in particular to the compounds Ia138.n, where the variables X, $R^4$ and $R^{10}$ are as defined in Table 1.

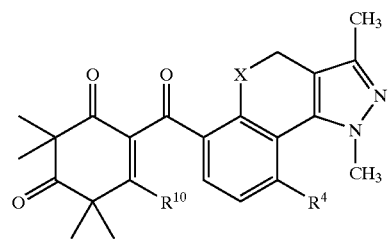
Ia138

Likewise particular preference is given to the compounds of the formula Ia139 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia139.n, where the variables X, $R^4$ and $R^{10}$ are as defined in Table 1.

Ia139

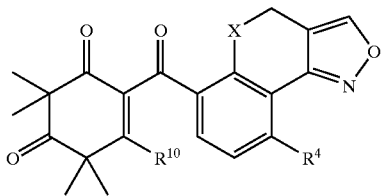

Likewise particular preference is given to the compounds of the formula Ia140 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia140.n, where the variables X, $R^4$ and $R^{10}$ are as defined in Table 1.

Ia140

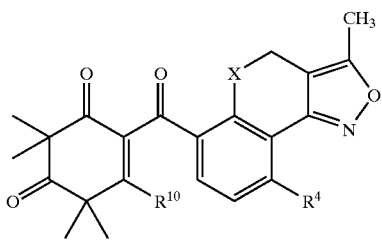

Likewise particular preference is given to the compounds of the formula Ia141 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia141.n, where the variables X, $R^4$ and $R^{10}$ are as defined in Table 1.

Ia141

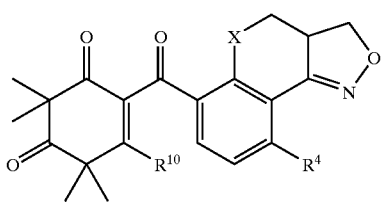

Likewise particular preference is given to the compounds of the formula Ia142 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia142.n, where the variables X, $R^4$ and $R^{10}$ are as defined in Table 1.

Ia142

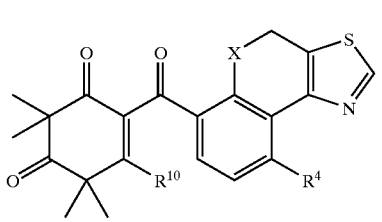

Likewise particular preference is given to the compounds of the formula Ia143 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia143.n, where the variables X, $R^4$ and $R^{10}$ are as defined in Table 1.

Ia143

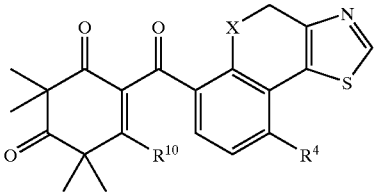

Likewise particular preference is given to the compounds of the formula Ia144 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia144.n, where the variables X, $R^4$ and $R^{10}$ are as defined in Table 1.

Ia144

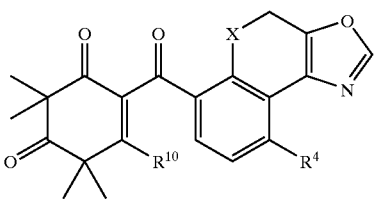

Likewise particular preference is given to the compounds of the formula Ia145 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia145.n, where the variables X, $R^4$ and $R^{10}$ are as defined in Table 1.

Ia145

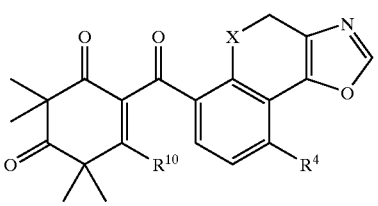

Likewise particular preference is given to the compounds of the formula Ia146 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia146.n, where the variables X, $R^4$ and $R^{10}$ are as defined in Table 1.

Ia146

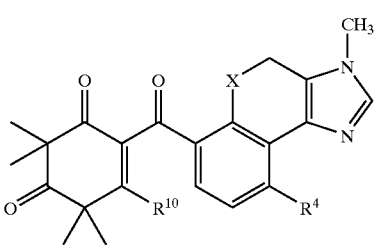

Likewise particular preference is given to the compounds of the formula Ia147 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia147.n, where the variables X, $R^4$ and $R^{10}$ are as defined in Table 1.

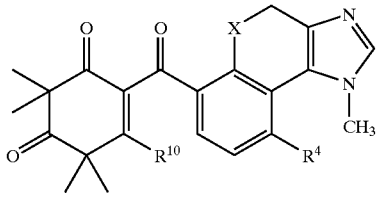

Ia147

Likewise particular preference is given to the compounds of the formula Ia148 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia148.n, where the variables X, $R^4$ and $R^{10}$ are as defined in Table 1.

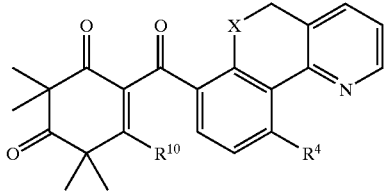

Ia148

Likewise particular preference is given to the compounds of the formula Ia149 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia149.n, where the variables X, $R^4$ and $R^{10}$ are as defined in Table 1.

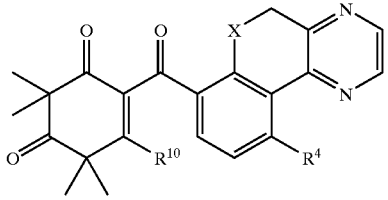

Ia149

Likewise particular preference is given to the compounds of the formula Ia150 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia150.n, where the variables X, $R^4$ and $R^{10}$ are as defined in Table 1.

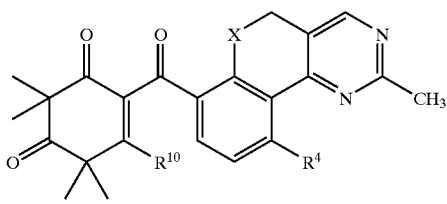

Ia150

Likewise particular preference is given to the compounds of the formula Ia151 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia151.n, where the variables X, $R^4$ and $R^{10}$ are as defined in Table 1.

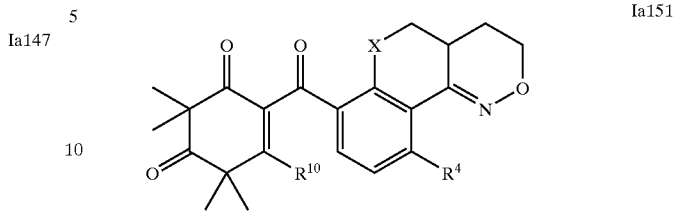

Ia151

Likewise particular preference is given to the compounds of the formula Ia152 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia152.n, where the variables X, $R^4$ and $R^{10}$ are as defined in Table 1.

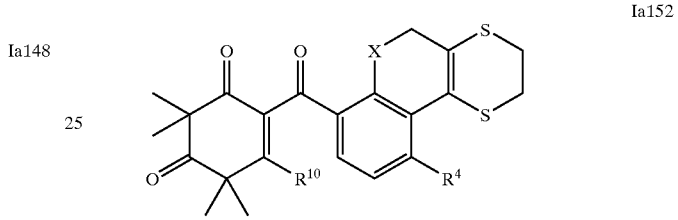

Ia152

Likewise particular preference is given to the compounds of the formula Ia153 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=0), in particular to the compounds Ia153.n, where the variables X, $R^4$ and $R^{10}$ are as defined in Table 1.

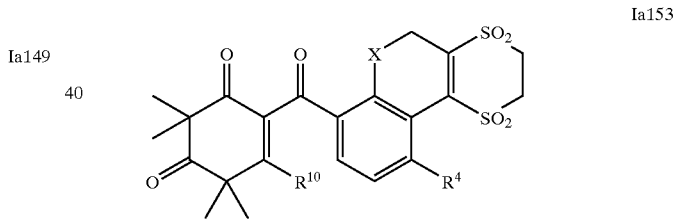

Ia153

Likewise particular preference is given to the compounds of the formula Ia154 (=Ia where $R^1$, $R^2$ and $R^5$=H, $R^3$, $R^{11}$, $R^{12}$, $R^{15}$ and $R^{16}$=CH$_3$, $R^{13}$ and $R^{14}$ together with the carbon to which they are attached form a carbonyl group, m=1), in particular to the compounds Ia154.n, where the variables X, $R^4$ and $R^{10}$ are as defined in Table 1.

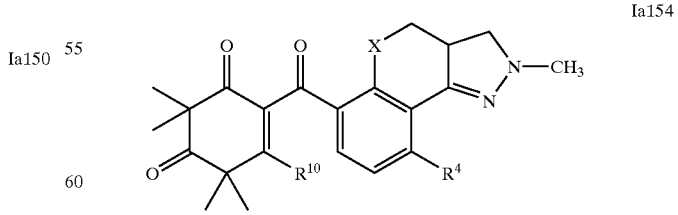

Ia154

Likewise particular preference is given to the compounds of the formula Ia155 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia155.n, where the variables X, $R^4$ and $R^{10}$ are as defined in Table 1.

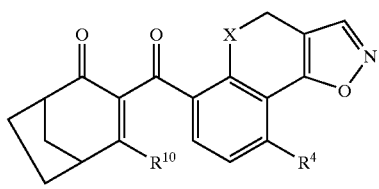

Ia155

Likewise particular preference is given to the compounds of the formula Ia156 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=1), in particular to the compounds Ia156.n, where the variables X, $R^4$ and $R^{10}$ are as defined in Table I [sic].

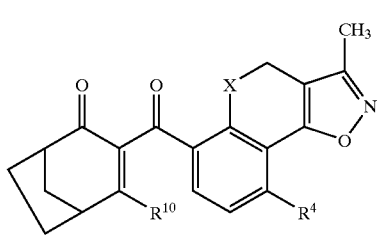

Ia156

Likewise particular preference is given to the compounds of the formula Ia157 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=1), in particular to the compounds Ia157.n, where the variables X, $R^4$ and $R^{10}$ are as defined in Table I [sic].

Ia157

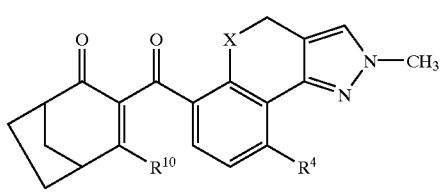

Likewise particular preference is given to the compounds of the formula Ia158 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=2), in particular to the compounds Ia158.n, where the variables X, $R^4$ and $R^{10}$ are as defined in Table I [sic].

Ia158

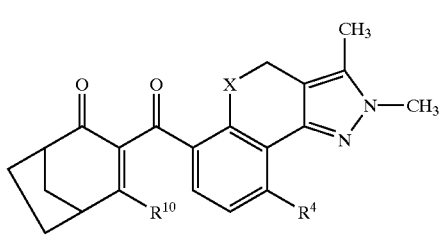

Likewise particular preference is given to the compounds of the formula Ia159 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=1), in particular to the compounds Ia159.n, where the variables X, $R^4$ and $R^{10}$ are as defined in Table I [sic].

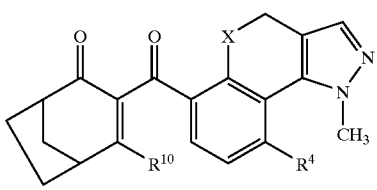

Ia159

Likewise particular preference is given to the compounds of the formula Ia160 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=2), in particular to the compounds Ia160.n, where the variables X, $R^4$ and $R^{10}$ are as defined in Table I [sic].

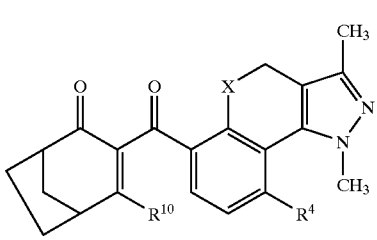

Ia160

Likewise particular preference is given to the compounds of the formula Ia161 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia161.n, where the variables X, $R^4$ and $R^{10}$ are as defined in Table I [sic].

Ia161

Likewise particular preference is given to the compounds of the formula Ia162 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=1), in particular to the compounds Ia162.n, where the variables X, $R^4$ and $R^{10}$ are as defined in Table I [sic].

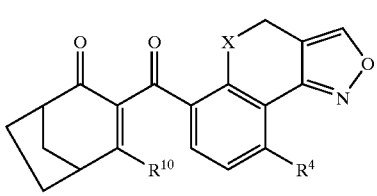

Ia162

Likewise particular preference is given to the compounds of the formula Ia163 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia163.n, where the variables X, $R^4$ and $R^{10}$ are as defined in Table I [sic].

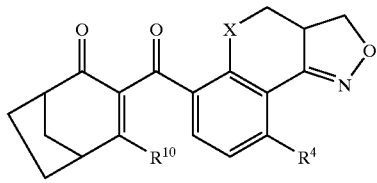

Ia163

Likewise particular preference is given to the compounds of the formula Ia164 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia164.n, where the variables X, $R^4$ and $R^{10}$ are as defined in Table I [sic].

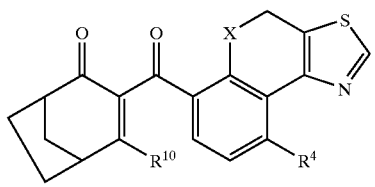

Ia164

Likewise particular preference is given to the compounds of the formula Ia165 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia165.n, where the variables X, $R^4$ and $R^{10}$ are as defined in Table I [sic].

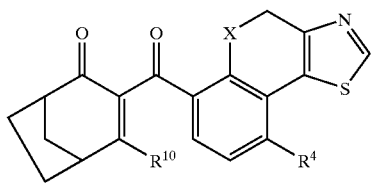

Ia165

Likewise particular preference is given to the compounds of the formula Ia166 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia166.n, where the variables X, $R^4$ and $R^{10}$ are as defined in Table I [sic].

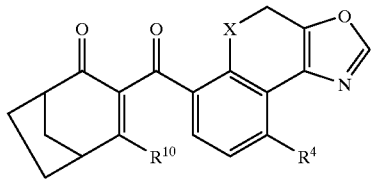

Ia166

Likewise particular preference is given to the compounds of the formula Ia167 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia167.n, where the variables X, $R^4$ and $R^{10}$ are as defined in Table I [sic].

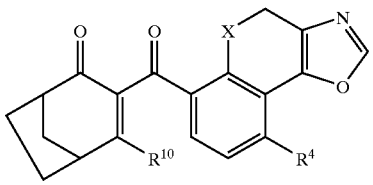

Ia167

Likewise particular preference is given to the compounds of the formula Ia168 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=1), in particular to the compounds Ia168.n, where the variables X, $R^4$ and $R^{10}$ are as defined in Table I [sic].

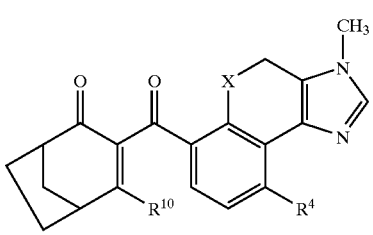

Ia168

Likewise particular preference is given to the compounds of the formula Ia169 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=1), in particular to the compounds Ia169.n, where the variables X, $R^4$ and $R^{10}$ are as defined in Table I [sic].

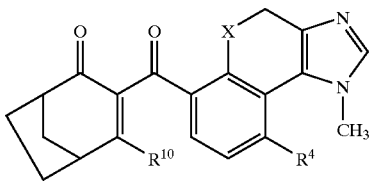

Ia169

Likewise particular preference is given to the compounds of the formula Ia170 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia170.n, where the variables X, $R^4$ and $R^{10}$ are as defined in Table I [sic].

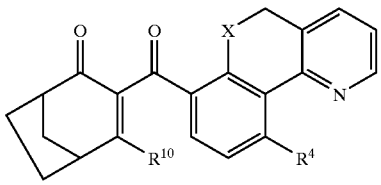

Ia170

Likewise particular preference is given to the compounds of the formula Ia171 (=Ia where $R^1$, $R^2$, $R^5$ and $R^{11}$, $R^{13}$ to $R^{15}$=H, $R^{12}$ and $R^{16}$ together form a —(CH$_2$)$_2$— chain, m=0), in particular to the compounds Ia171.n, where the variables X, $R^4$ and $R^{10}$ are as defined in Table I [sic].

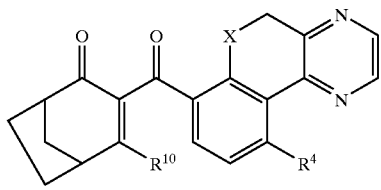
Ia171

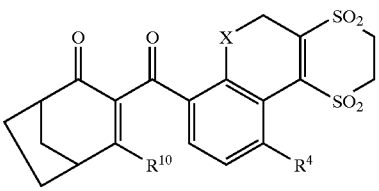
Ia175

Likewise particular preference is given to the compounds of the formula Ia172 (=Ia where $R^1$, $R^2$, $R^5$ and $R^{11}$, $R^{13}$ to $R^{15}$=H, $R^{12}$ and $R^{16}$ together form a —$(CH_2)_2$— chain, m=1), in particular to the compounds Ia172.n, where the variables X, $R^4$ and $R^{10}$ are as defined in Table I [sic].

Likewise particular preference is given to the compounds of the formula Ia176 (=Ia where $R^1$, $R^2$, $R^5$ and $R^{11}$, $R^{13}$ to $R^{15}$=H, $R^{12}$ and $R^{16}$ together form a —$(CH_2)_2$— chain, m=1), in particular to the compounds Ia176.n, where the variables X, $R^4$ and $R^{10}$ are as defined in Table I [sic].

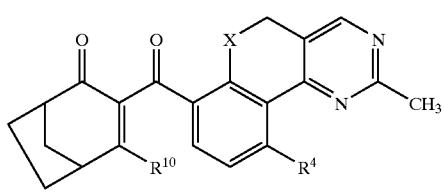
Ia172

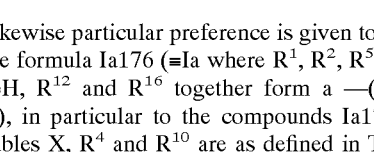
Ia176

Likewise particular preference is given to the compounds of the formula Ia173 (=Ia where $R^1$, $R^2$, $R^5$ and $R^{11}$, $R^{13}$ to $R^{15}$=H, $R^{12}$ and $R^{16}$ together form a —$(CH_2)_2$— chain, m=0), in particular to the compounds Ia173.n, where the variables X, $R^4$ and $R^{10}$ are as defined in Table I [sic].

The tricyclic benzoylcyclohexanedione derivatives of the formula I can be obtained by various routes, for example by one of the following processes:

A. Preparation of compounds of the formula I where $R^{10}$=halogen by reacting a tricyclic benzoylcyclohexanedione derivative of the formula Iα (=I where $R^{10}$=hydroxyl) with a halogenating agent:

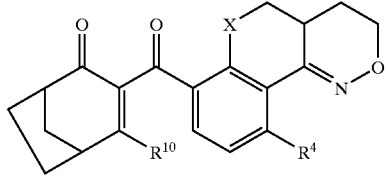
Ia173

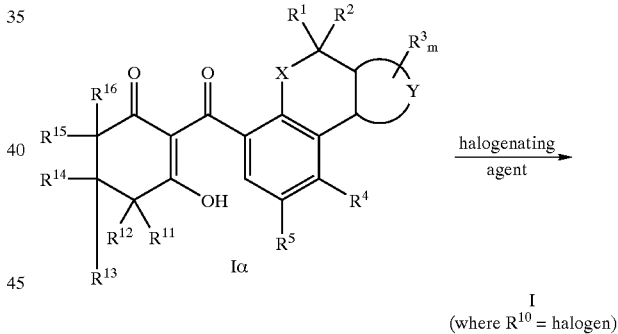

(where $R^{10}$ = halogen)

Likewise particular preference is given to the compounds of the formula Ia174 (=Ia where $R^1$, $R^2$, $R^5$ and $R^{11}$, $R^{13}$ to $R^{15}$=H, $R^{12}$ and $R^{16}$ together form a —$(CH_2)_2$— chain, m=0), in particular to the compounds Ia174.n, where the variables X, $R^4$ and $R^{10}$ are as defined in Table I [sic].

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

The starting materials are generally employed [lacuna] equimolar amounts. However, it may also be advantageous to employ an excess of one or the other component.

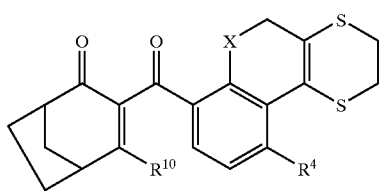
Ia174

Suitable solvents are, for example, chlorinated hydrocarbons, such as methylene chloride or 1,2-dichloroethane, aromatic hydrocarbons, for example toluene, xylene or chlorobenzene, polar aprotic solvents, such as acetonitrile, dimethylformamide or dimethyl sulfoxide, or mixtures of these. However, it is also possible to carry out the reaction in the absence of solvent.

Likewise particular preference is given to the compounds of the formula Ia175 (=Ia where $R^1$, $R^2$, $R^5$ and $R^{11}$, $R^{13}$ to $R^{15}$=H, $R^{12}$ and $R^{16}$ together form a —$(CH_2)_2$— chain, m=0), in particular to the compounds Ia175.n, where the variables X, $R^4$ and $R^{10}$ are as defined in Table I [sic].

The reaction temperature is generally in the range from 0° C. to the boiling point of the reaction mixture.

Work-up can be carried out in a manner known per se to afford the product.

B. Preparation of compounds of the formula I where $R^{10}=OR^{17}$ or $OSO_2R^{18}$, by reacting a tricyclic benzoylcyclohexanedione derivative of the formula Iα (=I where $R^{10}$=hydroxyl) with an alkylating agent IIIα or a sulfonylating agent IIIβ.

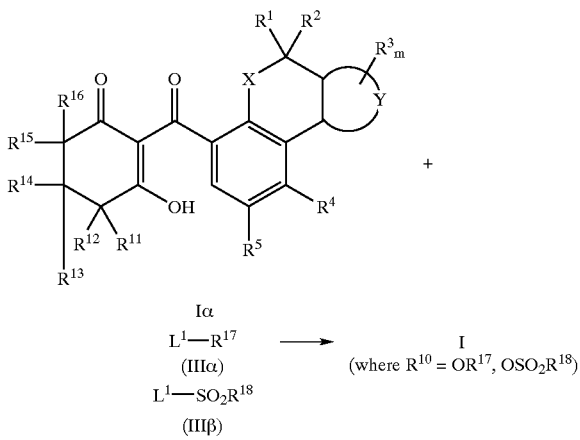

$L^1$ is a nucleophilically replaceable leaving group, such as halogen, for example chlorine or bromine, hetaryl, for example imidazolyl, carboxylate, for example acetate, or sulfonate, for example mesylate or triflate, etc.

The compounds of the formula IIIα or IIIβ can be employed directly, such as, for example, in the case of the carbonyl halides, or be generated in situ, for example activated carboxylic acids (using carboxylic acid and dicyclohexylcarbodiimide etc.).

The starting materials are generally employed in equimolar amounts. However, it may also be advantageous to employ an excess of one or the other component.

If appropriate, it may also be advantageous to carry out the reaction in the presence of a base. Here, the reactants and the base are advantageously employed in equimolar amounts. In certain cases, an excess of base, for example from 1.5 to 3 molar equivalents, may be advantageous.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

The reaction temperature is generally in the range from 0° C. to the boiling point of the reaction mixture.

Work-up can be carried out in a manner known per se to afford the product.

C. Preparation of compounds of the formula I where $R^{10}=OR^{17}$, $SR^{17}$, $OSO_2R^{18}$, $NR^{19}R^{20}$ or N-bonded heterocyclyl by reacting compounds of the formula Iβ (=I where $R^{10}$=halogen) with a compound of the formula IVα, IVβ, IVγ, IVδ or IVε, if appropriate in the presence of a base or with prior formation of salt.

| | | | |
|---|---|---|---|
| Iβ + | $HOR^{17}$ or $HSR^{17}$ or $HOSO_2R^{18}$ or $HNR^{19}R^{20}$ or H(N-bonded heterocyclyl) | IVα IVβ IVγ IVδ IVε | → I(where $R^{10}$ = $OR^{17}$, $SR^{17}$, $OSO_2R^{18}$, $NR^{19}R^{20}$ or N-bonded heterocyclyl) |

The starting materials are generally employed in equimolar amounts. However, it may also be advantageous to employ an excess of one or the other component.

If appropriate, it may also be advantageous to carry out the reaction in the presence of a base. Here, the reactants and the base are advantageously employed in equimolar amounts. An excess of base, for example can [sic] 1.5 to 3 molar equivalents, based on Iβ (where $R^{10}$=halogen), may be advantageous in certain cases.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using sodium hydride or potassium tert-butoxide.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or mixtures of these.

The reaction temperature is generally in the range from 0° C. to the boiling point of the reaction mixture.

Work-up can be carried out in a manner known per se to afford the product.

D. Preparation of compounds of the formula I where $R^{10}=SOR^{18}$, $SO_2R^{18}$, by reacting compounds of the formula I where $R^{10}=SR^{18}$ (Iγ) with an oxidizing agent.

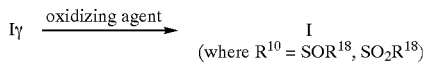

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

The starting materials are generally employed in equimolar amounts. However, it may also be advantageous to employ an excess of one or the other component.

Suitable solvents are, for example, chlorinated hydrocarbons, such as methylene chloride or 1,2-dichloroethane, aromatic hydrocarbons, for example, toluene, xylene or chlorobenzene, ethers, such as diethyl ether, methyltert-butyl ether, tetrahydrofuran or dioxane, polar aprotic solvents, such as acetonitrile or dimethylformamide, or esters, such as ethyl acetate, or mixtures of these.

The reaction temperature is generally in the range from 0° C. to the boiling point of the reaction mixture.

Work-up can be carried out in a manner known per se to afford the product.

E. Preparation of compounds of the formula Iα (=I where R¹⁰=hydroxyl) by reacting an activated tricyclic benzoic acid of the formula VIα or a tricyclic benzoic acid VIβ, preferably activated in situ, with a cyclohexanedione of the formula V to give the acylation product VII, followed by rearrangement.

reactants and the auxiliary base are advantageously employed in equimolar amounts. A slight excess of auxiliary base, for example from 1.2 to 1.5 molar equivalents, based on VI, may be advantageous in certain cases.

Suitable auxiliary bases are tertiary alkylamines, pyridine, or alkali metal carbonates. Suitable solvents are, for example, chlorinated hydrocarbons, such as methylene chloride or 1,2-dichloroethane, aromatic hydrocarbons, such as

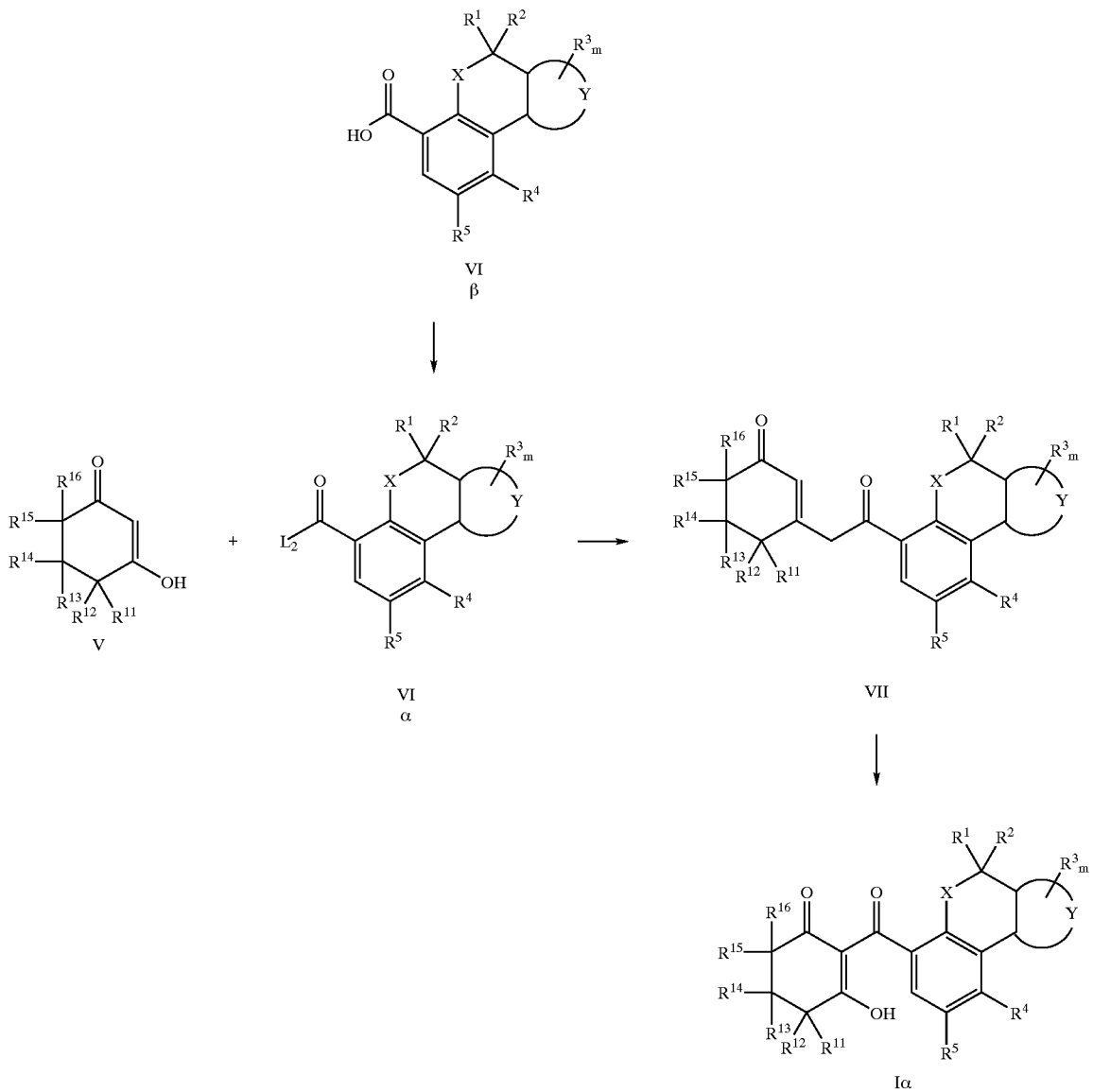

$L^2$ is a nucleophilically replaceable leaving group, such as halogen, for example bromine or chlorine, hetaryl, for example imidazolyl or pyridyl, carboxylate, for example acetate or trifluoroacetate, etc.

The activated tricyclic benzoic acid VIa can be employed directly, such as in the case of the tricyclic benzoyl halides, or be generated in situ, for example using dicyclohexylcarbodiimide, triphenylphosphine/ azodicarboxylic ester, 2-pyridine disulfide/ triphenylphosphine, carbonyldiimidazole, etc.

If appropriate, it may be advantageous to carry out the acylation reaction in the presence of a base. Here, the toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

If tricyclic benzoyl halides are employed as activated carboxylic acid components, it may be advantageous to cool the reaction mixture to 0–10° C. when adding this reaction partner. The mixture is subsequently stirred at 20–100° C., preferably at 25–50° C., until the reaction has gone to completion. Work-up is carried out in a customary manner, for example by pouring the reaction mixture into water and extracting the product of value. Solvents which are suitable for this purpose are, in particular, methylene chloride, diethyl ether and ethyl acetate. The organic phase is dried and the solvent removed, and the crude ester can then be employed for the rearrangement without further purification.

The rearrangement of the esters VII to give the compounds of the formula Iα is advantageously carried out at from 20 to 100° C. in a solvent and in the presence of a base and, if appropriate, using a cyano compound as catalyst.

Solvents which may be used are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in equimolar amounts or in an up to fourfold excess, based on the ester. Preference is given to using triethylamine or alkali metal carbonate, preferably in double the equimolar ratio, based on the ester.

Suitable cyano compounds are inorganic cyanides, such as sodium cyanide or potassium cyanide, and organic cyano compounds, such as acetone cyanohydrin or trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up may be carried out in a manner known per se. The reaction mixture is, for example, acidified using dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, the extract being dried and concentrated.

The tricyclic benzoyl halides of the formula VIα where $L^2$=Cl, Br can be prepared in a manner known per se by reacting the tricyclic benzoic acids of the formula VIβ (≡VIb) with halogenating reagents such as thionyl chloride, thionyl bromide, phosgene, diphosgene, triphosgene, oxalyl chloride and oxalyl bromide.

In a known manner, the tricyclic benzoic acids of the formula VIβ (≡VIb) can be prepared by acidic or basic hydrolysis from the corresponding esters VIc.

Tricyclic benzoic acid derivatives of the formula VI

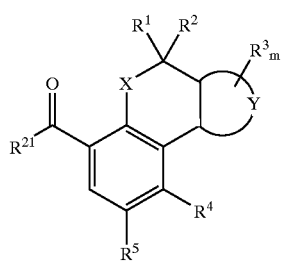

VI where:

X is oxygen, sulfur, S=O, S(=O)$_2$, CR$^6$R$^7$, NR$^8$ or a bond;

Y together with the two carbons to which it is attached forms a saturated, partially saturated or unsaturated 5- or 6-membered heterocycle which contains one to three identical or different heteroatoms selected from the following group: oxygen, sulfur or nitrogen;

$R^1, R^2, R^6, R^7$ are hydrogen, $C_1$–$C_6$-alkyl, $C_1$–$C_6$-haloalkyl, $C_1$–$C_6$-alkoxy or $C_1$–$C_6$-haloalkoxy;

$R^3$ is halogen, $C_1$–$C_6$-alkyl, $C_1$–$C_6$-haloalkyl, $C_1$–$C_6$-alkoxy or $C_1$–$C_6$-haloalkoxy;

$R^4$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)-aminosulfonyl, N,N-di($C_1$–$C_6$-alkyl)aminosulfonyl, N—($C_1$–$C_6$-alkylsulfonyl)amino, N—($C_1$–$C_6$-haloalkylsulfonyl)amino, N—($C_1$–$C_6$-alkyl)-N—($C_1$–$C_6$-alkylsulfonyl)amino or N—($C_1$–$C_6$-alkyl)-N—($C_1$–$C_6$-haloalkylsulfonyl)amino;

$R^5$ is hydrogen, $C_1$–$C_6$-alkyl or halogen;

$R^8$ is hydrogen, $C_1$–$C_6$-alkyl, $C_1$–$C_6$-haloalkyl, $C_1$–$C_6$-alkylcarbonyl, formyl, $C_1$–$C_6$-alkoxycarbonyl, $C_1$–$C_6$-haloalkoxycarbonyl, $C_1$–$C_6$-alkylsulfonyl or $C_1$–$C_6$-haloalkylsulfonyl;

m is 0, 1 or 2;

$R^{21}$ is hydroxyl or a radical which can be removed by hydrolysis;

are novel and also form part of the subject matter of the invention.

Examples of radicals which can be removed by hydrolysis are alkoxy, phenoxy, alkylthio and phenylthio radicals which can be unsubstituted or substituted, halides, heteroaryl radicals which are attached via nitrogen, amino and imino radicals which may be unsubstituted or substituted, etc.

Preference is given to tricyclic benzoyl halides VIa (VI where $R^{21}$=halogen)

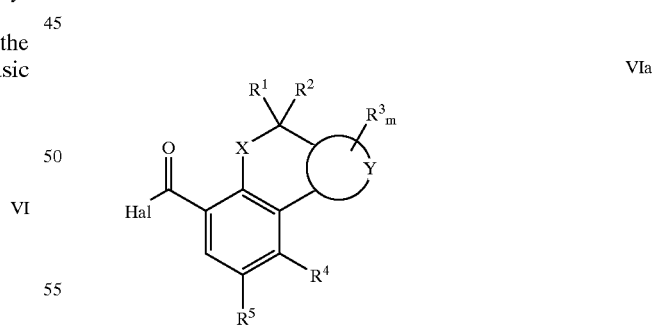

VIa where the variables X, Y, $R^1$ to $R^5$ and m are as defined under formula VI and Hal is halogen, in particular chloride or bromide.

Preference is also given to tricyclic benzoic acids of the formula VIb (VI where $R^{17}$ [sic]=hydroxyl; VIγ),

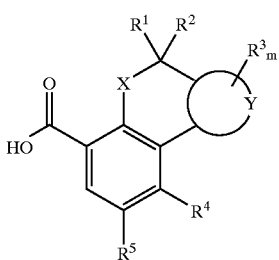

VIb where the variables X, Y, $R^1$ to $R^5$ and m are as defined under formula VI.

Preference is also given to tricyclic benzoic esters of the formula VIc (VI where $R^{21}$=T=$C_1$–$C_6$-alkoxy),

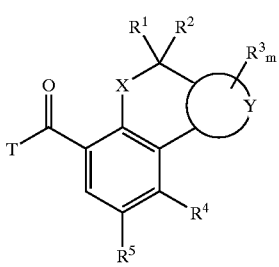

VIc where
the variables X, Y, $R^1$ to $R^5$ and m are as defined under formula VI and
T is $C_1$–$C_6$-alkoxy.

With respect to the variables X, Y, $R^1$ to $R^5$ and m, the particularly preferred embodiments of the tricyclic benzoic acid derivatives of the formulae VI, VIa, VIb and VIc correspond to those of the tricyclic benzoylcyclohexanedione derivatives of the formula I.

Particular preference is given to the compounds VI, VIa, VIb and VIc where Y together with the two carbons to which it is attached forms the following heterocycles:

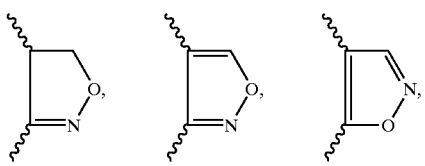

Here, extraordinary preference is given to the compounds VI, VIa, VIb and VIc where
$R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl; in particular $C_1$–$C_6$-alkylsulfonyl.

The tricyclic benzoic esters VIc can be obtained in different ways.

For example, benzoic esters of the formula VIII, which are prepared in a manner known per se (cf., for example, Chem. Pharm. Bull. 1985, 33 (8), 3336; Helv. Chim. Acta 1987, 70, 1326; J. Chem. Soc. Perkin Trans. 1972, 2019; J. Chem. Soc. Perkin Trans. 1991, 2763; Tetrahydron Asymmetry 1998, 9, 1137), can be cyclized to cyclic ketones of the formula IX (cf., for example, Chem. Ber. 1923, 56, 1819; J. Chem. Soc. Perkin I 1991, 2763; J. Med. Chem. 1988, 31, 230; Tetrahedron 1987, 43, 4549; Synlett 1991, 6, 443; Chem. Pharm. Bull. 1985, 33 (8), 3336). Analogously to known processes (cf., for example, J. Heterocyclic Chem. 1976, 13, 545; J. Heterocyclic Chem. 1972, 9, 1341; J. Org. Chem. 1978, 43, 3015; J. Chem. Soc. Perkin Trans. I 1978, 86; J. Org. Chem. 1986, 51, 2021), these can be converted into the tricyclic benzoic esters of the formula VIc.

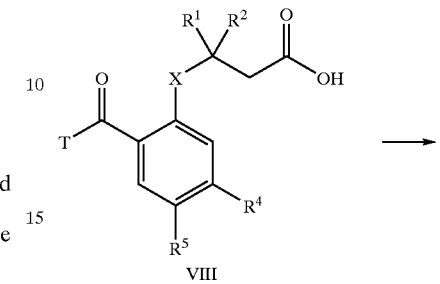

VIII

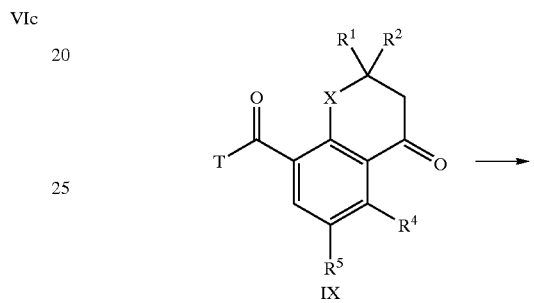

IX

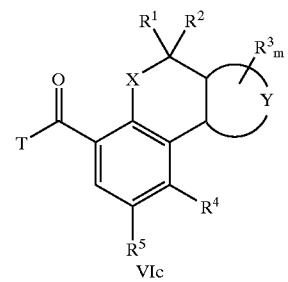

VIc

Furthermore, it may be suitable to acetylate the cyclic ketone of the formula IX in a manner known per se (X), for example using an anhydride or acid anhydride, if appropriate in the presence of catalytic amounts of a Lewis acid, such as boron trifluoride (cf., for example, Can. J. Chem. 1979, 57, 3292; J. Am. Chem. Soc. 1953, 75, 626), followed by reaction with a hydrazine (cf. A. R. Katritzky et al., Comprehensive Heterocyclic Chemistry, Vol. 5, p. 121, 277–280 (1984), Pergamon Press; J. Org. Chem. 1961, 26, 451; Org. Synth. 1949, 29, 54), where the resulting pyrazole radical can be modified further by customary processes.

Furthermore, the diketone X can be reacted with hydroxylamine or equivalents thereof (cf. A. R. Katritzky et al., Comprehensive Heterocyclic Chemistry, Vol. 6, p. 61–64, 118 (1984), Pergamon Press; Chem. Ber. 1967, 100, 3326). This gives corresponding isoxazole derivatives which can be modified further by customary processes.

It is also possible to react the diketone X with amidines (cf., for example, A. R. Katritzky et al., Comprehensive Heterocyclic Chemistry, Vol. 3, p. 112–114 (1924), Pergamon Press; J. Chem. Soc. C 1967, 1922; Org. Synth. 1963, IV, 182). If required, the resulting pyrimidine derivatives can be modified further by customary processes.

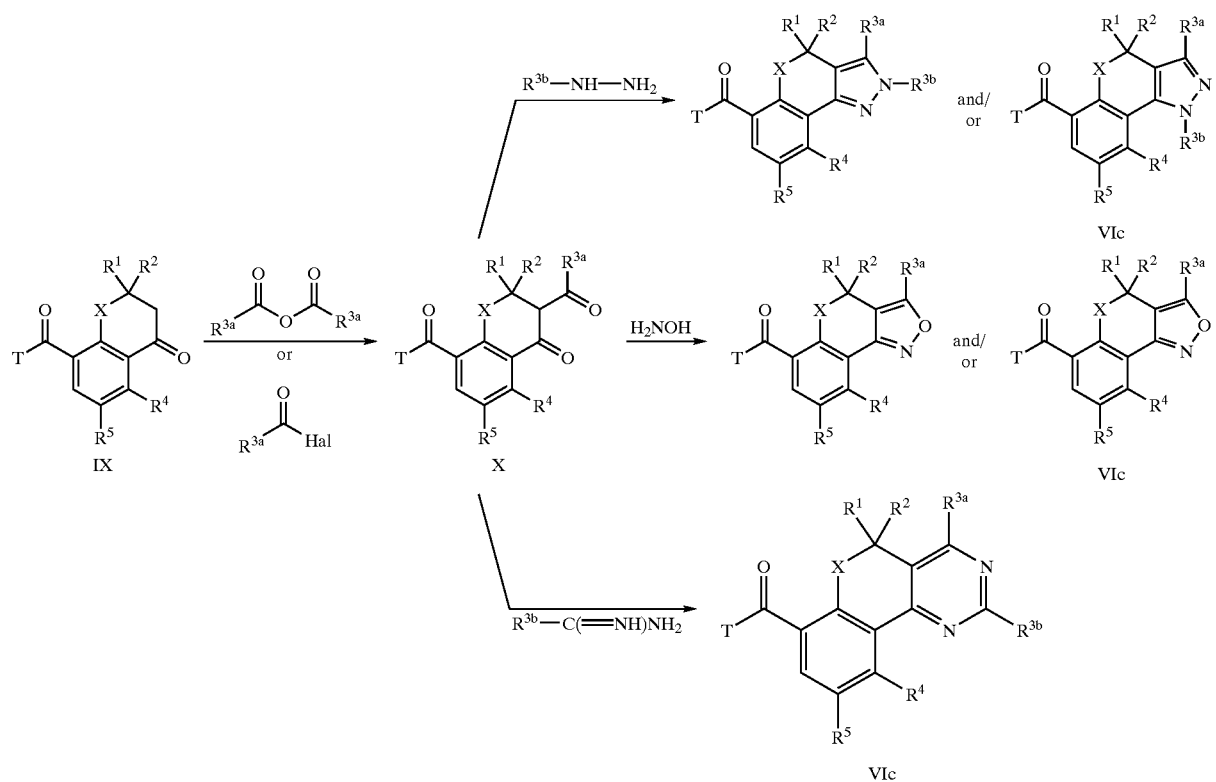

In the reactions mentioned above, it is also possible to employ, instead of the diketone X, equivalents thereof, such as enol ethers or enamines, which can be prepared analogously to known processes.

It may also be possible to react the cyclic ketone of the formula IX analogously to known processes with an aldehyde or ketone (XI) (cf., for example, Tetrahedron Lett. 1978, 2111; Tetrahedron Lett. 1981, 5251; Chem. Ber. 1960, 2294; J. Chem. Soc. Perkin Trans. 1, 1991, 1467; Tetrahedron Lett. 1992, 8091). The resulting unsaturated cyclic ketone of the formula XI can be reacted with a hydrazine in a manner known per se (cf., for example, A. R. Katritzky et al. Comprehensive Heterocyclic Chemistry, Vol. 2, 6 (1984), Pergamon Press; J. Heterocyclic Chem. 1969, 533; J. Heterocyclic Chem. 1968, 853), where the resulting pyrazoline can be modified further by customary processes.

It is furthermore possible to react the unsaturated cyclic ketone of the formula XI with hydroxylamine or equivalents thereof (Z. Chem. 1980, 20, 19). This gives corresponding isoxazoline derivatives, which can be modified further by customary processes.

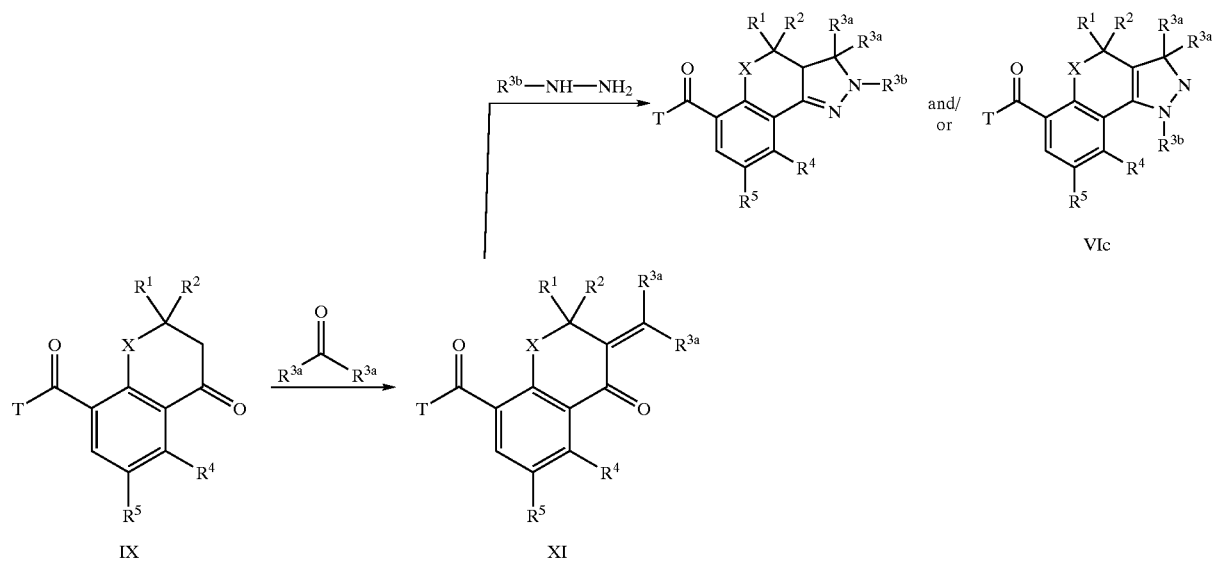

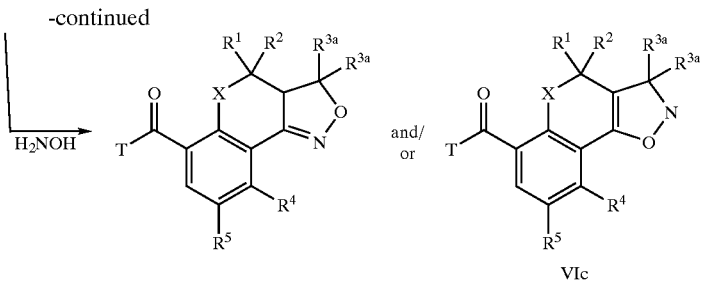

Furthermore, it is possible to convert aldehydes of the formula XII, which can be prepared in a manner known per se, analogously to processes known from the literature by reaction with a hydrazine or hydroxylamine (or equivalents of these) into corresponding hydrazones or oximes (cf., for example, Synth. Commun. 1990, 20, 1373; J. Org. Chem. 1980, 45, 3756). These in turn can be converted in a manner known per se into the corresponding 1,3-dipoles, which then react in a [3+2]-cyclo addition to give the compounds VIc (cf., for example, Synth. Commun. 1990, 20, 1373; EP-A 386 892; J. Org. Chem. 1980, 45, 3756; Tetrahedron Lett. 1981, 22, 1333.)

The resulting pyrazoles or pyrazolines and isoxazoles or isoxazolines can be modified further by customary processes.

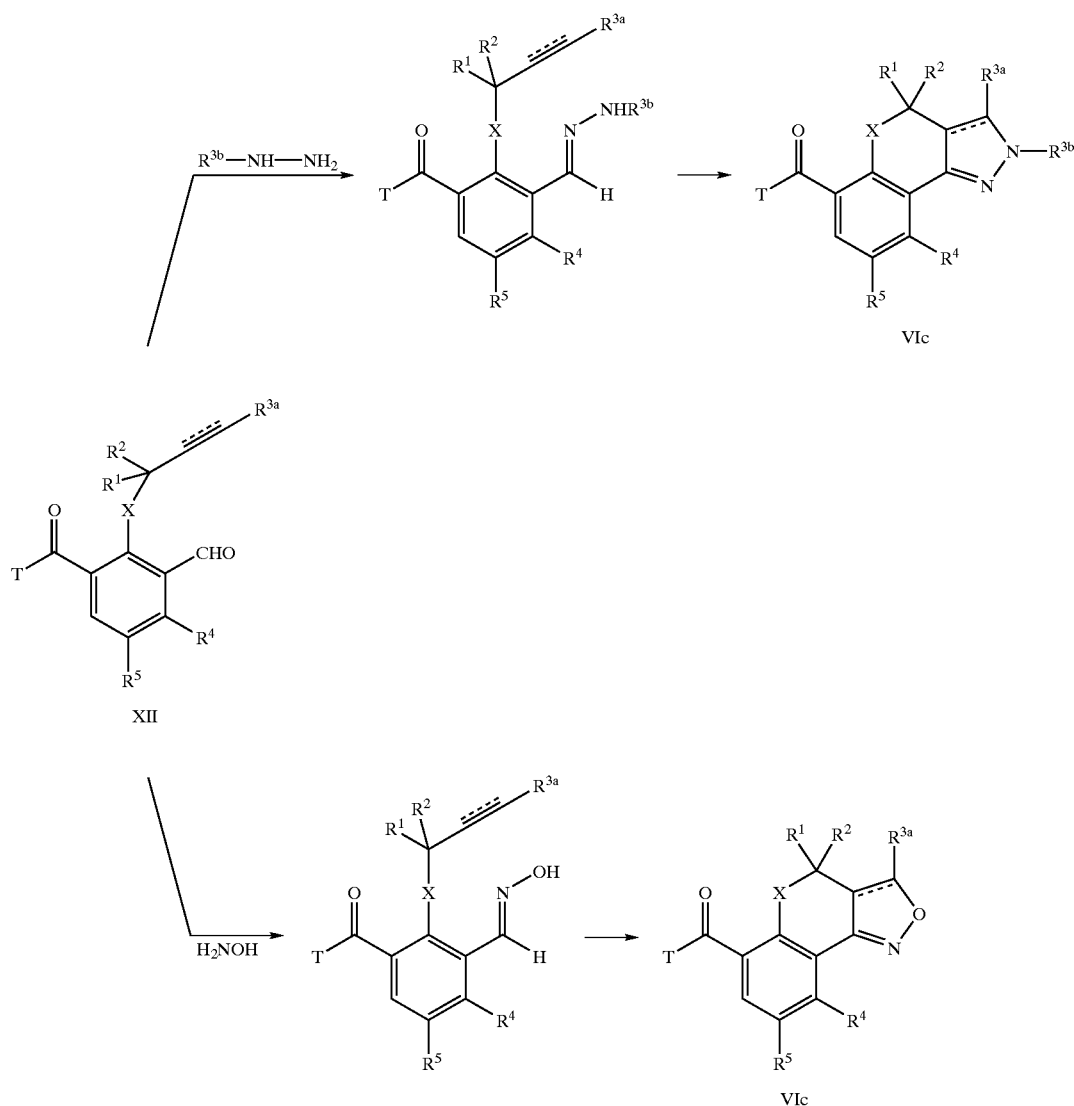

It is also possible to react the cyclic ketone of the formula IX with a dithiol or a "mixed alcohol" analogously to processes known from the literature (cf., for example, T. W. Greene et al., Protective Groups in Organic Synthesis, John Wiley & Sons, 133–140), and to subject it subsequently to a rearrangement in the presence of bromine or a suitable Lewis acid, such as, for example, tellurium tetrachloride (cf. Tetrahedron 1991, 47, 4187; Synthesis 1991, 223; J. Chem. Am. [sic] Soc. Chem. Commun. 1985, 1645).

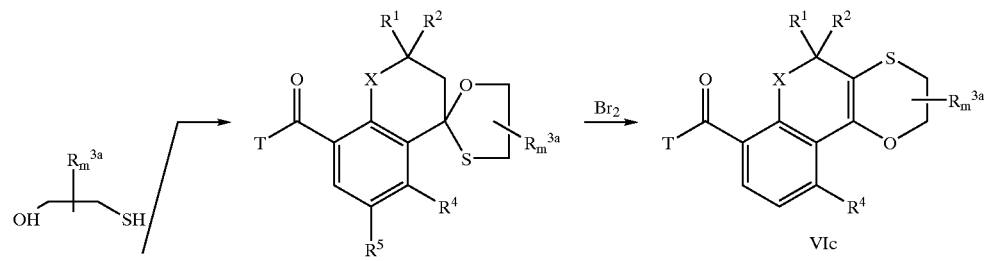

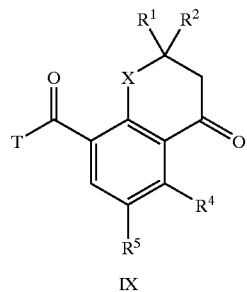

IX

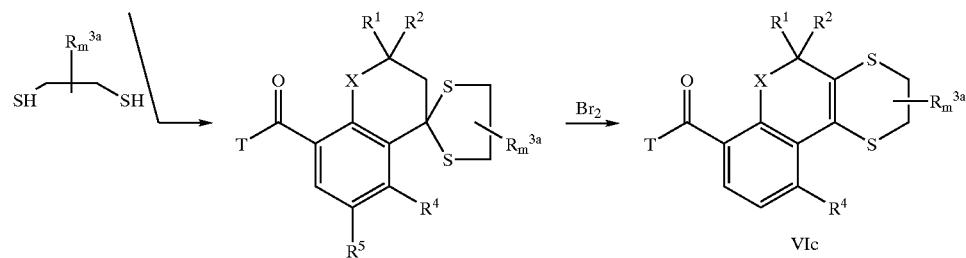

The resulting heterocycles can, if desired, be modified further by processes known per se.

The abovementioned substituents $R^{3a}$ are hydrogen, $C_1$–$C_6$-alkyl, $C_1$–$C_6$-haloalkyl, hydroxyl, $C_1$–$C_6$-alkoxy or $C_1$–$C_6$-haloalkoxy; furthermore, the abovementioned radicals $R^{3b}$ are hydrogen, $C_1$–$C_6$-alkyl or $C_1$–$C_6$-haloalkyl.

The tricyclic benzoic esters of the formula VIc or the tricyclic benzoic acids of the formula VIb can be obtained by reacting a tricyclic benzene derivative of the formula XIII with a $C_1$–$C_6$-alcohol or water in the presence of carbon monoxide, a catalyst and a base.

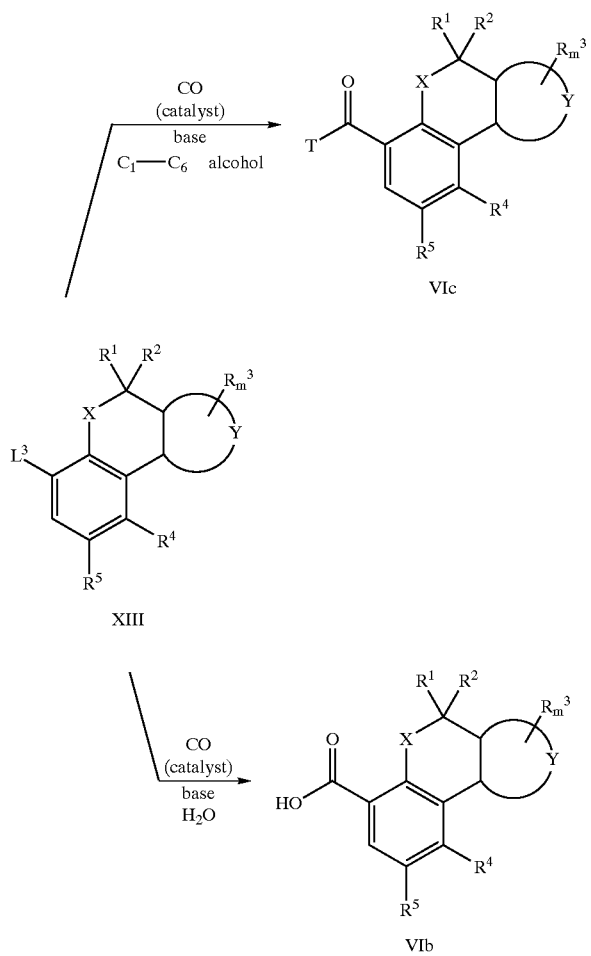

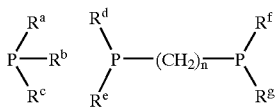

$L^3$ is a leaving group, such as halogen, for example chlorine, bromine or iodine, or sulfate, such as mesylate or triflate; preference is given to bromine or triflate.

Suitable catalysts are palladium ligand complexes in which the palladium is present in oxidation state 0, metallic palladium, if appropriate applied to a support, and preferably palladium(II) salts. The reaction with palladium(II) salts and metallic palladium is preferably carried out in the presence of complex ligands.

A suitable palladium(0) ligand complex is, for example, tetrakis(triphenylphosphane)palladium.

Metallic palladium is preferably applied to an inert carrier, such as, for example, activated carbon, silica, alumina, barium sulfate or calcium carbonate. The reaction is preferably carried out in the presence of complex ligands, such as, for example, triphenylphosphane.

Suitable palladium(II) salts are, for example, palladium acetate and palladium chloride. Preference is given to carrying out the reaction in the presence of complex ligands such as, for example, triphenylphosphane.

Suitable complex ligands for the palladium ligand complexes, or complex ligands in whose presence the reaction with metallic palladium or palladium(II) salts is preferably carried out are tertiary phosphanes whose structure is represented by the following formulae:

where n is a number from 1 to 4 and the radicals $R^a$ to $R^g$ are $C_1$–$C_6$-alkyl, aryl-$C_1$–$C_2$-alkyl or preferably aryl. Aryl is, for example, naphthyl and unsubstituted or substituted phenyl such as, for example, 2-tolyl and in particular unsubstituted phenyl.

The complex palladium salts can be prepared in a manner known per se starting from commercially available palladium salts, such as palladium chloride or palladium acetate, and the corresponding phosphanes, such as, for example, triphenylphosphane or 1,2-bis(diphenylphosphano)ethane. A large number of complexed palladium salts is also commercially available. Preferred palladium salts are [(R)-(+)-2,2'-bis(diphenylphosphano)-1,1'-binaphthyl]palladium(II) chloride, bis(triphenylphosphane)palladium(II) acetate and in particular bis(triphenylphosphane)palladium(II) chloride.

The palladium catalyst is generally employed in a concentration of from 0.05 to 5 mol %, and preferably of 1–3 mol %.

Suitable bases are tertiary amines, such as, for example, N-methylpiperidine, ethyldiisopropylamine, 1,8-bisdimethylaminonaphthalene and in particular triethylamine. Also suitable are alkali metal carbonates, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on the tricyclic benzene derivative of the formula IX.

Suitable solvents are nitrites, such as benzonitrile and acetonitrile, amides, such as dimethylformamide, dimethylacetamide, tetra-$C_1$–$C_4$-alkylureas or N-methylpyrrolidone, and preferably ethers, such as tetrahydrofuran, methyl tert-butyl ether. Particular preference is given to using, as solvents, ethers such as 1,4-dioxane and dimethoxyethane Furthermore, the tricyclic benzoic acids of the formula VIb can be obtained by converting a tricyclic benzene derivative of the formula XIII where $L^3$ is halogen, such as chlorine or bromine, in particular bromine, by reaction with, for example, n-butyllithium or magnesium into the metalated derivative, followed by quenching with carbon dioxide (cf., for example, J. Org. Chem. 1990, 55, 773; Angew. Chem. Int. Ed. 1969, 8, 68).

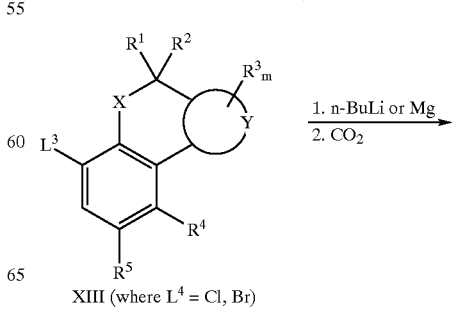

XIII (where $L^4$ = Cl, Br)

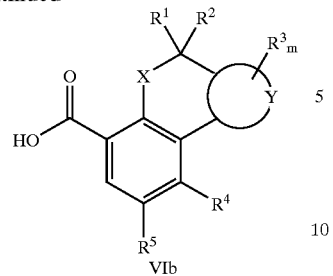

It is also possible to obtain the tricyclic benzoic acids VIb by hydrolyzing the corresponding nitriles, analogously to processes known from the literature. The nitriles for their part can be obtained by halogen/nitrile exchange or by Sandmeyer reaction from the corresponding anilines XIV.

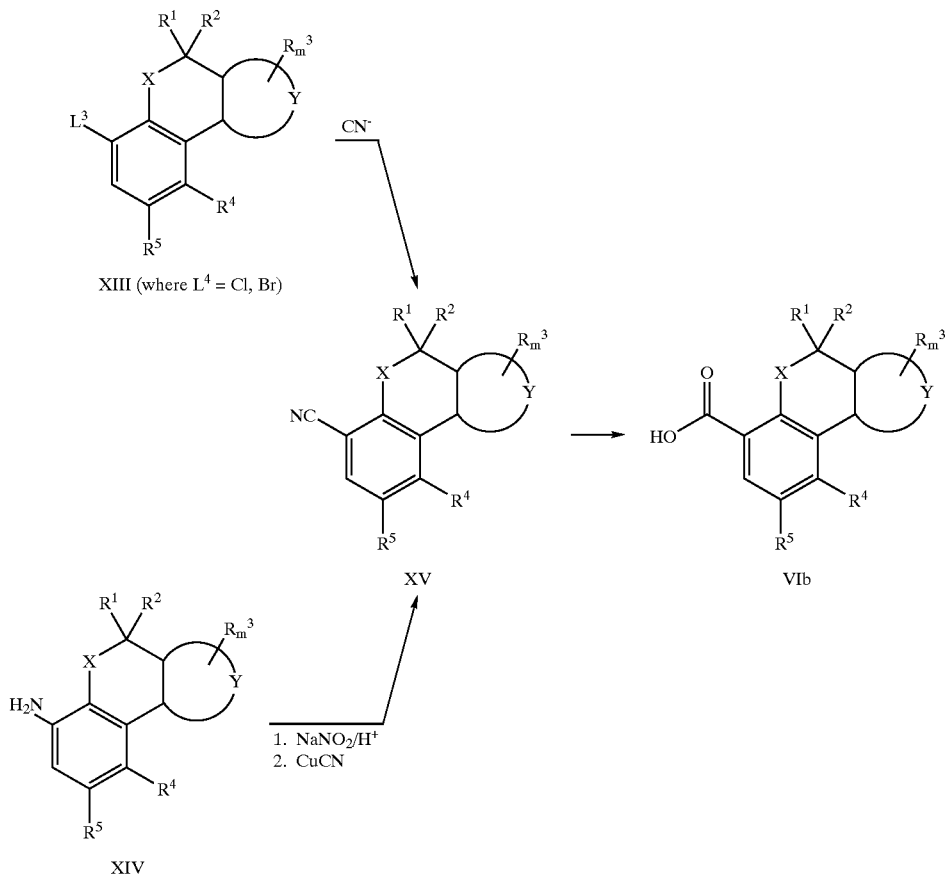

The compounds of the formula XIII, where:

X is oxygen, sulfur, S=O, S(=O)$_2$, CR$^6$R$^7$, NR$^8$ or a bond;

Y together with the two carbons to which it is attached forms a saturated, partially saturated or unsaturated 5- or 6-membered heterocycle which contains one to three identical or different heteroatoms selected from the following group: oxygen, sulfur or nitrogen;

R$^1$, R$^2$, R$^6$, R$^7$ are hydrogen, C$_1$–C$_6$-alkyl, C$_1$–C$_6$-haloalkyl, C$_1$–C$_6$-alkoxy or C$_1$–C$_6$-haloalkoxy;

R$^3$ is halogen, C$_1$–C$_6$-alkyl, C$_1$–C$_6$-haloalkyl, C$_1$–C$_6$-alkoxy or C$_1$–C$_6$-haloalkoxy;

R$^4$ is nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, N—(C$_1$–C$_6$-alkyl)aminosulfonyl, N,N-di(C$_1$–C$_6$-alkyl)aminosulfonyl, N—(C$_1$–C$_6$-alkylsulfonyl)amino, N—(C$_1$–C$_6$-haloalkylsulfonyl)amino, N—(C$_1$–C$_6$-alkyl)-N—(C$_1$–C$_6$-alkylsulfonyl)amino or N—(C$_1$–C$_6$-alkyl)-N—(C$_1$–C$_6$-haloalkylsulfonyl)amino;

R$^5$ is hydrogen, C$_1$–C$_6$-alkyl or halogen;

R$^8$ is hydrogen, C$_1$–C$_6$-alkyl, C$_1$–C$_6$-haloalkyl, C$_1$–C$_6$-alkylcarbonyl, formyl, C$_1$–C$_6$-alkoxycarbonyl, C$_1$–C$_6$-haloalkoxycarbonyl, C$_1$–C$_6$-alkylsulfonyl or C$_1$–C$_6$-haloalkylsulfonyl;

m is 0, 1 or 2;

L$^3$ is halogen, C$_1$–C$_6$-alkylsulfonyloxy, C$_1$–C$_6$-haloalkylsulfonyloxy or phenylsulfonyloxy, where the phenyl ring of the last-mentioned radical may be unsubstituted or partially or fully halogenated and/or may carry one to three of the following radicals: nitro, cyano, C$_1$–C$_6$-alkyl, C$_1$–C$_6$-haloalkyl, C$_1$–C$_4$-alkoxy or C$_1$–C$_4$-haloalkoxy;

are novel and also form part of the subject matter of the invention.

Preference is given to compounds of the formula XIII where L$^3$ is halogen, in particular bromine.

The particularly preferred embodiments of the compounds of the formula XIII with respect to the variables X, Y, R$^1$ to R$^5$ and m correspond to those of the tricyclic benzoylcyclohexanedione derivatives of the formula I.

Particular preference is given to the compounds of the formula XIII where
  Y together with the two carbons to which it is attached forms the following heterocycles:

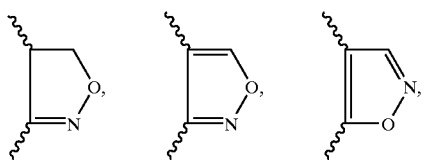

Here, extraordinary preference is given to the compounds XIII where
  $R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl; in particular $C_1$–$C_6$-alkylsulfonyl.

The compounds of the formula XIII can be obtained in different ways, the fused system, for example, can be constructed analogously to the processes described for the compounds of the formula VIc.

However, it is also possible to construct the fused system from a suitable parent compound (analogously to the processes described for compounds of the formula VIc) and to introduce $L^3$=halogen subsequently by customary halogenating reactions.

The anilines of the formula XIV and the nitriles of the formula XV

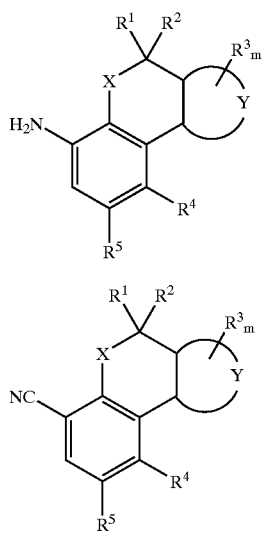

where:
  X is oxygen, sulfur, S=O, S(=O)$_2$, CR$^6$R$^7$, NR$^8$ or a bond;
  Y together with the two carbons to which it is attached forms a saturated, partially saturated or unsaturated 5- or 6-membered heterocycle which contains one to three identical or different heteroatoms selected from the following group: oxygen, sulfur or nitrogen;
  $R^1$,$R^2$,$R^6$,$R^7$ are hydrogen, $C_1$–$C_6$-alkyl, $C_1$–$C_6$-haloalkyl, $C_1$–$C_6$-alkoxy or $C_1$–$C_6$-haloalkoxy;
  $R^3$ is halogen, $C_1$–$C_6$-alkyl, $C_1$–$C_6$-haloalkyl, $C_1$–$C_6$-alkoxy or $C_1$–$C_6$-haloalkoxy;
  $R^4$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)aminosulfonyl, N,N-di($C_1$–$C_6$-alkyl)aminosulfonyl, N—($C_1$–$C_6$-alkylsulfonyl)amino, N—($C_1$–$C_6$-haloalkylsulfonyl)amino, N—($C_1$–$C_6$-alkyl)-N—($C_1$–$C_6$-alkylsulfonyl)amino or N—($C_1$–$C_6$-alkyl)-N—($C_1$–$C_6$-haloalkylsulfonyl)amino;
  $R^5$ is hydrogen, $C_1$–$C_6$-alkyl or halogen;
  R8 is hydrogen, $C_1$–$C_6$-alkyl, $C_1$–$C_6$-haloalkyl, $C_1$–$C_6$-alkylcarbonyl, formyl, $C_1$–$C_6$-alkoxycarbonyl, $C_1$–$C_6$-haloalkoxycarbonyl, $C_1$–$C_6$-alkylsulfonyl or $C_1$–$C_6$-haloalkylsulfonyl;
  m is 0, 1 or 2;
are also novel and form part of the subject matter of the invention.

The particularly preferred embodiments of the compounds of the formulae XIV and XV with respect to the variables X, Y, $R^1$ to $R^5$ and m correspond to those of the tricyclic benzoylcyclohexanedione derivatives of the formula I.

Particular preference is given to the compounds of the formula XV [sic] or XVI [sic] where
  Y together with the two carbons to which it is attached forms the following heterocycles:

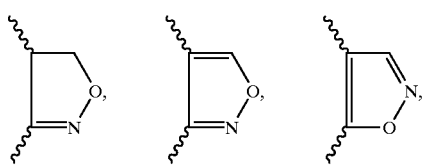

Here, extraordinary preference is given to the compounds XIV or XV where
  $R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl; in particular $C_1$–$C_6$-alkylsulfonyl.

The compounds of the formula XIV can be obtained in different ways; for example, the fused system can be constructed analogously to the processes described for the compounds of the formula VIc.

However, it is also possible to construct the fused system from a suitable parent compound (analogously to the processes described for the compounds of the formula VIc) and to introduce a nitro group subsequently by nitration para to $R^4$, analogously to processes known from the literature, and to convert this group in a manner known per se by reduction into the amino group.

If appropriate, it may be advantageous in the synthesis variants described above to introduce protective groups for certain functionalities if the functionalities are not compatible with the reaction conditions required.

The selection of the protective groups depends both on the reaction conditions and on the structure of the molecule. The protective groups, their introduction and their removal are generally known from the literature (cf., for example, T. W. Greene et al., "Protective Groups in Organic Synthesis", $2^{nd}$ edition, Wiley, New York, 1991), and they can be employed analogously to processes known from the literature.

Furthermore, it may be necessary to carry out a combination of the synthesis variants described above.

It is also possible to introduce further substituents or to modify the substituents present by electrophilic, nucleophilic, free-radical or organometallic reactions and by oxidation or reduction reactions

PREPARATION EXAMPLES

1. (5,5-Dimethyl-1,3-dioxocyclohex-2-yl)(6-methoxy-3a,4-dihydro-3H-chromeno[4,3-c]isoxazolin-9-yl)methanone (Compound 2.2)

Methyl 2-hydroxy-3-formyl-4-methoxy-benzoate

At from 0 to 5° C., a solution of 209.0 g (1.1 mol) of titanium tetrachloride in 150 ml of methylene chloride was added dropwise to a solution of 50.1 g (0.275 mol) of methyl 2-hydroxy-4-methoxybenzoate and 88 g (0.725 mol) of dichloromethoxymethane in 400 ml of methylene chloride, and the mixture was stirred at room temperature overnight. The mixture was subsequently added to ice-water with stirring and extracted with methylene chloride. The combined organic phases were washed with sodium bicarbonate solution, water and sodium chloride solution and dried, and the solvent was then removed. Chromatography over silica gel using cyclohexane/ethyl acetate=1:1 gave 24.5 g (42%) of methyl 2-hydroxy-3-formyl-4-methoxy benzoate in the form of a colorless solid of m.p.: 123–124° C.

$^1$H-NMR (CDCl$_3$, δ in ppm): 3.92 (s, 3H); 3.98 (s, 3H); 6.49 (d, 1H); 8.19 (d, 1H); 10.39 (s, 1H).

Methyl 2-allyloxy-3-formyl-4-methoxybenzoate

At room temperature, 23.2 g (0.192 mol) of allyl bromide were added dropwise to a mixture of 21.0 g (0.375 mol) of potassium hydroxide and 20.2 g (0.096 mol) of methyl 2-hydroxy-3-formyl-4-methoxybenzoate in 500 ml of dimethyl sulfoxide, and the mixture was stirred at room temperature for 4 hours. The mixture was subsequently added to 1.5 l of 3% strength aqueous hydrochloric acid with stirring and extracted with ethyl acetate. The combined organic phases were washed with water and dried, and the solvent was removed. Chromatography over silica gel using cyclohexane/ethyl acetate=1:2 gave 7.7 g (36% of methyl 2-allyloxy-3-formyl-4-methoxybenzoate in the form of a yellowish oil.

$^1$H-NMR (CDCl$_3$, δ in ppm): 3.86 (s, 3H); 3.93 (s, 3H); 4.58 (d, 2H); 5.32 (d, 1H); 5.39 (d, 1H); 6.15 (m, 1H); 6.79 (d, 1H); 8.04 (d, 1H); 10.41 (s, 1H).

6-Methoxy-9-methoxycarbonyl-3a,4-dihydro-3H-chromeno[4,3-c]isoxazolin

Step a)

At room temperature, 4.6 g (18.4 mol) of methyl 2-allyloxy-3-formyl-4-methoxybenzoate in 70 ml of methanol were added dropwise to a solution of 2.25 g (32.3 mmol) of hydroxylammonium chloride and 2.7 g of pyridine in 70 ml of water. The mixture was stirred at room temperature overnight, 150 ml of water were added, the mixture was extracted with methylene chloride, the combined organic phases were washed with 3% strength aqueous hydrochloric acid and dried and the solvent was removed. The resulting oxime had a melting point of 126–129° C.

Step b)

This oxime was reacted further without further purification by dissolving it in 40 ml of methylene chloride and adding 15.0 ml (25.0 mmol) of sodium hydrochloride [sic] solution (12.5% of active chlorine) dropwise. A spatula tip of sodium acetate was added and the mixture was stirred at room temperature for 12 hours. The organic phase was separated off, the aqueous phase was extracted with methylene chloride, the combined organic phases were washed with water and dried and the solvent was removed. Chromatography over silica gel using cyclohexane/ethyl acetate=1:1 gave 2.2 g (49%) of 6-methoxy-9-methoxycarbonyl-3a,4-dihydro-3H-chromeno[4,3-c]isoxazoline in the form of a colorless solid of m.p.: 199–203° C.

$^1$H-NMR (CDCl$_3$, δ in ppm): 3.84 (s, 3H); 3.98 (s, 3H); 3.8–4.0 (m, 2H); 4.16 (dt, 1H); 4.63 (t, 1H); 4.84 (dd, 1H); 6.61 (d, 1H); 7.93 (d, 1).

6-Methoxy-9-hydroxycarbonyl-3a,4-dihydro-3H-chromeno[4,3-c]isoxazoline

At room temperature, a solution of 0.8 g (20.0 mmol) of sodium hydroxide in 7 ml of water was added dropwise to a solution of 2.1 g (8.0 mmol) of 6-methoxy-9-methoxycarbonyl-3a,4-dihydro-3H-chromeno[4,3-c]isoxazoline in 40 ml of methanol, and the mixture was heated under reflux for 6 hours. After cooling, the solvent was removed and the residue was taken up in about 50 ml of water and washed with methylene chloride. The aqueous phase was subsequently acidified using 10% strength hydrochloric acid (pH=1–2), and the precipitate was filtered off with suction, washed with water and dried at 60° C. This gave 1.7 g (86%) of 6-methoxy-9-hydroxycarbonyl-3a,4-dihydro-3H-chromeno[4,3-c]isoxazoline in the form of colorless crystals.

$^1$H-NMR (CDCl$_3$, δ in ppm): 3.73 (dd, 1H); 3.89 (s, 3H); 3.84–3.95 (m, 1H); 4.11 (dd, 1H); 4.54 (dd, 1B); 4.79 (dd, 1H); 6.61 (d, 1H); 7.81 (d, 1H).

(5,5-Dimethyl-1,3-dioxocyclohex-2-yl)(6-methoxy-3a,4-dihydro-3H-chromeno[4,3-c]isoxazolin-9-yl)methanone (Compound 2.2)

Step a)

At room temperature, 0.26 g (2.2 mol) of thione [sic] chloride and a drop of dimethyl formamide were added to a solution of 0.50 g (2.0 mmol) of 6-methoxy-9-hydroxycarbonyl-3a,4-dihydro-3H-chromeno[4,3-c]isoxazoline in 30 ml of carbon tetrachloride, and the mixture was stirred at 40–50° C. for 3 hours. The solvent was subsequently removed under reduced pressure. This gave, in quantitative yield (0.54 g), 6-methoxy-9-chloroformyl-3a,4-dihydro-3H-chromeno[4,3-c]isoxazoline as a brownish oil.

0.54 g (2.0 mmol) of 6-methoxy-9-chloroformyl-3a,4-dihydro-3H-chromeno[4,3-c]isoxazoline was dissolved in 30 ml of acetonitrile and, at 0° C., added dropwise to a solution of 0.28 g (2.0 mmol) of 5,5-dimethylcyclohexan-1,3-dione and 0.6 g (6.0 mmol) of triethylamine in 20 ml of acetonitrile. After 12 hours of stirring at room temperature, the solvent was removed and the residue was taken up in methylene chloride and washed with water. The mixture was dried and the solvent was distilled off. The residue was taken up in 25 ml of acetonitrile and decomposed [sic] with 0.59 g (6.0 mmol) of trimethylsilyl cyanide, and the mixture was stirred at 40° C. for 5 hours. After filtration, the solvent was removed and the residue was chromatographed using cyclohexane/ethyl acetate. This gave 0.59 g (79%) of the compound 2.2 as colorless crystals of melting point 203–206° C.

$^1$H-NMR (CDCl$_3$, g [sic] in ppm): 1.09 (s, 6H); 2.31 (s, 1H); 2.62 (s, 1H); 3.7–4.1 (m, 6H); 4.52 (dd, 1H); 4.61 (dd, 1H); 6.62 (d, 1H); 7.43 (d, 1H); 17.0 (Cs, 1H).

2. (5-Bromo-8-methylsulfonyl-3a,4-diyhdro-3H-indeno[1,2-c]isoxazol

2-Allyl-6-chlorobenzaldehyde

Under an atmosphere of protective gas, a solution of 10.89 g (0.107 mol) of trimethylethylenediamine in 50 ml of anhydrous tetrahydrofuran was cooled to −10° C. and mixed dropwise with 66.6 ml of a 1.6 molar n-butyllithium solution in hexane (0.107 mol). After 10 minutes, 15 g (0.107 mol) of 6-chlorobenzaldehyde in 70 ml of tetrahydrofuran were added dropwise, and the mixture was admixed with a further 0.214 mol of n-butyllithium in hexane (146.8 ml) and stirred at 0° C. for 2.5 hours. The mixture was cooled to −20° C., 12.42 g (0.139 mol) of copper(I) cyanide were added, the mixture was stirred at −10° C. for 30 minutes and 28.42 g of allyl bromide in 100 ml of tetrahydrofuran were then added dropwise. Stirring was continued at 0° C. for 2.5 hours, and 230 ml of saturated ammonium chloride solution were then added dropwise. The resulting solid was separated off and the aqueous phase was extracted with diethyl ether. The combined organic phases were then washed with saturated ammonium chloride solution and dried, and the solvent was removed under reduced pressure. This gave 17.0 g of 2-alkyl-6-chlorobenzaldehyde [sic] (89%) in the form of a dark oil.

$^1$H-NMR (CDCl$_3$, δ in ppm): 3.73 (d, 2H); 5.05 (dd, 2H); 5.96 (m, 1H); 7.05–7.48 (m, 3H); 10.58 (s, 1H).

2-Allyl-6-chlorobenzaldehyde oxime 5.58 g of sodium bicarbonate were added to a solution of 4.62 g of hydroxylamine hydrochloride in 50 ml of water, and the mixture was cooled to 0° C. A solution of 9.7 g (44.32 mmol) of 2-allyl-6-chlorobenzaldehyde in 50 ml of methanol was added, and the mixture was stirred at room temperature overnight. The methanol was subsequently removed under reduced pressure and the residue was added with stirring to 300 ml of water. The aqueous phase was extracted with diethyl ether, the combined organic phases were washed with saturated ammonium chloride solution and dried and the solvent was removed. This gave 8.7 g (quantitative) of 2-allyl-6-chlorobenzaldehyde oxime in the form of a viscous oil.

$^1$H-NMR (CDCl$_3$, δ in ppm): 3.58 (d, 2H); 5.02 (2d, 2H); 5.95 (m, 1H); 7.08–7.36 (m, 3H); 8.49 (s, 1H).

8-Chloro-3a,4-dihydro-3H-indeno[1,2-c]isoxazol

At room temperature, 37.0 ml of a sodium hypochloride [sic] solution (12.5% of active chlorine) were added dropwise to a solution of 8.4 g (42.9 mmol) of 2-allyl-6-chlorobenzaldehyde oxime in 100 ml of methylene chloride, and a spatula tip of sodium acetate was added. The mixture was stirred at room temperature for 2 hours, the organic phase was separated off, the aqueous phase was extracted with methylene chloride and the combined organic phases were washed with saturated ammonium chloride solution and dried, and the solvent was removed. This gave 7.0 g (94%) of 8-chloro-3a,4-dihydro-3H-indeno[1,2-c]isoxazol in the form of a viscous oil.

$^1$H-NMR (CDCl$_3$, δ in ppm): 2.81 (dd, 1H); 3.24 (dd, 1H); 3.78–4.03 (s, 2H); 4.78 (t, 1H); 7.23–7.41 (m, 3H).

8-Methylthio-3a,4-dihydro-3H-indeno[1,2c]isoxazol

At room temperature, 3.6 g (52.0 mmol) of sodium thiomethoxide were added to a solution of 5.0 g (25.8 mmol) of 8-chloro-3a,4-dihydro-3H-indeno-[1,2-c]isoxazol in 60 ml of N-methylpyrrolidone, and the mixture was stirred overnight. The mixture was subsequently added with stirring to 800 ml of water, the aqueous phase was extracted with diethyl ether, the combined organic phases were washed with saturated ammonium chloride solution and dried and the solvent was removed. This gave 4.6 g (87%) of 8-methylthio-3a,4-dihydro-3H-indeno[1,2-c]isoxazol in the form of a dark-brown solid.

$^1$H-NMR (CDCl$_3$, δ in ppm): 2.54 (s, 3H); 2.78 (dd, 1H); 3.21 (dd, 1H); 3.72–3.93 (s, 2H); 4.64 (t, 1H); 7.09–7.38 (m, 3H).

5-Bromo-8-methylthio-3a,4-dihydro-3H-indeno[1,2-c]isoxazol 120 ml of sulfuric acid (98 percent strength) were cooled to 0° C., and 11.2 g (54.8 mmol) of 8-methylthio-3a,4-dihydro-3H-indeno[1,2-c]isoxazol were added a little at a time. 9.2 g (57.5 mmol) of bromine were then added dropwise, and the mixture was stirred at 0° C. for 2 hours. The resulting solution was poured into 2 l of a mixture of water and ice, the mixture was stirred for 1.5 hours and the precipitated solid was filtered off with suction and then washed and dried. This gave 11.4 g (73%) of 5-bromo-8-methylthio-3a,4-dihydro-3H-indeno[1,2-c]isoxazol of a brown solid of m.p. 127–135° C.

$^1$H-NMR (CDCl$_3$, δ in ppm): 2.53 (s, 3H); 2.71 (dd, 1H); 3.24 (dd, 1H); 3.81–4.02 (s, 2H); 4.71 (t, 1H); 7.01 (d, 1H); 7.47 (d, 1H).

5-Bromo-8-methylsulfonyl-3a,4-dihydro-3H-indeno[1,2-c]isoxazol

A solution of 11.2 g (39.4 mmol) of 5-bromo-8-methylthio-3a,4-dihydro-3H-indeno[1,2-c]isoxazol and 1.55 g of sodium tungstate in 250 ml of toluene and 50 ml of glacial acetic acid was heated to 70° C. and admixed dropwise with 10.73 g (39 percent strength, 86.8 mmol) of hydrogen peroxide. Stirring at 70° C. was continued for 3 hours, and a solid precipitated out. The mixture was allowed to cool to room temperature and stirred into 1 l of water, and the white solid was filtered off with suction. The organic phase of the filtrate was separated off and the aqueous phase was extracted with ethyl acetate. The combined organic phases were washed with water and dried and the solvent was removed. This gave a viscous brown oil which was stirred with hexane/ethyl acetate (4:1). The resulting precipitate was filtered off with suction and combined with the solid which had been obtained above. This gave 7.3 g (59%) of 5-bromo-8-methylsulfonyl-3a,4-dihydro-3H-indeno[1,2-c]isoxazol.

$^1$H-NMR (d$^6$-DMSO, δ in ppm): 2.93 (dd, 1H); 3.23 (dd, 1H); 3.41 (s, 3H); 3.94 (dd, 1H); 4.16 (m, 1H); 4.81 (t, 1H); 7.82 (d, 1H); 8.03 (d, 1H).

3. 2-Methyl-6-hydroxycarbonyl-9-chloro-[1]-thiochromano[4,3-c]pyrazol

Methyl 2-chlorosulfonyl-4-chlorobenzoate

At from 0 to 5° C., a solution of 60.9 g (0.88 mol) of sodium nitrite in 100 ml of water was added dropwise to a solution of 139 g (0.75 mol) of methyl 2-amino-4-chlorobenzoate in 400 ml of concentrated hydrochloric acid, and stirring at 0° C. was continued for 1 hour.

In a second apparatus, 3 g of copper(II) chloride, 3 g of benzyltriethylammonium chloride, 10 ml of water and 400 ml of 1,2-dichloroethane were combined and 64 g (1 mol) of sulfur dioxide were introduced.

The diazonium salt was then added at 10 to 15° C. as described above [sic], and the mixture was slowly heated to 50° C. A further 54 g (0.84 mol) of sulfur dioxide were then introduced, and stirring at 50° C. was continued for 30 minutes. After cooling, 7.4 g (0.1 mol) of gaseous chlorine were introduced at room temperature, stirring was continued for 15 minutes and the phases which formed were then separated. The organic phase was dried and the solvent was removed. This gave 207 g of methyl 2-chlorosulfonyl-4-chlorobenzoate.

$^1$-NMR (CDCl$_3$, δ in ppm): 4.00 (s, 3H); 7.75 (m, 2H); 8.18 (m, 1H)

Methyl 2-mercapto-4-chlorobenzoate

Over a period of 1.5 hours, 243.5 g (3.7 mol) of zinc powder were added a little at a time to a suspension of 205 g (0.75 mol) of methyl 2-chlorosulfonyl-4-chlorobenzoate in 1 l of concentrated hydrochloric acid and 375 g of ice. Stirring was continued for 3 hours, and the mixture was then slowly heated to 70° C. After 2 hours at this temperature, the mixture was cooled. The reaction mixture was allowed to stand at room temperature for 12 hours and then extracted with ethyl acetate, the combined organic phases [lacuna] and the solvent was removed. This gave 125.4 g (83%) of methyl 2-mercapto-4-chlorobenzoate.

$^1$H-NMR (CDCl$_3$, δ in ppm): 3.95 (s, 3H); 4.88 (s, 1H); 7.10 (m, 1H); 7.30 (m, 1H); 7.96 (d, 1H).

Methyl 2-(2-hydroxycarbonyleth-1-yl)thio-4-chlorobenzoate 179.5 g (1.3 mol) of potassium carbonate and, a little at a time, 94.5 g (0.62 mol) of 3-bromopropionic acid were added to a solution of 125.4 g (0.62 mol) of methyl 2-mercapto-4-chlorobenzoate in 1.5 l of acetone, and the reaction mixture was stirred at room temperature for 12 hours. The solvent was distilled off, the residue was taken up in water and the mixture was extracted with diethyl ether. The aqueous phase was then made acidic using concentrated hydrochloric acid and the precipitate was filtered off with suction and dried. This gave 160 g (88%) of methyl 2-(2-hydroxycarbonyeth-1-yl)thio-4-chlorobenzoate M.p.: 133 to 136° C.

Methyl 5-chloro-4-oxothiochromane-8-carboxylate

At 70° C., 50 g (0.18 mol) of methyl 2-(2-hydroxycarbonyleth-1-yl)thio-4-chlorobenzoate were against [sic] to 500 g of polyphosphoric acid, and the mixture was stirred for 30 minutes. The reaction mixture was subsequently added to water with stirring, and the resulting precipitate was filtered off with suction and dried. This gave 41.1 g (88%) of methyl 5-chloro-4-oxothiochromane-8-carboxylate.

$^1$H-NMR (CDCl$_3$, δ in ppm): 3.08 (m, 4H); 3.96 (s, 3H); 7.14 (d, 1H); 7.95 (d, 1H).

Methyl 5-chloro-3-(N,N-dimethylaminomethylidene)-4-oxothiochromane-8-carboxylate 30 g (0.078 mol) of methyl 5-chloro-4-oxothiochromane-8-carboxylate in 300 ml of N,N-dimethylformamide dimethyl acetal were heated under reflux for 6 hours. Volatile components were then distilled off, the residue was taken up in methylene chloride and the organic phase was washed with water. Drying and removal of the solvent gave 35.3 g (97%) of methyl 5-chloro-3-(N,N-dimethylaminomethylidene)-4-oxothiochromane-8-carboxylate.

$^1$H-NMR (CDCl$_3$, δ in ppm): 3.18 (s, 6H); 3.80 (s, 2H); 3.95 (s, 3H); 7.24 (d, 1H); 7.64 (s, 1H); 7.82 (d, 1H).

2-Methyl-6-methoxycarbonyl-9-chloro-[1]-thiochromano[4,3-c]pyrazol 1.3 g (29.2 mol) of methylhydrazine were added dropwise to a solution of 7.0 g (22.5 mmol) of methyl 5-chloro-3-(N,N-dimethylaminomethylidene)-4-oxothiochromane-8-carboxylate in 700 ml of ethanol, and the mixture was heated under reflux for 2 hours. The solvent was removed and the residue was chromatographed over silica gel using the mobile phase ethyl acetate/cyclohexane (2:3). This gave 4.0 g (60%) of 2-methyl-6-methoxycarbonyl-9-chloro-[1]-thiochromano[4,3-c]pyrazol.

$^1$H-NMR (CDCl$_3$, δ in ppm): 3.76 (s, 2H); 3.95 (s, 3H); 4.00 (s, 3H); 7.24 (s, 1H); 7.36 (d, 1H); 7.70 (d, 1H).

2-Methyl-6-hydroxycarbonyl-9-chloro-[1]-thiochromano[4,3-c]pyrazol 4.0 g (13.6 mmol) of 2-methyl-6-methoxycarbonyl-9-chloro-[1]-thiochromano[4,3-c]pyrazol in 100 ml of methanol/water (1:1) were refluxed for one hour with 0.8 g (20 mmol) of sodium hydroxide. The organic solvent was removed under reduced pressure and the residue was extracted with ethyl acetate. The aqueous phase was acidified using concentrated hydrochloric acid and the resulting precipitate was filtered off with suction and dried. This gave 3.5 g (92%) of 2-methyl-6-hydroxycarbonyl-9-chloro-[1]-thiochromano[4,3-c]pyrazol $^1$H-NMR (CDCl$_3$, δ in ppm): 3.80 (s, 2H); 3.96 (s, 3H); 7.40 (d, 1H); 7.65 (m, 2H).

In addition to the above compounds, tables 2 to 4 list further tricyclic benzoylcyclohexanedione derivatives of the formula I which were prepared or are preparable in an analogous manner:

TABLE 2

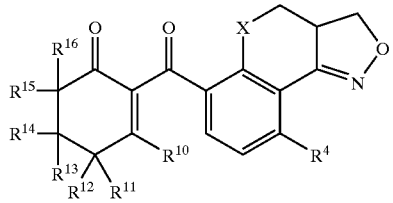

Ia where m = O [sic], $R^1$, $R^2$, $R^5$ = H, Y together with the two carbons to which it is attached forms the following isoxazoline:

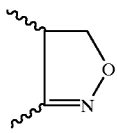

| No. | X | $R^4$ | $R^{10}$ | $R^{11}$ | $R^{12}$ | $R^{13}$ | $R^{14}$ | $R^{15}$ | $R^{16}$ | physical data (m.p. [° C.]; $^1$H-NMR [ppm]) |
|---|---|---|---|---|---|---|---|---|---|---|
| 2.1 | O | OCH$_3$ | OH | CH$_3$ | CH$_3$ | | =O | CH$_3$ | CH$_3$ | 7.42(d, 1H); 6.86 (d, 1H); 4.62(s, 1H); 4.51(dd, 1H); 3.8–4.1 (m, 6H); 1.45(s, 12H) |
| 2.2 | O | OCH$_3$ | OH | H | H | CH$_3$ | CH$_3$ | H | H | 206 |

TABLE 3

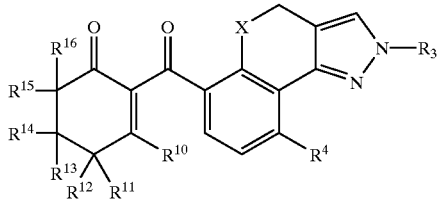

Ia where $R_1$, $R^2$, $R^5$ = H, Y together with the two carbons to which it is attached forms the following substituted pyrazol:

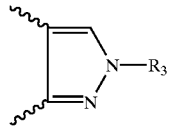

| No. | X | $R^3$ | $R^4$ | $R^{10}$ | $R^{11}$ | $R^{12}$ | $R^{13}$ | $R^{14}$ | $R^{15}$ | $R^{16}$ | physical data (m.p. [° C.]) |
|---|---|---|---|---|---|---|---|---|---|---|---|
| 3.1 | S | H | Cl | OH | H | H | CH$_3$ | CH$_3$ | H | H | 124 |
| 3.2 | S | H | Cl | OH | H | H | H | H | H | H | 127 |
| 3.3 | S | CH$_3$ | Cl | OH | H | H | H | H | H | H | 112 |
| 3.4 | S | CH$_3$ | Cl | OH | H | H | CH$_3$ | CH$_3$ | H | H | 101 |
| 3.5 | S | CH$_3$ | Cl | OH | CH$_3$ | CH$_3$ | =O | CH$_3$ | CH$_3$ |  | 95 |
| 3.6 | SO$_2$ | CH$_3$ | Cl | OH | H | H | H | H | H | H | 236 (decomp.) |
| 3.7 | S | CH$_3$ | —S—CH$_3$ | OH | H | H | H | H | H | H | 119 (decomp.) |
| 3.8 | S | CH$_3$ | —S—CH$_3$ | OH | CH$_3$ | CH$_3$ | =O | CH$_3$ | CH$_3$ |  | 212–214 |
| 3.9 | SO$_2$ | CH$_3$ | —SO$_2$—CH$_3$ | OH | H | H | H | H | H | H | 277 (decomp.) |
| 3.10 | SO$_2$ | CH$_2$ | —SO$_2$—CH$_3$ | OH | H | H | CH$_3$ | CH$_3$ | H | H | 251 (decomp.) |
| 3.11 | SO$_2$ | CH$_2$ | —SO$_2$—CH$_3$ | OH | CH$_3$ | CH$_3$ | =O | CH$_3$ | CH$_3$ |  | 176 (decomp.) |

TABLE 4

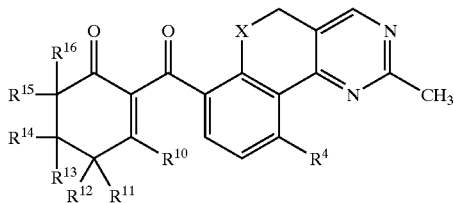

Ia where $R^1$, $R^2$, $R^5$ = H, Y together with the two carbons to which it is attached forms the following methyl-substituted pyrimidine:

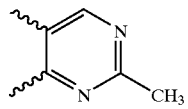

| No. | X | $R^4$ | $R^{10}$ | $R^{11}$ | $R^{12}$ | $R^{13}$ | $R^{14}$ | $R^{15}$ | $R^{16}$ | physical data (m.p. [° C.]) |
|---|---|---|---|---|---|---|---|---|---|---|
| 4.1 | S | Cl | OH | $CH_3$ | $CH_3$ | | =O | $CH_3$ | $CH_3$ | 95 |
| 4.2 | S | Cl | OH | H | H | $CH_3$ | $CH_3$ | H | H | 100 |
| 4.3 | S | Cl | OH | H | H | H | H | H | H | 109 |

The compounds of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus cormnunis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

In addition, the compounds I may also be used in crops which tolerate the action of herbicides owing to breeding, including genetic engineering methods.

The compounds of the formula I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee the finest possible distribution of the active ingredients according to the invention.

The herbicidal compositions comprise a herbicidally active amount of at least one compound of the formula I or an agriculturally useful salt of I and auxiliaries conventionally used in the formulation of crop protection agents.

Suitable inert auxiliaries are essentially:

mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes or their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the tricyclic benzoyl-cyclohexanedione derivatives of the formula I, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaph-thalenesulfonic acids, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ether, condensates of sulfonated naphthalene and its derivatives with formaldehyde, condensates of naphthalene, or of the naphthalenesulfonic acids with phenol and formaldehyde,. polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds of the formula I in the ready-to-use preparations can be varied within wide ranges. In general, the formulations comprise approximately from 0.001 to 98% by weight, preferably 0.01 to 95% by weight of at least one active compound. The active compounds are employed in a purity of from 90% to 100%, preferably 95% to 100% (according to NMR spectrum).

The formulation examples which follow illustrate the preparation of such compounds:

I. 20 parts by weight of the compound No. 3.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 3.2 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 3.4 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the compound No. 3.5 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the compound No. 4.1 are mixed with 97 parts by weight of finely divided kaolin. This gives a dust which comprises 3% by weight of active compound.

VI. 20 parts by weight of the active compound No. 4.2 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 3.3 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 4.2 is dissolved in a mixture composed of 80 parts by weight of cyclohexanone and 20 parts by weight of Wettol® EM 31 (nonionic emulsifier based on ethoxylated castor oil). This gives a stable emulsion concentrate.

The active compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active ingredients reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the tricyclic benzoylcyclohexanedione derivatives of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryloxy-/ hetaryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the tricyclic benzoylcyclohexanedione derivatives of the formula I was demonstrated by the following greenhouse experiments:

The culture containers used were plastic flowerpots containing loamy soil with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, unless this has been adversely affected by the active ingredients.

For the post-emergence treatment, the test plants were first grown to a plant height of 3 to 15 cm, depending on the plant habit, and only then treated with the active compounds which had been suspended or emulsified in water. The test plants for this purpose were either sown directly and grown in the same containers, or they were first grown separately as seedlings and transplanted into the test containers a few days prior to treatment. The rate of application for the post-emergence treatment was 0.5, 0.25 or 0.125 kg/ha of a.s.

Depending on the species, the plants were kept at 10 to 25° C. or 20 to 35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific Name | Common Name |
| --- | --- |
| Abutilon theophrasti | velvet leaf |
| Chenopodium album | lambsquarters (goosefoot) |
| Echinochloa crus-galli | barnyard grass |
| Ipomoea ssp. | morning glory |
| Solanum nigrum | black nightshade |
| Sinapis alba | white mustard |
| Setaria viridis | green foxtail |

At application rates of 0.25 or 0.125 kg/ha, the compound 2.1 exhibits very good post-emergence activity against the abovementioned undesirable plants *Chenopodium album, Echinochloa crus-galli,* Ipomoea ssp., *Setaria viridis* and *Solanum nigrum.* Furthermore, the compound 4.2, at application rates of 0.5 or 0.25 kg/ha applied by the post-emergence method, effects very efficient control of the harmful plants *Abutilon theophrasti, Echinochloa crus-galli, Sinapis alba* and *Solanum nigrum.*

We claim:
1. A tricyclic benzoylcyclohexanedione derivative of the formula I

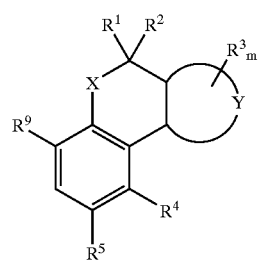

where:

X is oxygen, sulfur, S=O, or S(=O)$_2$;

Y together with the two carbon atoms to which it is attached forms a saturated, partially saturated or unsaturated 5-membered heterocycle which contains one to three identical or different heteroatoms selected from the following group: oxygen, sulfur or nitrogen;

$R^1$, $R^2$ are hydrogen, $C_1$–$C_6$-alkyl, $C_1$–$C_6$-haloalkyl, $C_1$–$C_6$-alkoxy or $C_1$–$C_6$-haloalkoxy;

$R^3$ is halogen, $C_1$–$C_6$-alkyl, $C_1$–$C_6$-haloalkyl, $C_1$–$C_6$-alkoxy or $C_1$–$C_6$-haloalkoxy;

$R^4$ is hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)-aminosulfonyl, N,N-di-($C_1$–$C_6$-alkyl)-aminosulfonyl, N—($C_1$–$C_6$-alkylsulfonyl)-amino, N—($C_1$–$C_6$-haloalkylsulfonyl)-amino, N—($C_1$–$C_6$-alkyl)-N—($C_1$–$C_6$-alkylsulfonyl)-amino or N—($C_1$–$C_6$-alkyl)-N—($C_1$–$C_6$-haloalkylsulfonyl)-amino;

$R^5$ is hydrogen, $C_1$–$C_6$-alkyl or halogen;

m is 0, 1 or 2;

$R^9$ is a radical IIa or IIb

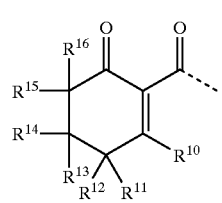

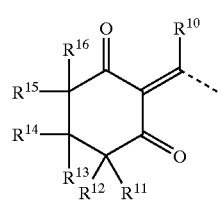

where:

$R^{10}$ is hydroxyl, mercapto, halogen, $OR^{17}$, $SR^{17}$, $SOR^{18}$, $SO_2R^{18}$, $OSO_2R^{18}$, $NR^{19}R^{20}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$, $R^{15}$ are hydrogen, $C_1$–$C_4$-alkyl or $C_1$–$C_4$-alkoxycarbonyl;

$R^{12}$, $R^{14}$, $R^{16}$ are hydrogen or $C_1$–$C_4$-alkyl;

$R^{13}$ is hydrogen, halogen, hydroxyl, $C_1$–$C_6$-alkyl, $C_1$–$C_6$-haloalkyl, di-($C_1$–$C_6$-alkoxy)methyl, ($C_1$–$C_6$-alkoxy)-($C_1$–$C_6$-alkylthio)methyl, di-($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_3$–$C_6$-alkoxycarbonyl, $C_1$–$C_6$-haloalkoxycarbonyl;

is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last-mentioned radicals may be substituted by one to three $C_1$–$C_4$-alkyl radicals; or $R^{12}$ and $R^{13}$ or $R^{13}$ and $R^{16}$ together form a π-bond or a $C_1$–$C_5$-alkyl chain which may carry one to three radicals from the following group: halogen, cyano, $C_1$–$C_4$-alkyl, $C_1$–$C_4$-haloalkyl or $C_1$–$C_4$-alkoxycarbonyl; or $R^{12}$ and $R^{16}$ together form a $C_1$–$C_4$-alkyl chain which may carry one to three radicals from the following group: halogen, cyano, $C_3$–$C_4$-alkyl, $C_1$–$C_4$-haloalkyl or $C_1$–$C_4$-alkoxycarbonyl;

$R^{13}$ and $R^{14}$ together form a —O—$(CH_2)_p$—O—, —O—$(CH_2)_p$—S—, —S—$(CH_2)_p$—S—, —O—$(CH_2)_q$— or —S—$(CH_2)_q$— chain which may be substituted by one to three radicals from the following group: halogen, cyano, $C_1$–$C_4$-alkyl, $C_1$–$C_4$-haloalkyl or $C_1$–$C_4$-alkoxycarbonyl; or $R^{13}$ and $R^{14}$ together with the carbon to which they are attached form a carbonyl group;

$R^{17}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N—($C_3$–$C_6$-alkenyl)-N—($C_1$–$C_6$-alkyl)-aminocarbonyl, N—($C_3$–$C_6$-alkynyl)-N—($C_1$–$C_6$-alkyl)-aminocarbonyl, N—($C_1$–$C_6$-alkoxy)-N—($C_1$–$C_6$-alkyl)-aminocarbonyl, N—($C_3$–$C_6$-alkenyl)-N—($C_1$–$C_6$-alkoxy)-aminocarbonyl, N—($C_3$–$C_6$-alkynyl)-N—($C_1$–$C_6$-alkoxy)-aminocarbonyl, di-($C_1$–$C_6$-alkyl)-aminothiocarbonyl, $C_1$–$C_6$-alkoxyimino-$C_1$–$C_6$-alkyl, where the alkyl, cycloalkyl or alkoxy radicals mentioned may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenylaminocarbonyl, N—($C_1$–$C_6$-alkyl)-N-phenylaminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylaminocarbonyl, N—($C_1$–$C_6$-alkyl)-N-heterocyclylaminocarbonyl or heterocyclyl-$C_1$–$C_6$-alkenylcarbonyl, where the phenyl or the heterocyclyl radical of the 18 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$ is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one to three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_4$-alkyl, heterocyclyl or heterocyclyl-$C_1$–$C_4$-alkyl, where the phenyl or the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{19}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-($C_1$–$C_6$-alkyl)amino or $C_1$–$C_6$-alkylcarbonylamino, where the alkyl, cycloalkyl or alkoxy radicals mentioned may be partially or fully halogenated and/or may carry one to three of the following radicals: cyano, $C_1C_4$-alkoxycarbonyl, $C_1$–$C_4$-alkylaminocarbonyl, di-($C_1$–$C_4$-alkyl)aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is hydrogen, $C_1$–$C_6$-alkyl, $C_3$–$C_6$-alkenyl or $C_3$–$C_6$-alkynyl;

p is 2, 3 or 4;

q is 1, 2, 3, 4 or 5;

and their agriculturally useful salts.

2. A process for preparing compounds of the formula I where $R^{10}$=halogen as claimed in claim 1, which comprises reacting a tricyclic benzoylcyclohexanedione derivative of the formula Iα (=I where $R^{10}$=hydroxyl),

Iα

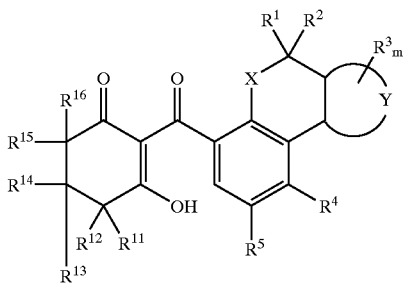

where the variables $R^1$ to $R^5$, $R^{11}$ to $R^{16}$, X, Y and m are as defined in claim 1 with a halogenating agent.

3. A process for preparing compounds of the formula I where $R^{10}=OR^{17}$, as claimed in claim 1, which comprises reacting a tricyclic benzoylcyclohexanedione derivative of the formula Iα, (=I where $R^{10}$=hydroxyl),

Iα

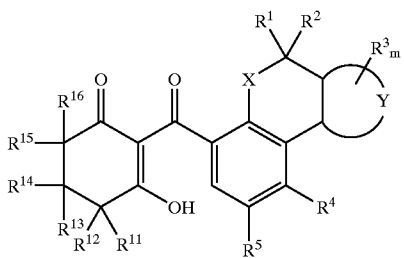

where the variables $R^1$ to $R^5$, $R^{11}$ to $R^{16}$, X, Y and m are as defined in claim 1 with a compound of the formula IIIα or IIIβ

| $L^1$-$R^{17}$ | $L^1$-$SO_2R^{18}$ |
|---|---|
| IIIα | IIIβ | where the variables $R^{17}$ and $R^{18}$ are as defined in claim 1 and $L^1$ is a nucleophilically replaceable leaving group.

4. A process for preparing compounds of the formula I where $R^{10}=R^{17}$, $SR^{17}$, $OSO_2R^{18}$, $NR^{19}R^{20}$ or N-bonded heterocyclyl as claimed in claim 1, which comprises reacting a compound of the formula Iβ (=I where $R^{10}$=halogen),

Iβ

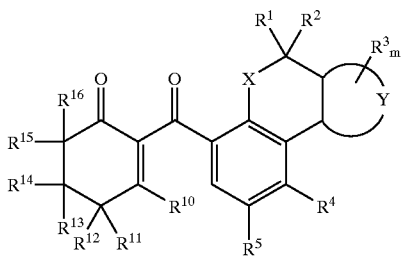

-continued

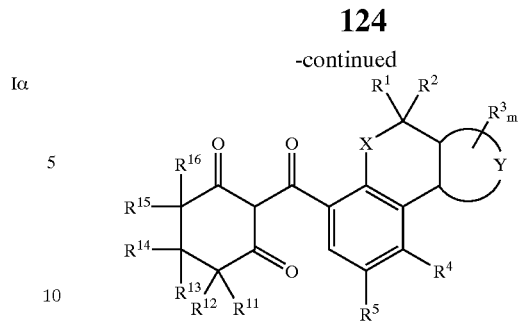

where the variables $R^1$ to $R^5$, $R^{11}$ to $R^{16}$, X, Y and m are as defined in claim 1 with a compound of the formula IVα, IVβ, IVγ, IVδ or IVβ [sic]

| HOR$^{17}$ | HSR$^{17}$ | HOSO$_2$R$^{18}$ | HNR$^{19}$R$^{20}$ | H(N-bonded heterocyclyl) |
|---|---|---|---|---|
| IVα | IVβ | IVγ | IVδ | IVε | where the variables $R^{17}$ to $R^{20}$ are as defined in claim 1, if appropriate in the presence of an base.

5. A process as preparing compounds of the formula I where $R^{10}=SOR^{18}$, $SO_2R^{18}$ as claimed in claim 1, which comprises reacting a compound of the formula Iγ (=I were $R^{10}=SR^{18}$),

Iγ

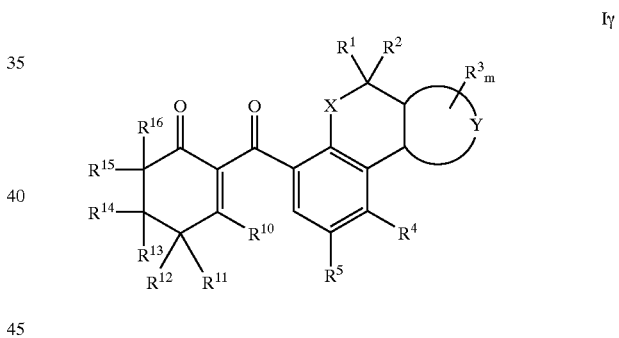

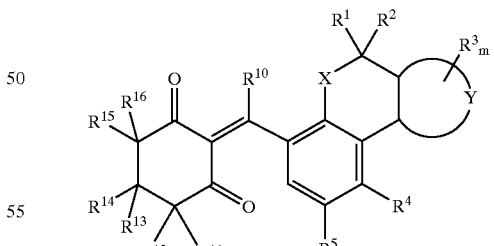

where the variables R to $R^5$, $R^{11}$ to $R^{16}$ and $R^{18}$, X, Y and m are defined as claim 1 with an oxidizing agent.

6. A process for preparing tricyclic benzoylcyclohexanedione derivatives of the formula Iα (=I where $R^{10}$= hydroxyl) as claimed in claim 1, which comprises acylating a cyclohexanedione of the formula V in which the variables $R^{11}$ to $R^{16}$ are as defined in claim 1,

V

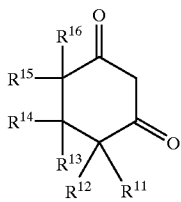

with an activated tricyclic benzoic acid of the formula VIα or with a tricyclic benzoic acid VIβ,

VIα

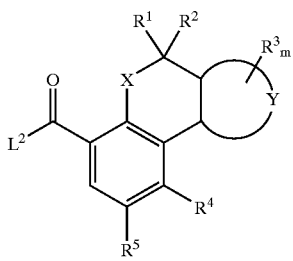

VIβ

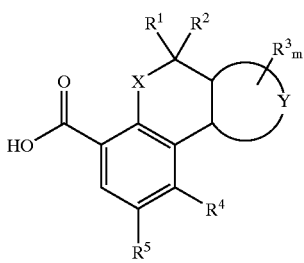

where the variables $R^1$ to $R^5$, X, Y and m are as defined in claim 1 and $L^2$ is a nucleophilically replaceable leaving group and rearranging the acylation product, if appropriate in the presence of a catalyst.

7. A composition, comprising a herbicidally effective amount of at least one tricyclic benzoylcyclohexanedione derivative of the formula I or an agriculturally useful salt of I as claimed in claim 1 and auxiliaries which are customarily used for formulating the crop protection agents.

8. A process for preparing compositions as claimed in claim 7, which comprises mixing a herbicidally effective amount of at least one tricyclic benzoylcyclohexanedione derivative of the formula I or an agriculturally useful salt of I and auxiliaries which are customarily used for formulating crop protection agents.

9. A method for controlling undesirable vegetation, which comprises allowing a herbicidally effective amount of at least one tricyclic benzoylcyclohexanedione derivative of the formula I or an agriculturally useful salt of I as claimed in claim 1 to act on plants, their habitat and/or on seed.

* * * * *

UNITED STATES PATENT AND TRADEMARK OFFICE
CERTIFICATE OF CORRECTION

PATENT NO.    : 6,583,089 B1
DATED         : June 24, 2003
INVENTOR(S)   : Witschel et al.

It is certified that error appears in the above-identified patent and that said Letters Patent is hereby corrected as shown below:

Column 121,
Line 17, "$C_3$-$C_6$-alkoxycarbonyl" should be -- $C_1$-$C_6$-alkoxycarbonyl --.

Column 123,
Line 53, "$R^{10}$=$R^{17}$" should be -- $R^{10}$=$OR^{17}$ --.

Column 124,
Line 28, "as" should be -- for --;
Line 29, delete "$SO_2R^{18}$", duplicate occurrence;
Line 30, "were" should be -- where --;
Line 60, "R to $R^5$" should be -- $R^1$ to $R^5$ --;
Line 61, "m are defined" should be -- m are as defined --.

Signed and Sealed this

Twenty-eighth Day of October, 2003

JAMES E. ROGAN
*Director of the United States Patent and Trademark Office*